US012171814B2

United States Patent
Kweon et al.

(10) Patent No.: US 12,171,814 B2
(45) Date of Patent: Dec. 24, 2024

(54) PROTEIN COMPLEX INCLUDING BOTULINUM TOXIN TRANSLOCATION DOMAIN AND ENDOLYSIN AND ANTIBACTERIAL COMPOSITION INCLUDING SAME

(71) Applicant: MVRIX Co., Ltd., Hwaseong-si (KR)

(72) Inventors: Dae Hyuk Kweon, Seoul (KR); Wonbeom Park, Suwon-si (KR); Jihwan Chun, Seoul (KR)

(73) Assignee: MVRIX CO., LTD., Hwaseong-si (KR)

( * ) Notice: Subject to any disclaimer, the term of this patent is extended or adjusted under 35 U.S.C. 154(b) by 0 days.

(21) Appl. No.: 18/287,223

(22) PCT Filed: Apr. 18, 2022

(86) PCT No.: PCT/KR2022/005511
§ 371 (c)(1),
(2) Date: Oct. 17, 2023

(87) PCT Pub. No.: WO2022/225267
PCT Pub. Date: Oct. 27, 2022

(65) Prior Publication Data
US 2024/0091322 A1    Mar. 21, 2024

(30) Foreign Application Priority Data
Apr. 19, 2021 (KR) .................. 10-2021-0050767

(51) Int. Cl.
*A61K 38/47* (2006.01)
*A61P 31/04* (2006.01)
*C12N 9/36* (2006.01)
*C12N 9/52* (2006.01)

(52) U.S. Cl.
CPC .............. *A61K 38/47* (2013.01); *A61P 31/04* (2018.01); *C12N 9/2462* (2013.01); *C12N 9/52* (2013.01); *C12Y 302/01017* (2013.01); *C12Y 304/24069* (2013.01); *C07K 2319/034* (2013.01); *C07K 2319/92* (2013.01)

(58) Field of Classification Search
CPC .................................................. C12N 9/2462
See application file for complete search history.

(56) References Cited

U.S. PATENT DOCUMENTS 6,022,950 A    2/2000    Murphy

FOREIGN PATENT DOCUMENTS

| CN | 110272913 A | 9/2019 |
|----|---|---|
| KR | 10-2001-0089817 A | 10/2001 |
| KR | 10-2005-0077998 A | 8/2005 |
| KR | 10-1109060 B1 | 1/2012 |
| KR | 10-2012-0061802 A | 6/2012 |
| KR | 10-1505413 B1 | 3/2015 |
| KR | 10-1788096 B1 | 10/2017 |
| KR | 10-2060355 B1 | 12/2019 |
| KR | 10-2066850 B1 | 1/2020 |
| KR | 10-2097127 B1 | 4/2020 |
| KR | 10-2205690 B1 | 1/2021 |
| KR | 10-2309424 B1 | 10/2021 |
| WO | 2016/187076 A1 | 11/2016 |

OTHER PUBLICATIONS

Zampara et al., "exploiting phage receptor binding proteins to enable endolysins to kill Gram-negative bacteria" Scientific Reports, 2020, 10:12087—doi.org/10.1038/s41598-020-68983-3).*
Jochen Klumpp et al., "A perfect fit: Bacteriophage receptor-binding proteins for diagnostic and therapeutic applications", Current Opinion in Microbiology, 2023, vol. 71, 102240, pp. 1-10.
Susana P. Costa et al., "A Phage Receptor-Binding Protein as a Promising Tool for the Detection of *Escherichia coli* in Human Specimens", Frontiers in Microbiology, Jun. 2022, vol. 13, Article 871855, pp. 1-14.
Athina Zampara et al., "Exploiting phage receptor binding proteins to enable endolysins to kill Gram-negative bacteria", Scientific Reports, 2020, vol. 10, 12087, pp. 1-12.
Notice of opinion submission for KR 10-2022-0047296 dated Jan. 9, 2023.
Notice of Allowance for KR 10-2022-0047296 dated Mar. 17, 2023.
International Search Report for PCT/KR2022/005511 dated Jul. 22, 2022.

* cited by examiner

*Primary Examiner* — Suzanne M Noakes
(74) *Attorney, Agent, or Firm* — Sughrue Mion, PLLC

(57) ABSTRACT

Provided is a protein complex including a botulinum toxin translocation domain and endolysin. When used, the protein complex including a botulinum translocation domain and endolysin according to the present invention exhibits an antibacterial effect and thus can be used as an antibacterial composition or an antibiotic.

5 Claims, 18 Drawing Sheets
Specification includes a Sequence Listing.

[FIG. 1]
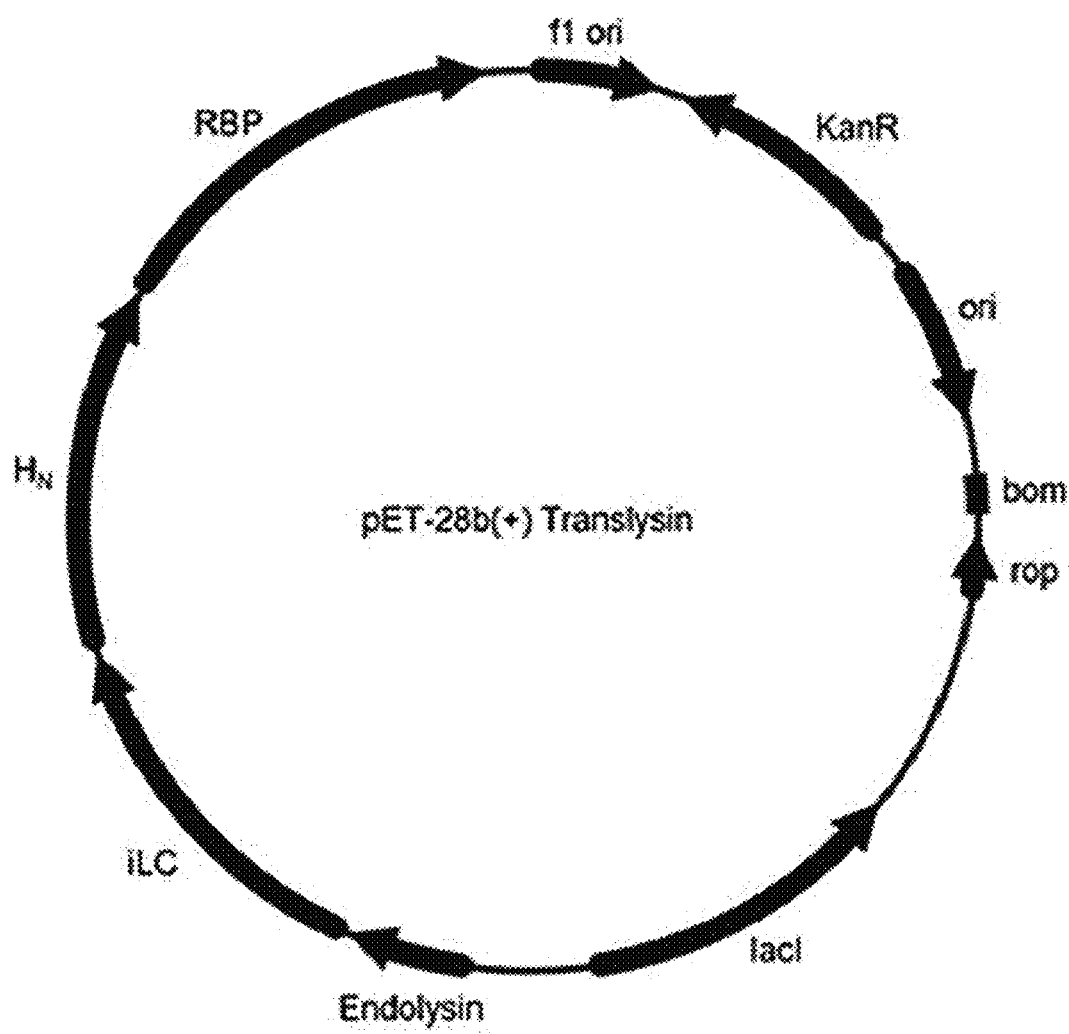

[FIG. 2]
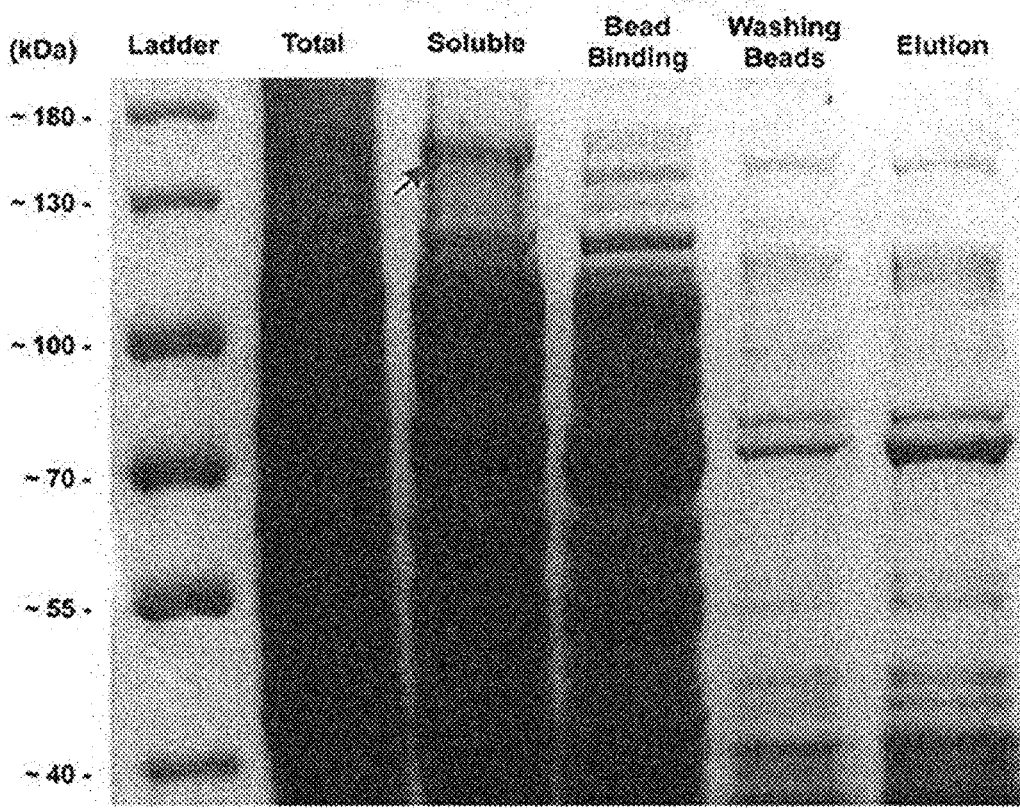

[FIG. 3]
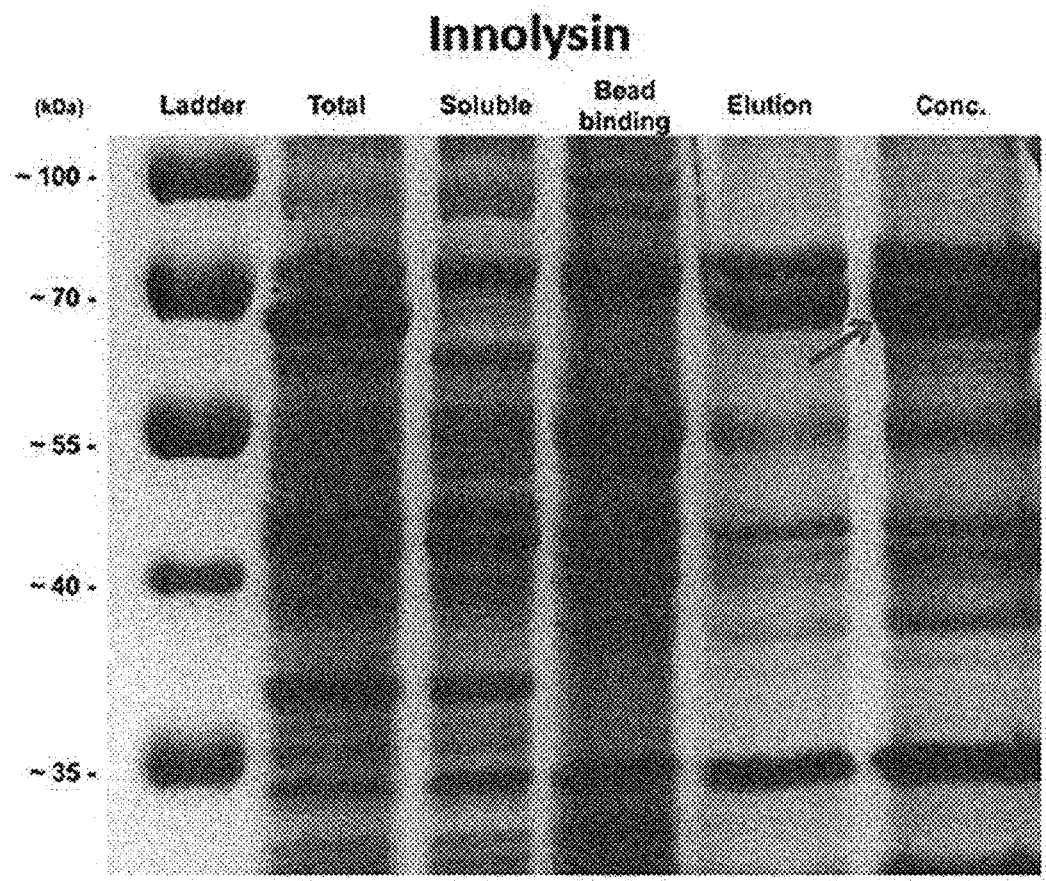
[FIG. 4]
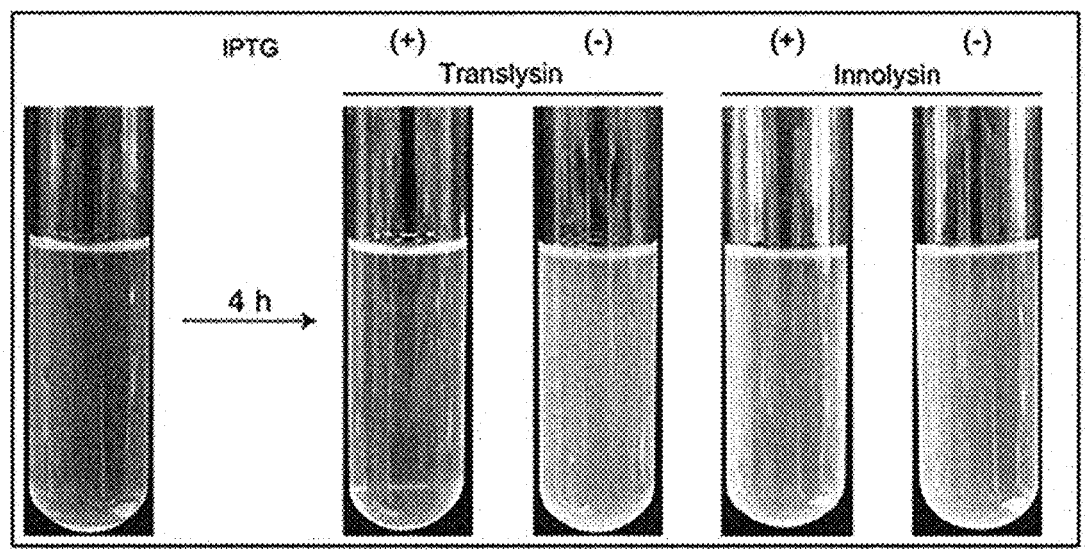

[FIG. 5]
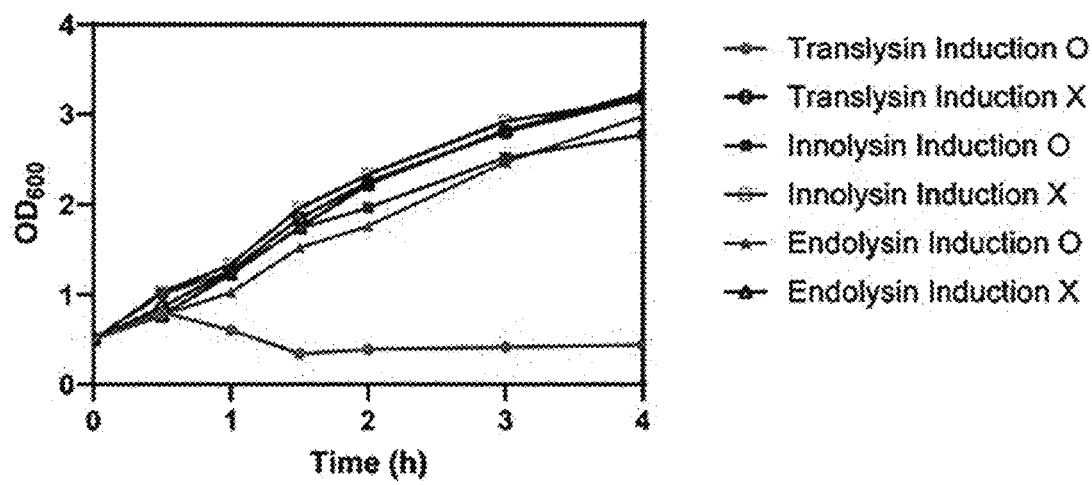
[FIG. 6]
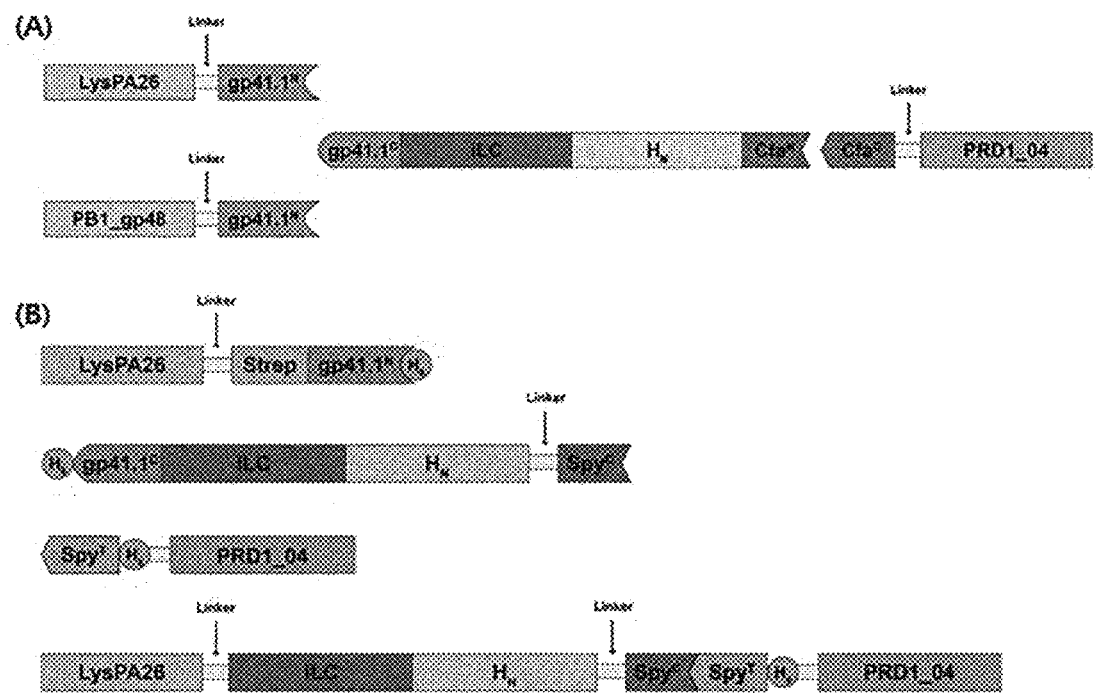

[FIG. 7]
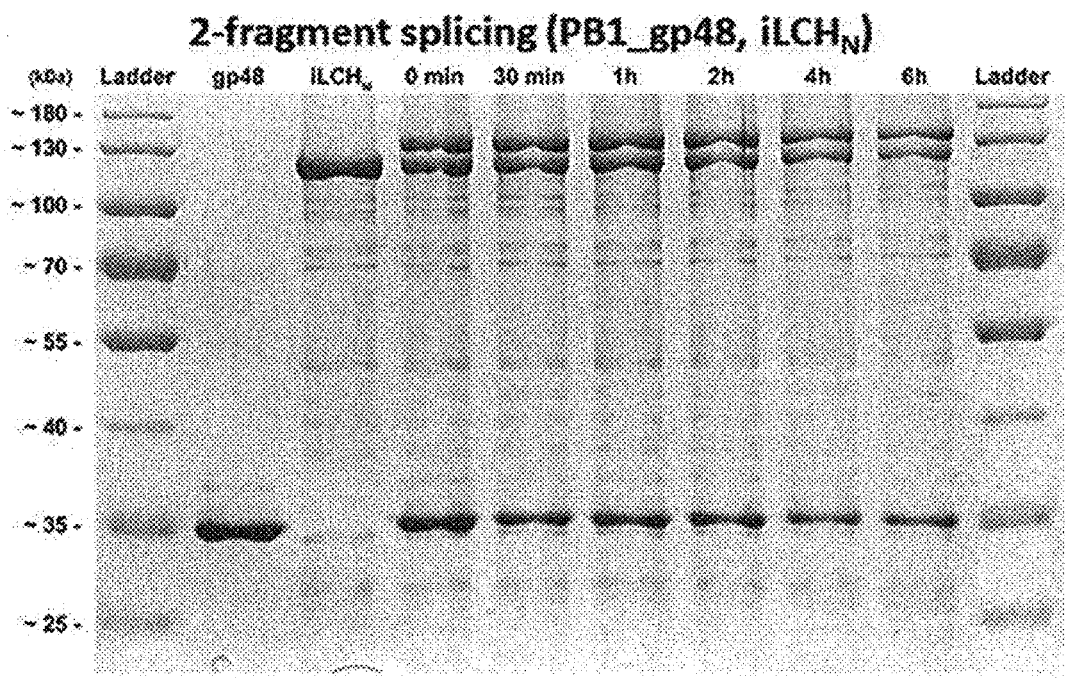

[FIG. 8]
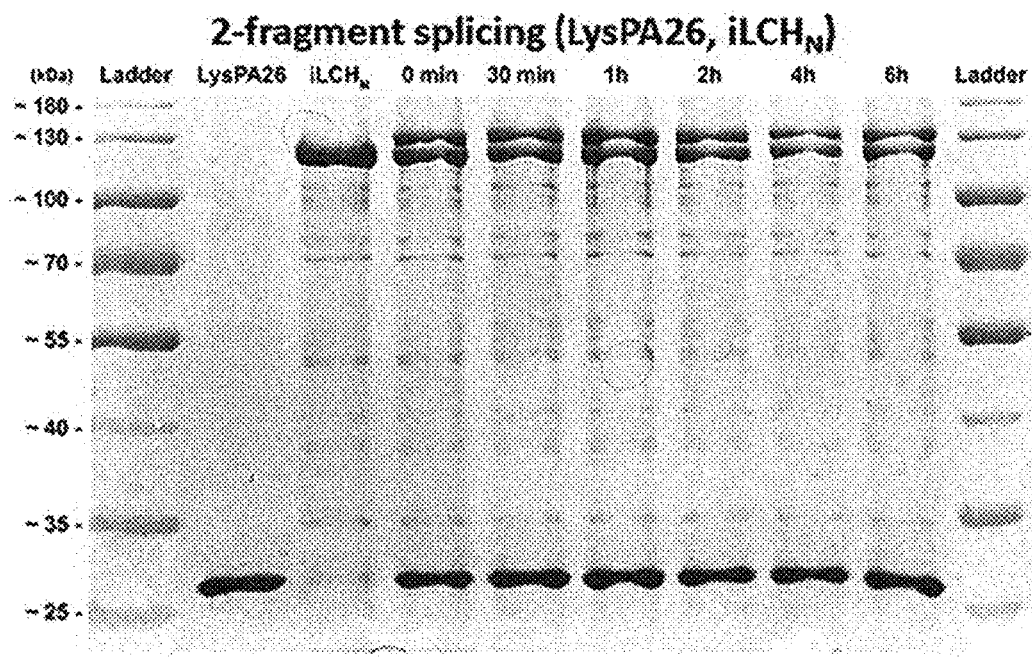
[FIG. 9]
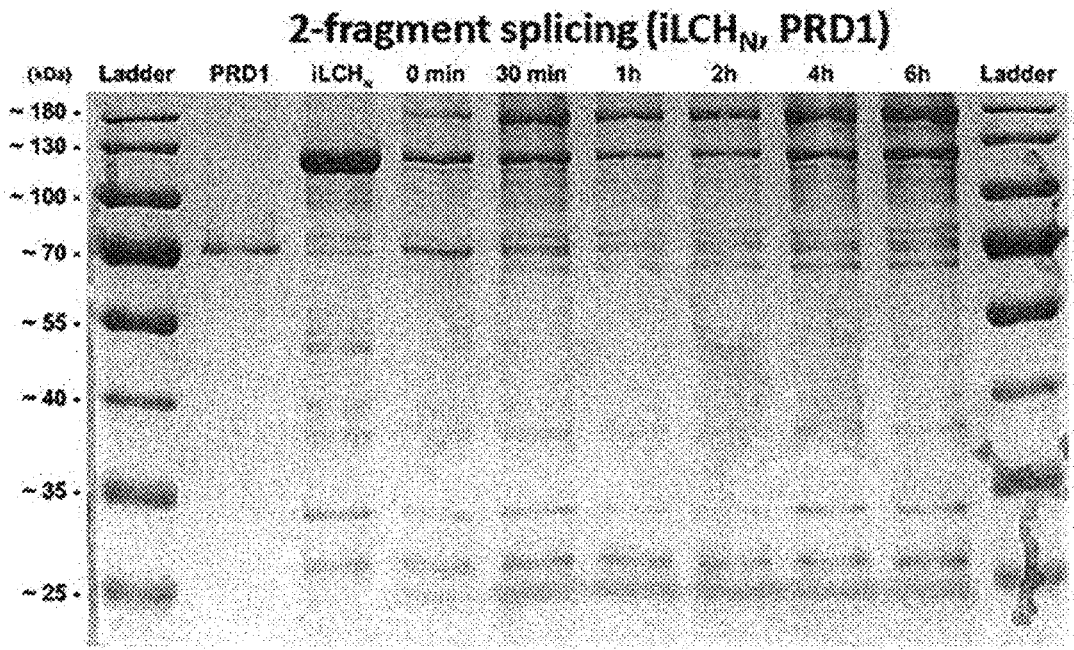

[FIG. 10]
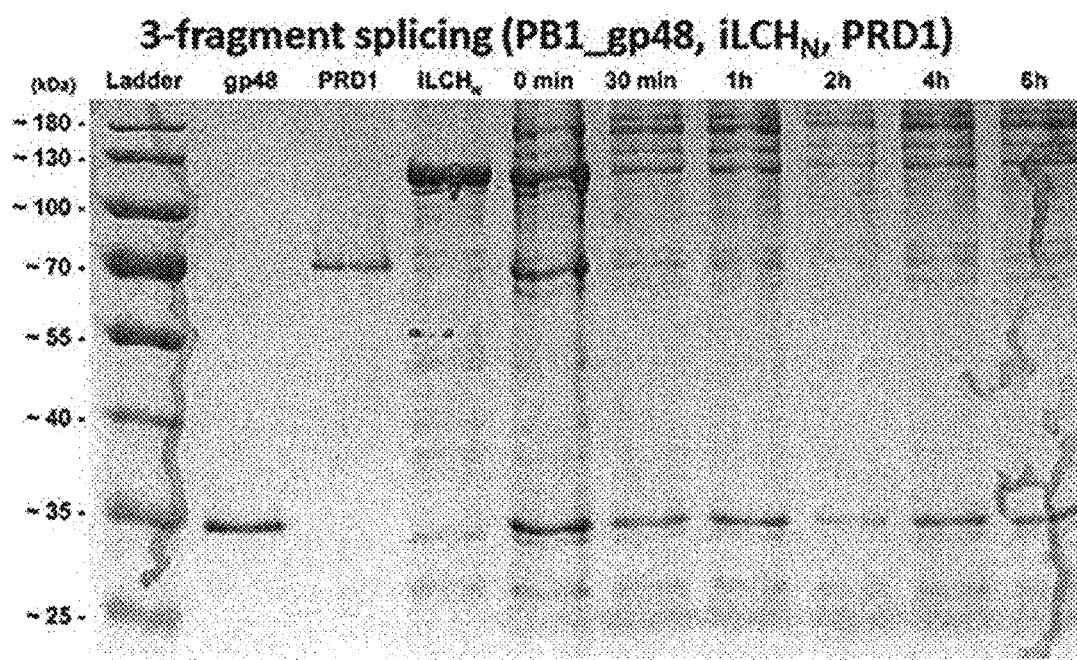
[FIG. 11]
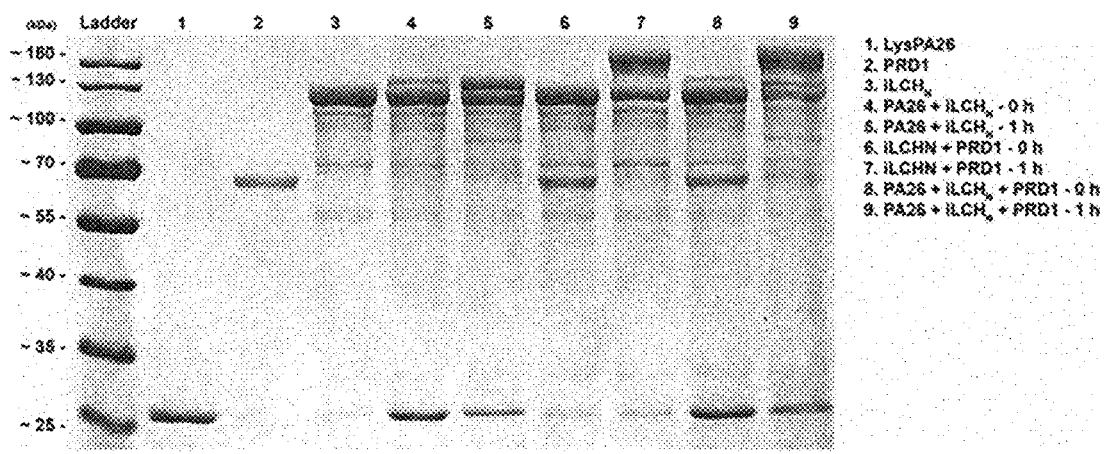

[FIG. 12]
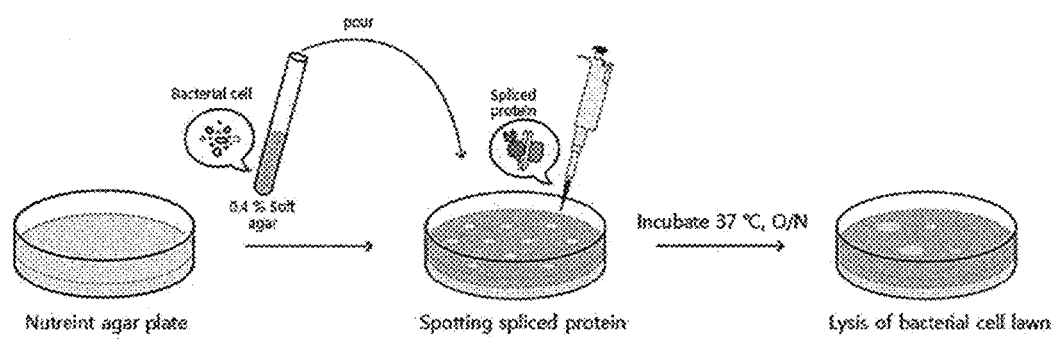
[FIG. 13]
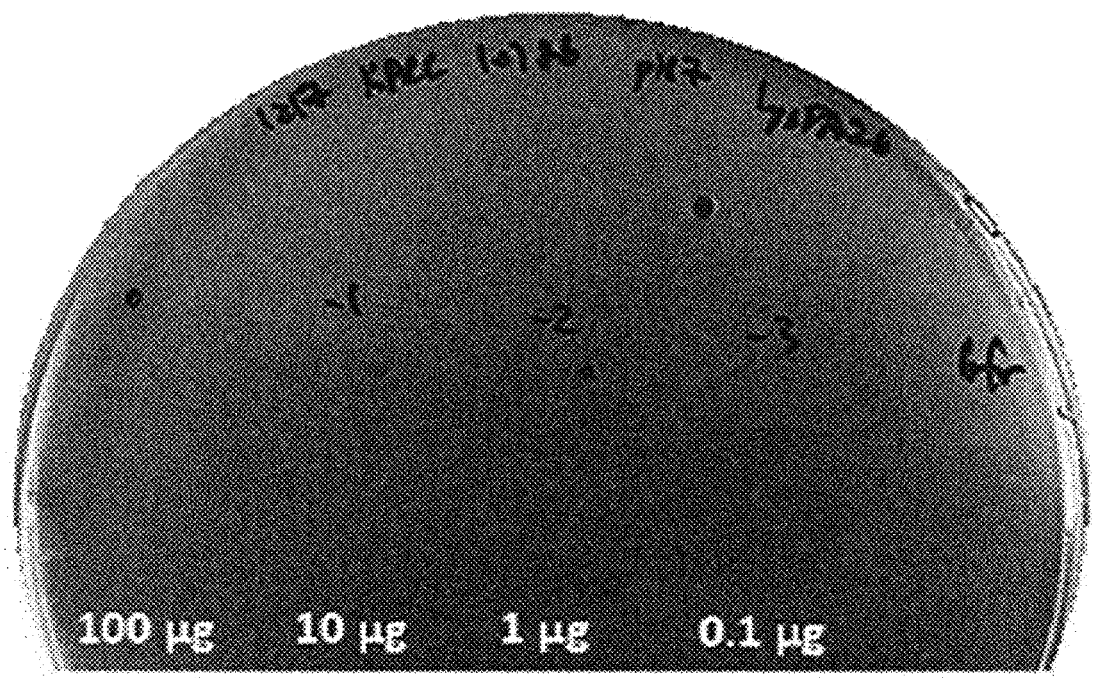

[FIG. 14]
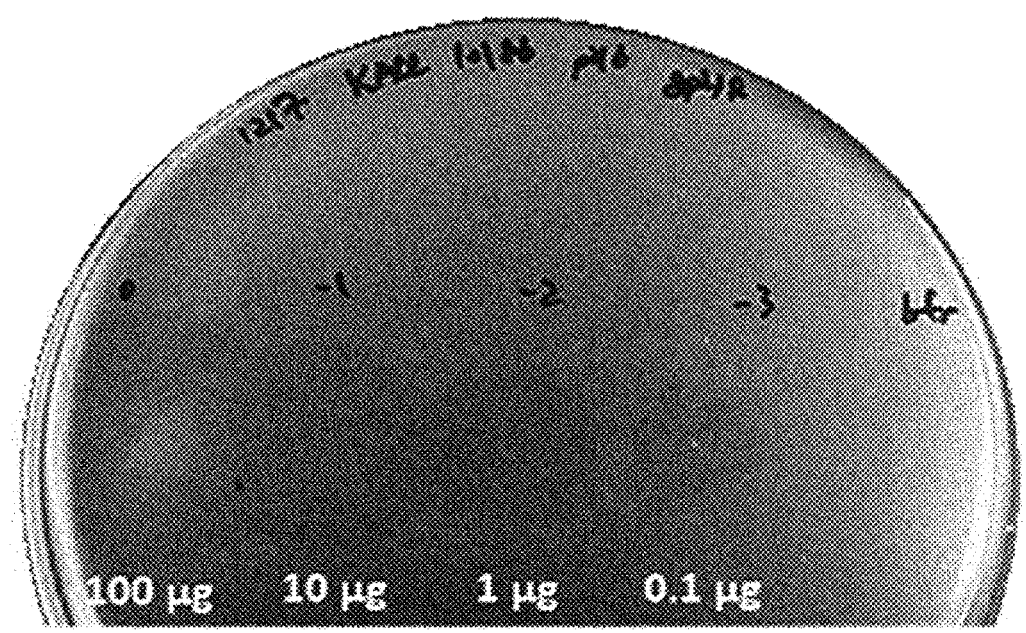

[FIG. 15]
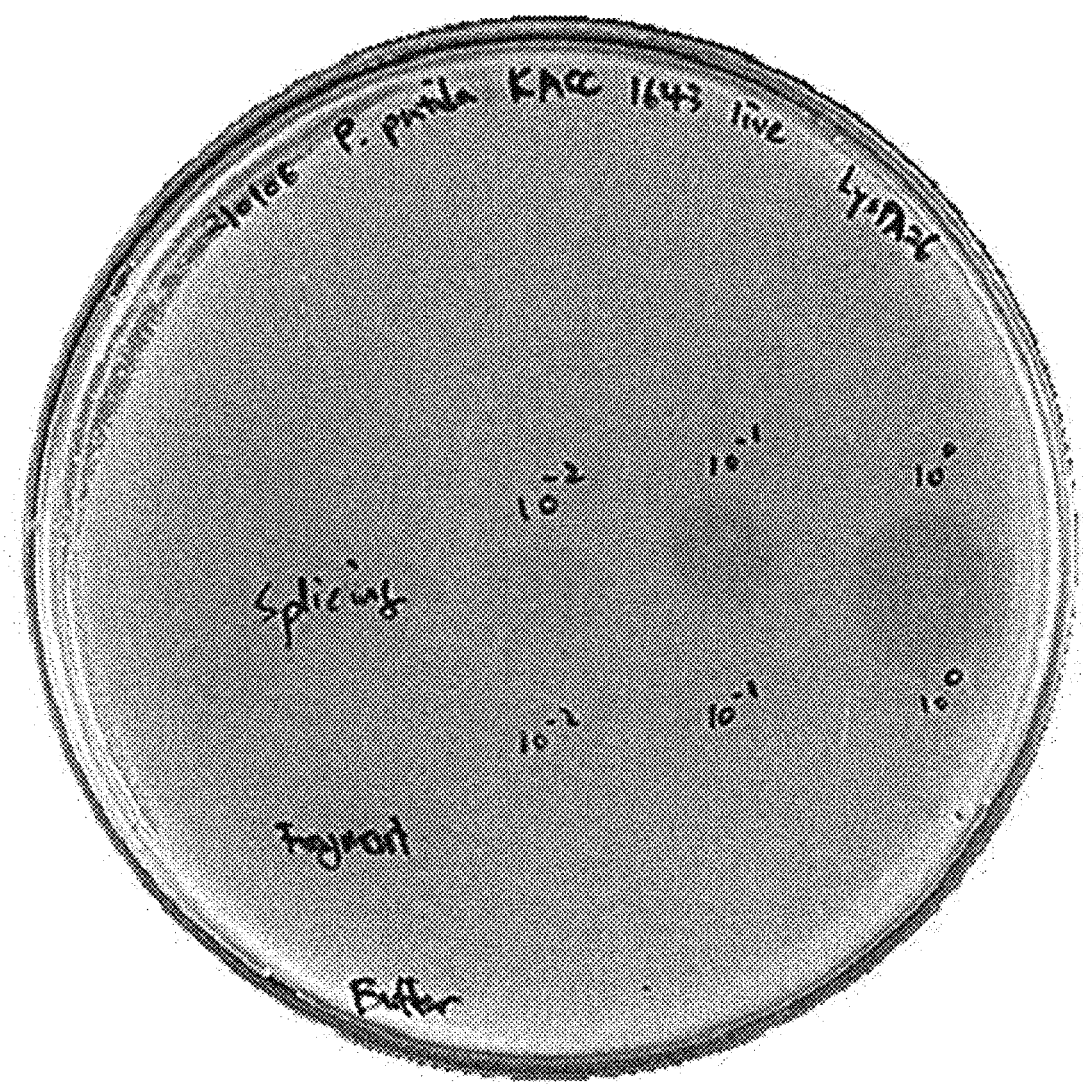

[FIG. 16]
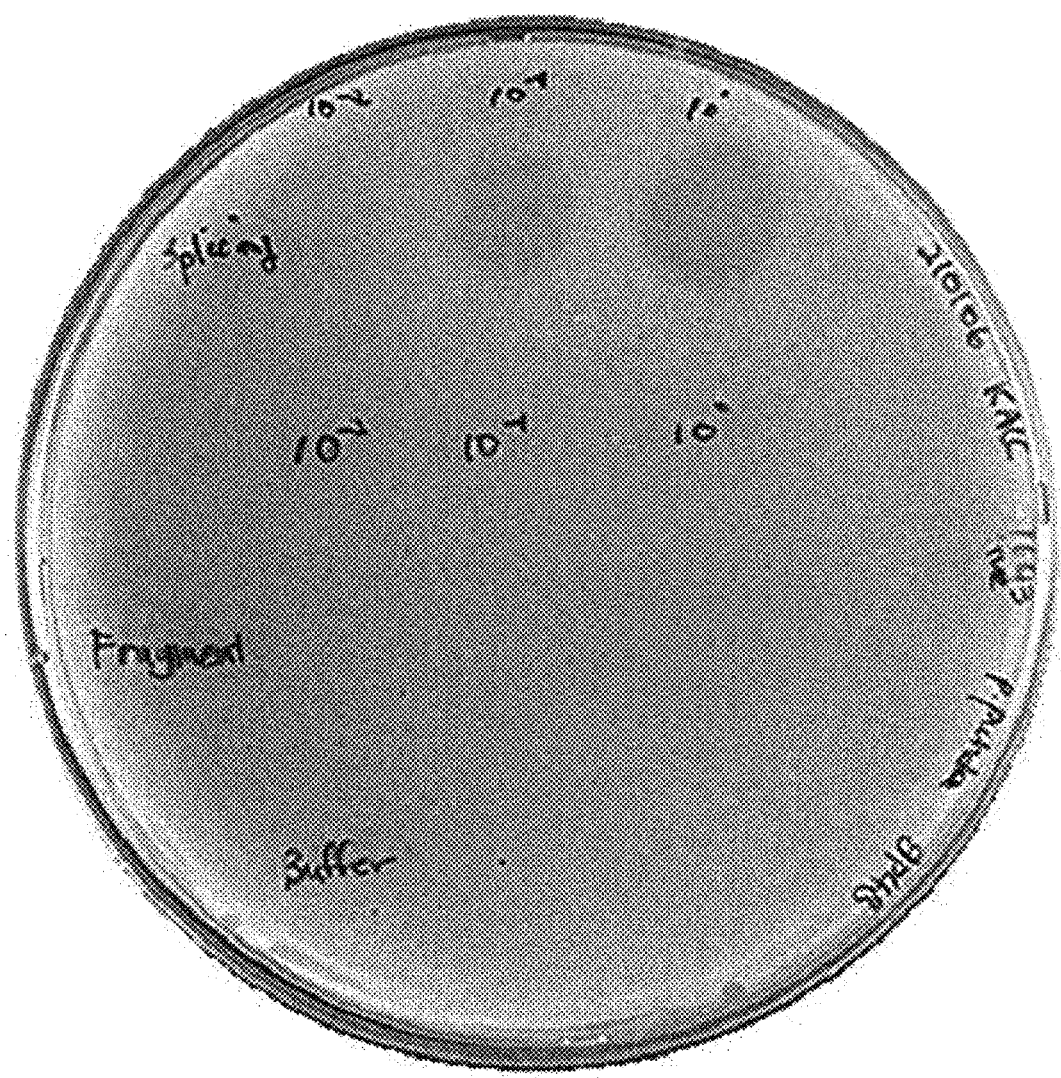

[FIG. 17]
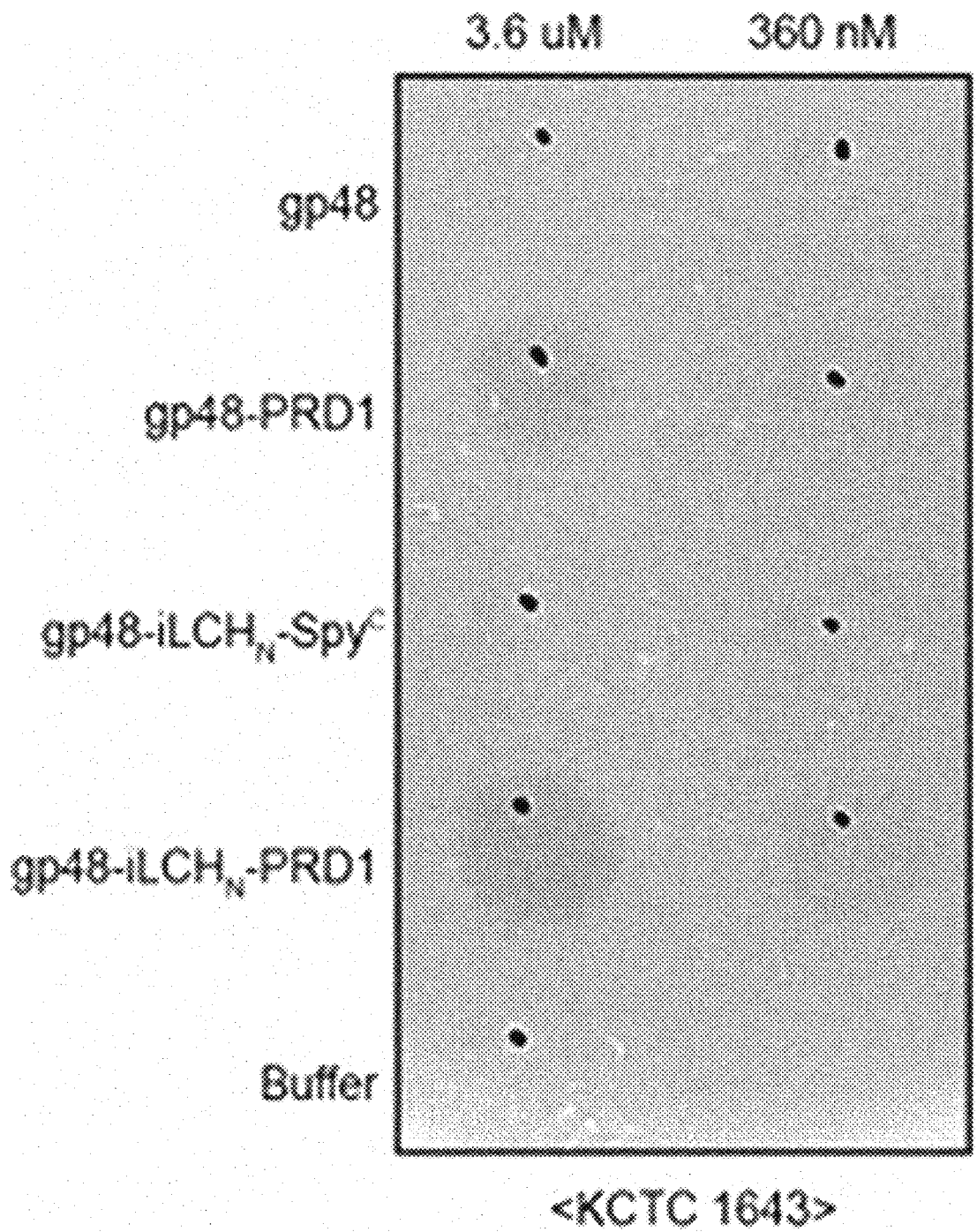

[FIG. 18]
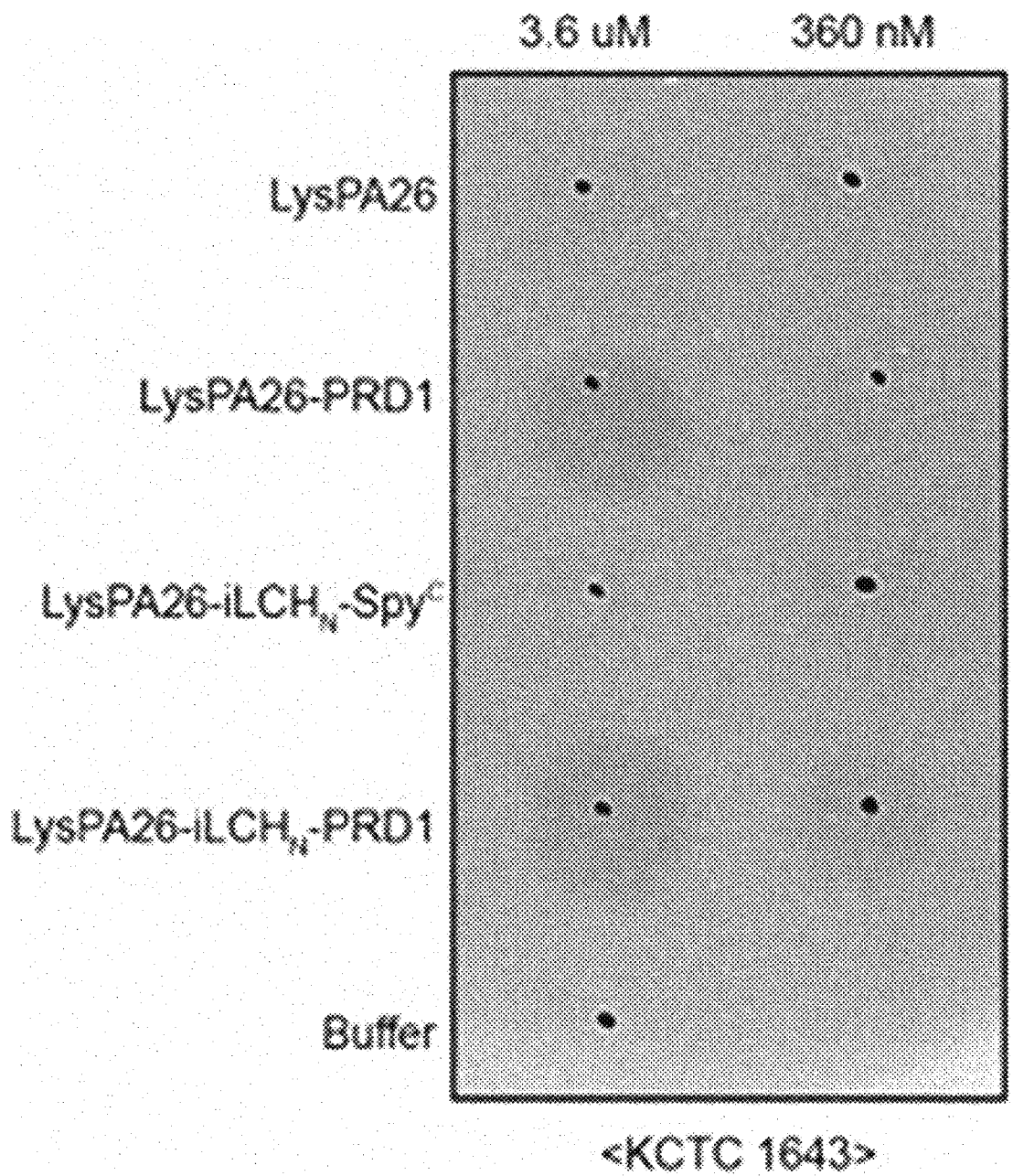

[FIG. 19]
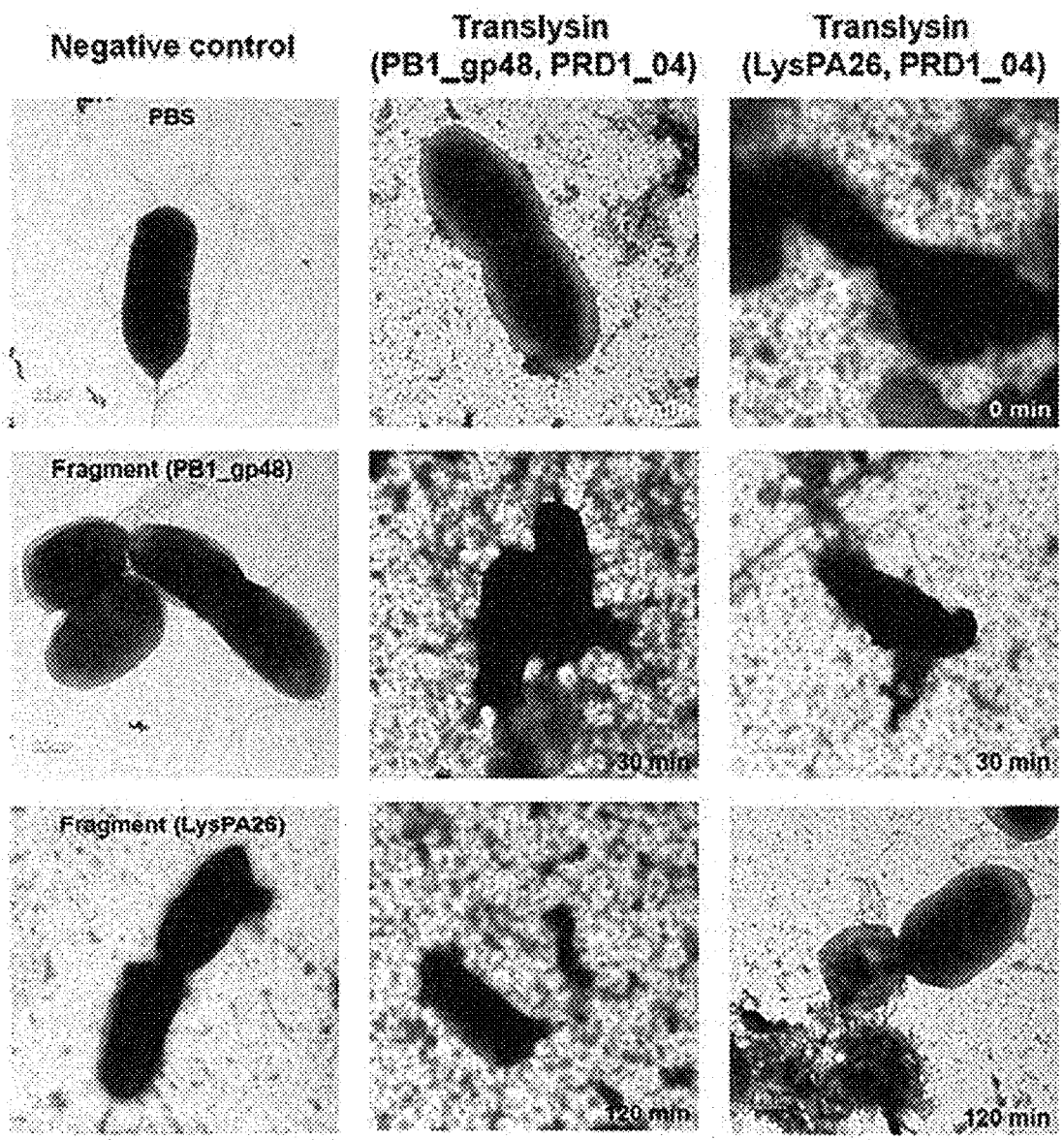

[FIG. 20]
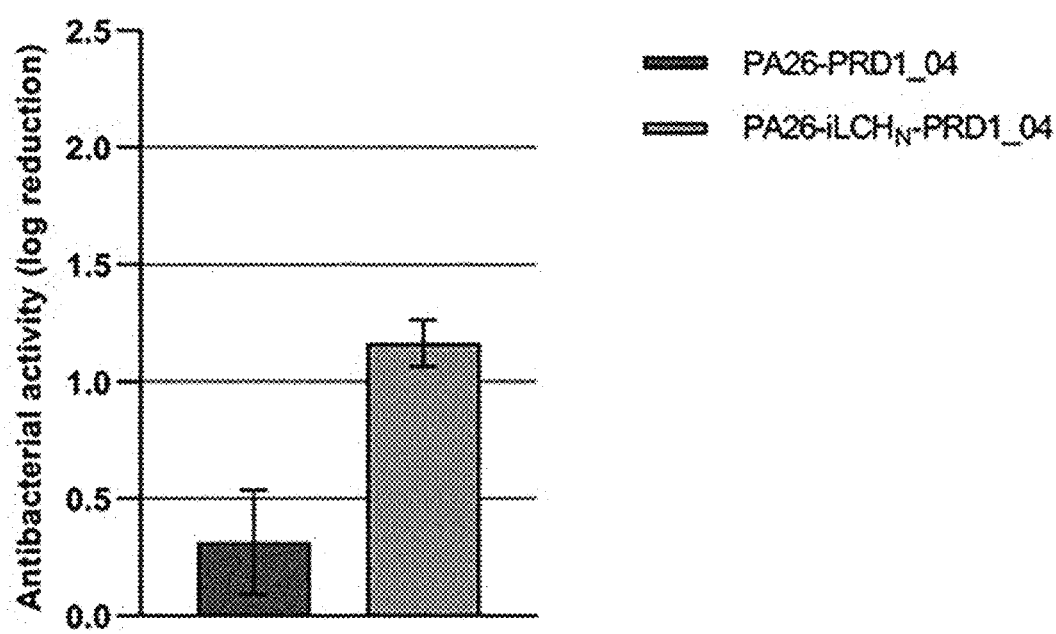

[FIG. 21]
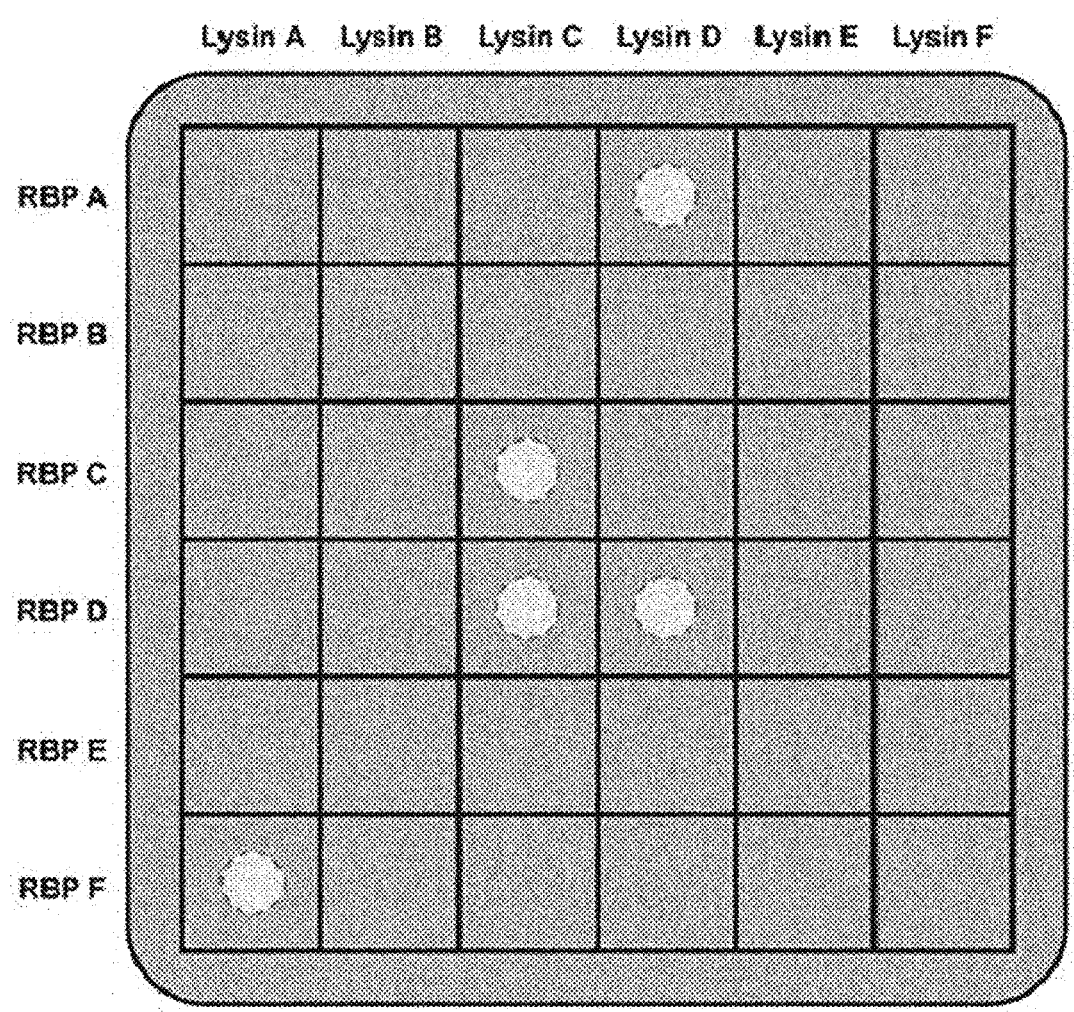

[FIG. 22]
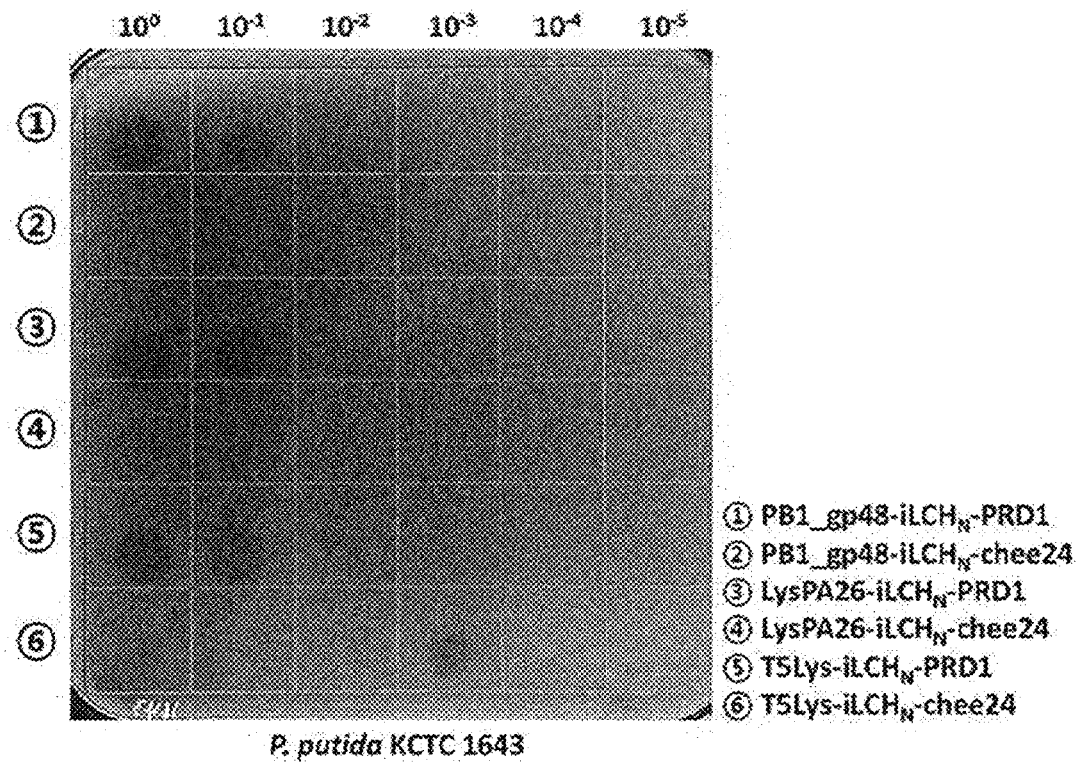
[FIG. 23]
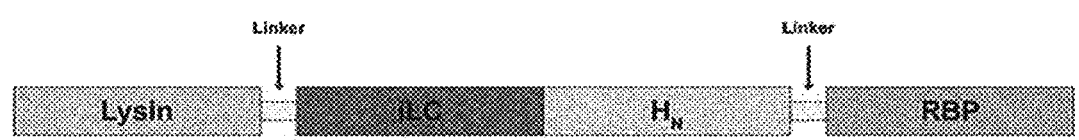
[FIG. 24]
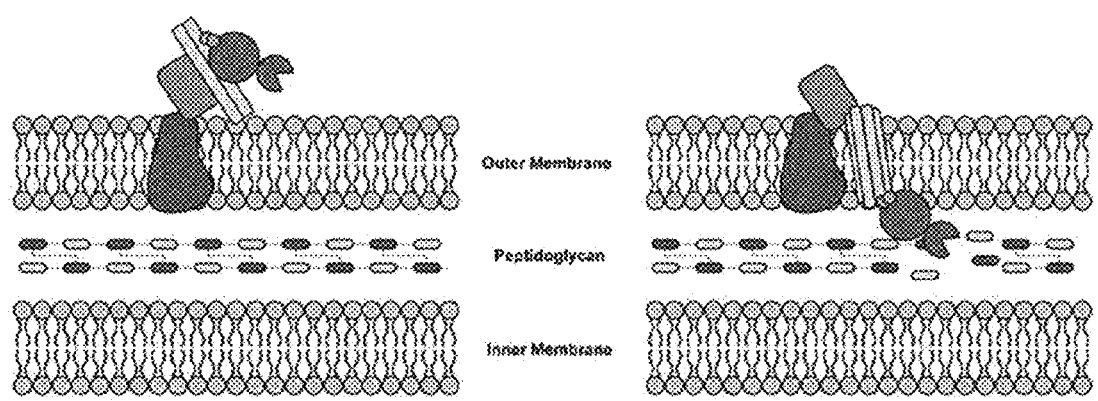

[FIG. 25]
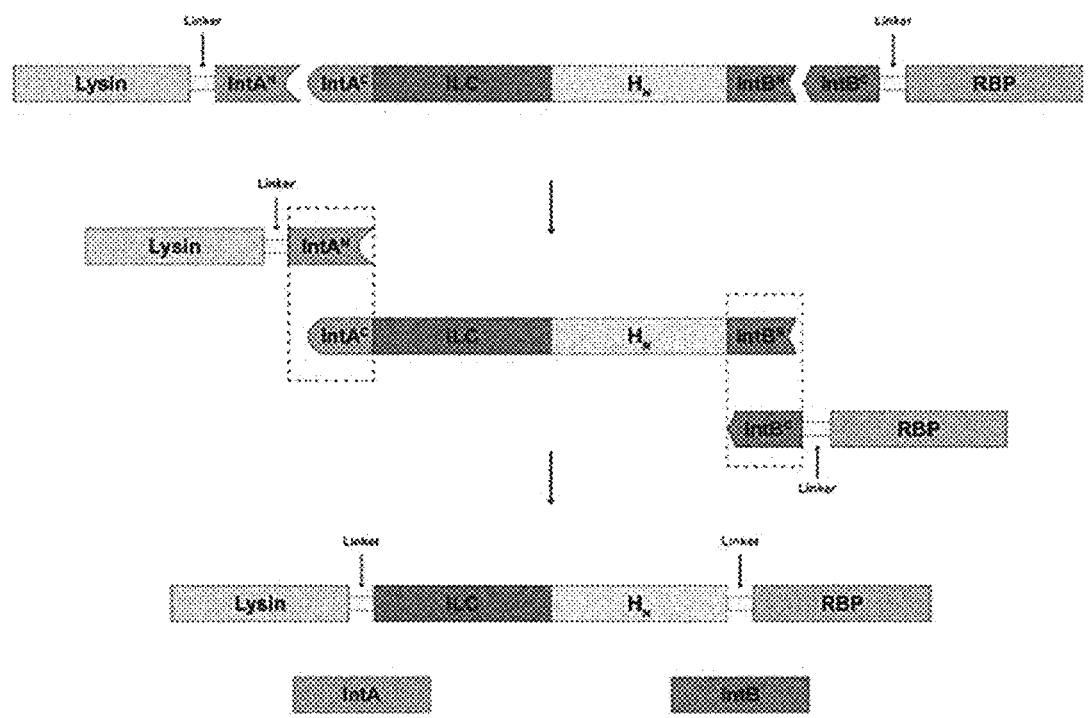
[FIG. 26]
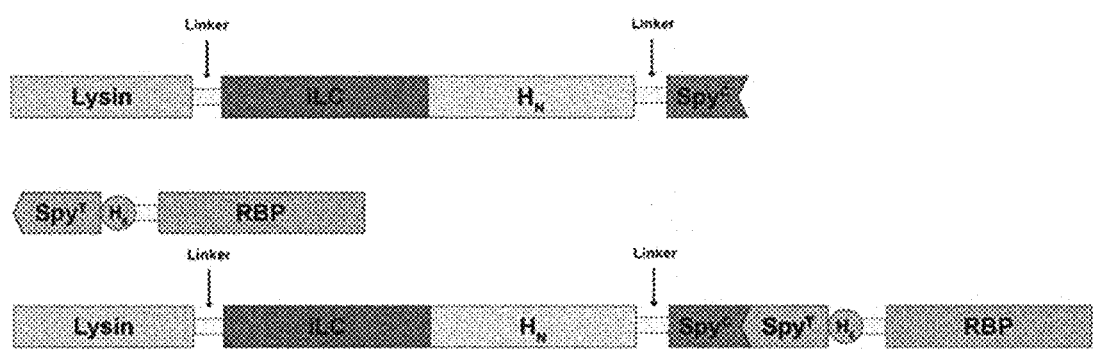

SEQUENCE LISTING

```
<160> NUMBER OF SEQ ID NOS: 42

<210> SEQ ID NO 1
<211> LENGTH: 88
<212> TYPE: PRT
<213> ORGANISM: Artificial Sequence
<220> FEATURE:
<223> OTHER INFORMATION: Gp41.1 Int-N

<400> SEQUENCE: 1

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Ser Tyr Lys
        35                  40                  45

Ile Thr Leu Glu Asp Gly Lys Glu Ile Ile Cys Ser Glu Glu His Leu
```

```
                    50                  55                  60
Phe Pro Thr Gln Thr Gly Glu Met Asn Ile Ser Gly Gly Leu Lys Glu
 65                  70                  75                  80

Gly Met Cys Leu Tyr Val Lys Glu
                 85

<210> SEQ ID NO 2
<211> LENGTH: 37
<212> TYPE: PRT
<213> ORGANISM: Artificial Sequence
<220> FEATURE:
<223> OTHER INFORMATION: Gp41.1 Int-C

<400> SEQUENCE: 2

Met Met Leu Lys Lys Ile Leu Lys Ile Glu Glu Leu Asp Glu Arg Glu
 1               5                  10                  15

Leu Ile Asp Ile Glu Val Ser Gly Asn His Leu Phe Tyr Ala Asn Asp
                20                  25                  30

Ile Leu Thr His Asn
             35

<210> SEQ ID NO 3
<211> LENGTH: 101
<212> TYPE: PRT
<213> ORGANISM: Artificial Sequence
<220> FEATURE:
<223> OTHER INFORMATION: Cfa Int-N

<400> SEQUENCE: 3

Cys Leu Ser Tyr Asp Thr Glu Ile Leu Thr Val Glu Tyr Gly Phe Leu
 1               5                  10                  15

Pro Ile Gly Lys Ile Val Glu Glu Arg Ile Glu Cys Thr Val Tyr Thr
                20                  25                  30

Val Asp Lys Asn Gly Phe Val Tyr Thr Gln Pro Ile Ala Gln Trp His
                35                  40                  45

Asn Arg Gly Glu Gln Glu Val Phe Glu Tyr Cys Leu Glu Asp Gly Ser
     50                  55                  60

Ile Ile Arg Ala Thr Lys Asp His Lys Phe Met Thr Thr Asp Gly Gln
 65                  70                  75                  80

Met Leu Pro Ile Asp Glu Ile Phe Glu Arg Gly Leu Asp Leu Lys Gln
                 85                  90                  95

Val Asp Gly Leu Pro
            100

<210> SEQ ID NO 4
<211> LENGTH: 36
<212> TYPE: PRT
<213> ORGANISM: Artificial Sequence
<220> FEATURE:
<223> OTHER INFORMATION: Cfa Int-C

<400> SEQUENCE: 4

Met Val Lys Ile Ile Ser Arg Lys Ser Leu Gly Thr Gln Asn Val Tyr
 1               5                  10                  15

Asp Ile Gly Val Glu Lys Asp His Asn Phe Leu Leu Lys Asn Gly Leu
                20                  25                  30

Val Ala Ser Asn
             35

<210> SEQ ID NO 5
```

```
<211> LENGTH: 104
<212> TYPE: PRT
<213> ORGANISM: Artificial Sequence
<220> FEATURE:
<223> OTHER INFORMATION: NRDJ-1 Int-N

<400> SEQUENCE: 5

Cys Leu Val Gly Ser Ser Glu Ile Ile Thr Arg Asn Tyr Gly Lys Thr
1               5                   10                  15

Thr Ile Lys Glu Val Val Glu Ile Phe Asp Asn Asp Lys Asn Ile Gln
            20                  25                  30

Val Leu Ala Phe Asn Thr His Thr Asp Asn Ile Glu Trp Ala Pro Ile
        35                  40                  45

Lys Ala Ala Gln Leu Thr Arg Pro Asn Ala Glu Leu Val Glu Leu Glu
    50                  55                  60

Ile Asp Thr Leu His Gly Val Lys Thr Ile Arg Cys Thr Pro Asp His
65                  70                  75                  80

Pro Val Tyr Thr Lys Asn Arg Gly Tyr Val Arg Ala Asp Glu Leu Thr
                85                  90                  95

Asp Asp Asp Glu Leu Val Val Ala
            100

<210> SEQ ID NO 6
<211> LENGTH: 41
<212> TYPE: PRT
<213> ORGANISM: Artificial Sequence
<220> FEATURE:
<223> OTHER INFORMATION: NRDJ-1 Int-C

<400> SEQUENCE: 6

Met Ile Glu Ala Lys Thr Tyr Ile Gly Lys Leu Lys Ser Arg Lys Ile
1               5                   10                  15

Val Ser Asn Glu Asp Thr Tyr Asp Ile Gln Thr Ser Thr His Asn Phe
            20                  25                  30

Phe Ala Asn Asp Ile Leu Val His Asn
        35                  40

<210> SEQ ID NO 7
<211> LENGTH: 101
<212> TYPE: PRT
<213> ORGANISM: Artificial Sequence
<220> FEATURE:
<223> OTHER INFORMATION: IMPDH-1 Int-N

<400> SEQUENCE: 7

Cys Phe Val Pro Gly Thr Leu Val Asn Thr Glu Asn Gly Leu Lys Lys
1               5                   10                  15

Ile Glu Glu Ile Lys Val Gly Asp Lys Val Phe Ser His Thr Gly Lys
            20                  25                  30

Leu Gln Glu Val Val Asp Thr Leu Ile Phe Asp Arg Asp Glu Glu Ile
        35                  40                  45

Ile Ser Ile Asn Gly Ile Asp Cys Thr Lys Asn His Glu Phe Tyr Val
    50                  55                  60

Ile Asp Lys Glu Asn Ala Asn Arg Val Asn Glu Asp Ile His Leu Phe
65                  70                  75                  80

Ala Arg Trp Val Val His Ala Glu Glu Leu Asp Met Lys Lys His Leu
                85                  90                  95

Leu Ile Glu Leu Glu
            100
```

<210> SEQ ID NO 8
<211> LENGTH: 40
<212> TYPE: PRT
<213> ORGANISM: Artificial Sequence
<220> FEATURE:
<223> OTHER INFORMATION: IMPDH-1 Int-C

<400> SEQUENCE: 8

```
Met Lys Phe Lys Leu Lys Glu Ile Thr Ser Ile Glu Thr Lys His Tyr
1               5                   10                  15

Lys Gly Lys Val His Asp Leu Thr Val Asn Gln Asp His Ser Tyr Asn
            20                  25                  30

Val Arg Gly Thr Val Val His Asn
            35                  40
```

<210> SEQ ID NO 9
<211> LENGTH: 100
<212> TYPE: PRT
<213> ORGANISM: Artificial Sequence
<220> FEATURE:
<223> OTHER INFORMATION: Npu Int-N

<400> SEQUENCE: 9

```
Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
            35                  40                  45

Asp Arg Gly Glu Gln Glu Val Phe Glu Tyr Cys Leu Glu Asp Gly Ser
        50                  55                  60

Leu Ile Arg Ala Thr Lys Asp His Lys Met Thr Val Asp Gly Gln Met
65                  70                  75                  80

Leu Pro Ile Asp Glu Ile Phe Glu Arg Glu Leu Asp Leu Met Arg Asp
                85                  90                  95

Asn Leu Pro Asn
            100
```

<210> SEQ ID NO 10
<211> LENGTH: 36
<212> TYPE: PRT
<213> ORGANISM: Artificial Sequence
<220> FEATURE:
<223> OTHER INFORMATION: Npu Int-C

<400> SEQUENCE: 10

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn
            35
```

<210> SEQ ID NO 11
<211> LENGTH: 123
<212> TYPE: PRT
<213> ORGANISM: Artificial Sequence
<220> FEATURE:
<223> OTHER INFORMATION: Ssp Int-N

<400> SEQUENCE: 11

```
Cys Leu Ser Phe Gly Thr Glu Ile Leu Thr Val Glu Tyr Gly Pro Leu
1               5                   10                  15

Pro Ile Gly Lys Ile Val Ser Glu Ile Asn Cys Ser Val Tyr Ser
            20                  25                  30

Val Asp Pro Glu Gly Arg Val Tyr Thr Gln Ala Ile Ala Gln Trp His
            35                  40                  45

Asp Arg Gly Glu Gln Glu Val Leu Glu Tyr Glu Leu Glu Asp Gly Ser
        50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
            115                 120
```

<210> SEQ ID NO 12
<211> LENGTH: 36
<212> TYPE: PRT
<213> ORGANISM: Artificial Sequence
<220> FEATURE:
<223> OTHER INFORMATION: Ssp Int-C

<400> SEQUENCE: 12

```
Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn
        35
```

<210> SEQ ID NO 13
<211> LENGTH: 122
<212> TYPE: PRT
<213> ORGANISM: Artificial Sequence
<220> FEATURE:
<223> OTHER INFORMATION: Rma Int-N

<400> SEQUENCE: 13

```
Cys Leu Ala Gly Asp Thr Leu Ile Thr Leu Ala Asp Gly Arg Arg Val
1               5                   10                  15

Pro Ile Arg Glu Leu Val Ser Gln Gln Asn Phe Ser Val Trp Ala Leu
            20                  25                  30

Asn Pro Gln Thr Tyr Arg Leu Ala Arg Val Ser Arg Ala Arg Val Ser
            35                  40                  45

Arg Ala Phe Cys Thr Gly Ile Lys Pro Val Tyr Arg Leu Thr Thr Arg
        50                  55                  60

Leu Gly Arg Ser Ile Arg Ala Thr Ala Asn His Arg Phe Leu Thr Gln
65                  70                  75                  80

Gly Trp Lys Arg Val Asp Glu Leu Gln Pro Gly Asp Tyr Leu Ala Leu
                85                  90                  95

Pro Arg Arg Ile Pro Thr Ala Ser Thr Pro Thr Leu Thr Glu Ala Glu
            100                 105                 110

Leu Ala Leu Leu Gly His Leu Ile Gly Asp
            115                 120
```

<210> SEQ ID NO 14

```
<211> LENGTH: 37
<212> TYPE: PRT
<213> ORGANISM: Artificial Sequence
<220> FEATURE:
<223> OTHER INFORMATION: Rma Int-C

<400> SEQUENCE: 14

Met Trp Asp Pro Ile Val Ser Ile Glu Pro Asp Gly Val Glu Val
1               5                   10                  15

Phe Asp Leu Thr Val Pro Gly Pro His Asn Phe Val Ala Asp Asn Ile
            20                  25                  30

Ile Ala Gly Asn Ser
        35

<210> SEQ ID NO 15
<211> LENGTH: 118
<212> TYPE: PRT
<213> ORGANISM: Artificial Sequence
<220> FEATURE:
<223> OTHER INFORMATION: Ppu Int-N

<400> SEQUENCE: 15

Cys Ile Ser Lys Phe Ser His Ile Met Trp Ser His Val Ser Lys Pro
1               5                   10                  15

Leu Phe Asn Phe Ser Ile Lys Lys Ser His Met His Asn Gly Asn Lys
            20                  25                  30

Asn Ile Tyr Gln Leu Leu Asp Gln Gly Glu Ala Phe Ile Ser Arg Gln
        35                  40                  45

Asp Lys Lys Thr Thr Tyr Lys Ile Arg Thr Asn Ser Glu Lys Tyr Leu
    50                  55                  60

Glu Leu Thr Ser Asn His Lys Ile Leu Thr Leu Arg Gly Trp Gln Arg
65                  70                  75                  80

Cys Asp Gln Leu Leu Cys Asn Asp Met Ile Thr Thr Gln Ile Gly Phe
                85                  90                  95

Glu Leu Ser Arg Lys Lys Lys Tyr Leu Leu Asn Cys Ile Pro Phe Ser
            100                 105                 110

Leu Cys Asn Phe Glu Thr
        115

<210> SEQ ID NO 16
<211> LENGTH: 34
<212> TYPE: PRT
<213> ORGANISM: Artificial Sequence
<220> FEATURE:
<223> OTHER INFORMATION: Ppu Int-C

<400> SEQUENCE: 16

Met Leu Ala Asn Ile Asn Ile Ser Asn Phe Gln Asn Val Phe Asp Phe
1               5                   10                  15

Ala Ala Asn Pro Ile Pro Asn Phe Ile Ala Asn Asn Ile Ile Val His
            20                  25                  30

Asn Ser

<210> SEQ ID NO 17
<211> LENGTH: 88
<212> TYPE: PRT
<213> ORGANISM: Artificial Sequence
<220> FEATURE:
<223> OTHER INFORMATION: Gp41.8 Int-N

<400> SEQUENCE: 17
```

```
Cys Leu Ser Leu Asp Thr Met Val Val Thr Asn Gly Lys Ala Ile Glu
1               5                   10                  15

Ile Arg Asp Val Lys Val Gly Asp Trp Leu Glu Ser Glu Cys Gly Pro
            20                  25                  30

Val Gln Val Thr Glu Val Leu Pro Ile Ile Lys Gln Pro Val Phe Glu
        35                  40                  45

Ile Val Leu Lys Ser Gly Lys Lys Ile Arg Val Ser Ala Asn His Lys
    50                  55                  60

Phe Pro Thr Lys Asp Gly Leu Lys Thr Ile Asn Ser Gly Leu Lys Val
65                  70                  75                  80

Gly Asp Phe Leu Arg Ser Arg Ala
                85
```

<210> SEQ ID NO 18
<211> LENGTH: 45
<212> TYPE: PRT
<213> ORGANISM: Artificial Sequence
<220> FEATURE:
<223> OTHER INFORMATION: Gp41.8 Int-C

<400> SEQUENCE: 18

```
Met Cys Glu Ile Phe Glu Asn Glu Ile Asp Trp Asp Glu Ile Ala Ser
1               5                   10                  15

Ile Glu Tyr Val Gly Val Glu Glu Thr Ile Asp Ile Asn Val Thr Asn
            20                  25                  30

Asp Arg Leu Phe Phe Ala Asn Gly Ile Leu Thr His Asn
            35                  40                  45
```

<210> SEQ ID NO 19
<211> LENGTH: 105
<212> TYPE: PRT
<213> ORGANISM: Artificial Sequence
<220> FEATURE:
<223> OTHER INFORMATION: NrdA-2 Int-N

<400> SEQUENCE: 19

```
Cys Leu Thr Gly Asp Ala Lys Ile Asp Val Leu Ile Asp Asn Ile Pro
1               5                   10                  15

Ile Ser Gln Ile Ser Leu Glu Glu Val Val Asn Leu Phe Asn Glu Gly
            20                  25                  30

Lys Glu Tyr Val Leu Ser Tyr Asn Ile Asp Thr Lys Glu Val Glu Tyr
        35                  40                  45

Lys Glu Ile Ser Asp Ala Gly Leu Ile Ser Glu Ser Ala Glu Val Leu
    50                  55                  60

Glu Ile Ile Asp Glu Glu Thr Gly Gln Lys Ile Val Cys Thr Pro Asp
65                  70                  75                  80

His Lys Val Tyr Thr Leu Asn Arg Gly Tyr Val Ser Ala Lys Asp Leu
                85                  90                  95

Lys Glu Asp Asp Glu Leu Val Phe Ser
            100                 105
```

<210> SEQ ID NO 20
<211> LENGTH: 35
<212> TYPE: PRT
<213> ORGANISM: Artificial Sequence
<220> FEATURE:
<223> OTHER INFORMATION: NrdA-2 Int-C

<400> SEQUENCE: 20

Met Gly Leu Lys Ile Ile Lys Arg Glu Ser Lys Glu Pro Val Phe Asp

|   | 1 |   |   |   | 5 |   |   |   |   | 10 |   |   |   |   | 15 |
|---|---|---|---|---|---|---|---|---|---|----|---|---|---|---|----|

Ile Thr Lys Val Lys Asp Asn Ser Asn Phe Phe Ala Asn Asn Ile Leu
         20            25            30

Val His Asn
    35

```
<210> SEQ ID NO 21
<211> LENGTH: 4527
<212> TYPE: DNA
<213> ORGANISM: Artificial Sequence
<220> FEATURE:
<223> OTHER INFORMATION: Translysin (T5 lys endolysin - HN - Pb5 RBP)

<400> SEQUENCE: 21
atgcatcatc atcatcatca cagcttcaaa ttcggcaaaa acagcgaaaa acagctggca      60
accgttaaac cggaactgca gaaagttgca cgtcgtgcac tggaactgag cccgtatgat     120
tttaccattg ttcagggtat tcgtaccgtt gcacagagcg cacagaatat tgcaaatggc     180
accagctttc tgaaagatcc gagcaaaagc aaacatatta ccggtgatgc aattgatttc     240
gcaccgtata ttaacggcaa aatcgattgg aatgatctgg aagcattttg ggcagtgaaa     300
aaagcatttg aacaggcagg taaagaactg gtattaaac tgcgttttgg tgcagattgg     360
aacgcaagcg gtgattatca tgatgaaatt aaacgtggca cctatgatgg tggtcatgtt     420
gaactggttg gtggaggcgg tagcccgttt gtgaacaaac agttcaacta taagagatccg     480 gtgaacggtg ttgatatcgc ctatatcaaa attccgaatg caggtcagat gcagccggtt     540
aaagccttta aatccataa caaaatttgg gtgattccgg aacgtgatac ctttaccaat     600
ccggaagaag gtgatctgaa tccgcctccg gaagcaaaac aggttccggt tagctattat     660
gatagcacct atctgagcac cgataacgag aaagataact atctgaaagg tgtgaccaaa     720
ctgtttgaac gcatttatag taccgatctg gtcgtatgc tgctgaccag cattgttcgt     780
ggtattccgt tttggggtgg tagcaccatt gataccgaac tgaaagttat tgacaccaac     840
tgcattaatg tgattcagcc ggatggtagc atcgtagcg aagaactgaa tctggttatt     900
attggtccga cgcagatat cattcagttt gaatgtaaaa gctttggcca cgatgttctg     960
aatctgaccc gtaatggtta tggtagtacc cagtatattc gtttcagtcc ggattttacc    1020
tttggctttg aagaaagcct ggaagttgat acaaatccgc tgttaggtgc aggtaaattt    1080
gcaaccgatc cggcagttac cctggcacat gaactgattc atgccgaaca tcgtctgtat    1140
ggtattgcca ttaatccgaa tcgtgtgttc aaagtgaata ccaacgccta ttatgaaatg    1200
agcggtctgg aagtgagttt tgaagaactg cgtacctttg gtggtcatga tgccaaattt    1260
atcgatagcc tgcaagaaaa tgaatttcgc ctgtactact ataacaaatt caaagatgtt    1320
gcgagcaccc tgaataaagc caaaagcatt attggcacca ccgcaagcct gcagtatatg    1380
aaaaatgtgt ttaaagaaaa atatctgctg agcgaagata ccagcggtaa atttagcgtt    1440
gacaaactga aattcgataa actgtacaag atgctgaccg agatttatac cgaagataac    1500
ttcgtgaact tctttaaggt gatcaacgcc aaaaccttcc tgaactttga taaagccgtg    1560
tttcgcatta acattgtgcc ggatgaaaac tacaccatca aagatggctt taatctgaag    1620
ggtgcaaatc tgtccaccaa ttttaacggt cagaacaccg aaattaacag ccgtaatttt    1680
acccgtctga aaactttac cggtctgttc gaattttaca aactgctgtg tgttcgtggc    1740
attatcccgt ttaagagaa cctgtatttt cagggtgcac tgaatgatct gtgcatcaaa    1800
gtgaataatt gggacctgtt tttagcccg agcgaagata actttaccaa cgatctggat    1860
```

```
aaagtggaag aaattaccgc agataccaat attgaagcag ccgaagaaaa cattagcctg    1920
gatctgattc agcagtatta tctgaccttc gattttgata acgagccgga aaatatcagc    1980
attgaaaatc tgagcagcga tattattggt cagctggaac cgatgccgaa tattgaacgt    2040
tttccgaatg caaaaaata cgagctggac aaatatacca tgttccatta tctgcgtgcc    2100
caagaatttg aacatggtga tagccgcatt attctgacca attcagcaga agaagcactg    2160
ctgaaaccga atgttgcata tccttttttc agcagcaaat atgtgaaaaa atcaacaaa    2220 gccgtcgaag cctttatgtt tctgaattgg gctgaagaac tggtgtatga tttcaccgat    2280
gaaaccaatg aagttaccac catggataaa attgccgaca ttaccattat cgtgccgtat    2340
attggtccgg ctctgaatat tggcaatatg ctgagcaaag gtgaatttgt ggaagccatt    2400
atctttaccg gtgttgttgc aatgctggaa tttatcccgg aatatgcact gccggttttt    2460
ggcacctttg caattgttag ctatatcgcc aataaagttc tgaccgttca gaccattaat    2520
aacgcactga gcaaacgcaa tgagaaatgg gatgaagtgt ataaatacac cgttaccaat    2580
tggctggcca agttaatac ccagattgat ctgatccgcg agaaaatgaa aaaagccctg    2640
gaaaatcagg cagaagcaac caaagcaatt atcaactatc agtacaacca gtacaccgag    2700
gaagagaaaa acaacatcaa cttcaacatc gatgacctga gcagcaaact gaatgaaagc    2760
attaatagcg ccatgattaa catcaacaag tttctggatc agtgcagcgt tagctatctg    2820
atgaatagca tgattccgta tgcagtgaaa cgcctgaaag attttgatgc aagcgttcgt    2880
gatgtcctgc tgaaatatat ctatgataat cgtggcaccc tggttctgca ggttgatcgt    2940
ctgaaagatg aagttaataa caccctgagc gcagatattc cgtttcagct gagtaaatat    3000
gtggacaaca aaaactgct gagcacctttt accgagtaca tcaaaaacgg tggaggcggt    3060
agcatgagct tctttgcagg caaactgaac aacaaaagca ttctgagcct gcgtcgtggt    3120
agcggtggtg ataccaatca gcatattaat ccggatagcc agaccatctt tcatagcgat    3180
atgagccatg tgattatcac cgaaacacat agcaccggtc tgcgtctgga tcaaggtgcc    3240
ggtgattact attggagcga aatgccgagc cgtgttaccc agctgcataa taatgatccg    3300
aatcgtgttg ttctgaccga aattgaattt agtgatggta gccgtcatat gctgagcggt    3360
atgagcatgg gtgttggtgc aaaagcatat ggtattatca tccgcagat tatgagccaa    3420 ggtggtctga aacccagat taccgcaagc gcagatctga gtctggatgt tggctatttt    3480
aacaccggta caagcggcac cattccgcag aaactgcgtg atggcaccgg ttgccagcat    3540
atgtttggtc catttagcgg tcgtcgtggt ttgcaagca gcgcaatgta tttaggtggt    3600
gcagcactgt ataaaagcgc atggtcaggt agcggttatg ttgttgcaga tgcaggcacc    3660
ctgaccattc cgagcgatta tgttcgtcat ccgggtgcac gtaattttgg ttttaatgca    3720
atctatgttc gtggtcgtag ctgtaatcgt gttctgtatg gtatggaagg tccgaattat    3780
acaaccggta gtgccgttca gggtgcgagc agcagcggtg cactgaattt tacctataat    3840
ccgagcaatc cggaaagccc gaaatatagc gttggtttg ccgtgcaga tccgaccaat    3900 tatgcctatt gggaaagtat gggcgatccg aatgatagcg caaatggtcc gattggtatt    3960
tatagcgaac atctgggtat ctacccgagc aaaattacct ggtatgttac caatctggtg    4020
tataatggta gcggctataa cattgatggt ggtctgttta atggcaacga cattaaactg    4080
agtccgcgtg aattcattat caaaggcgtg aatgtgaata taccagctg gaagtttatc    4140 aacttcatcg agaaaaactt caacgtgggt aatcgtgcag attttcgtga tgttggttgt    4200
```

| | |
|---|---:|
| aacctgagca aagatagccc gagcaccggt attagcggta ttgcaacctt tggtctgccg | 4260 |
| accaccgaaa gcaataatgc accgagcatt aaaggtggta atgttggtgg cctgcatgca | 4320 |
| aatgttgtta gcatttataa ctttctgccg agcgcaagct ggtatgtgag cagcaatccg | 4380 |
| cctaaaattg gtaataacta tggtgatgtg tggtccgaga atctgctgcc gctgcgtctg | 4440 |
| ttaggtggta gtggtagcac cattctgagt ggtaatattg tgtttcaagg taatggcagc | 4500 |
| gttcatgttg gcaccgttgg tctggat | 4527 |

```
<210> SEQ ID NO 22
<211> LENGTH: 1911
<212> TYPE: DNA
<213> ORGANISM: Artificial Sequence
<220> FEATURE:
<223> OTHER INFORMATION: Innolysin (T5 lys endolysin - linker - Pb5 RBP)

<400> SEQUENCE: 22
```

| | |
|---|---:|
| atgagcttca aattcggcaa aaacagcgaa aacagctgg caaccgttaa accggaactg | 60 |
| cagaaagttg cacgtcgtgc actggaactg agcccgtatg attttaccat tgttcagggt | 120 |
| attcgtaccg ttgcacacga gcgcacagaa attgcaaatg caccagctt tctgaaagat | 180 |
| ccgagcaaaa gcaaacatat taccggtgat gcaattgatt tcgcaccgta tattaacggc | 240 |
| aaaatcgatt ggaatgatct ggaagcattt tgggcagtga aaaagcatt tgaacaggca | 300 |
| ggtaaagaac tgggtattaa actgcgtttt ggtgcagatt ggaacgcaag cggtgattat | 360 |
| catgatgaaa ttaaacgtgg cacctatgat ggtggtcatg ttgaactggt tgcaggtgca | 420 |
| ggcgcaggca tgagcttctt tgcaggcaaa ctgaacaaca aaagcattct gagcctgcgt | 480 |
| cgtggtagcg gtggtgatac caatcagcat attaatccgg atagccagac catctttcat | 540 |
| agcgatatga gccatgtgat tatcaccgaa acacatagca ccgtctgcg tctggatcaa | 600 |
| ggtgccggtg attactattg gagcgaaatg ccgagccgtg ttacccagct gcataataat | 660 |
| gatccgaatc gtgttgttct gaccgaaatt gaatttagtg atggtagccg tcatatgctg | 720 |
| agcggtatga gcatgggtgt tggtgcaaaa gcatatggta ttatcaatcc gcagattatg | 780 |
| agccaaggtg gtctgaaaac ccagattacc gcaagcgcag atctgagtct ggatgttggc | 840 |
| tatttttaaca ccggtacaag cggcaccatt ccgcagaaac tgcgtgatgg caccggttgc | 900 |
| cagcatatgt ttggtgcatt tagcggtcgt cgtggttttg caagcagcgc aatgtattta | 960 |
| ggtggtgcag cactgtataa aagcgcatgg tcaggtagcg gttatgttgt tgcagatgca | 1020 |
| ggcaccctga ccattccgag cgattatgtt cgtcatccgg tgcacgtaa ttttggtttt | 1080 |
| aatgcaatct atgttcgtgg tcgtagctgt aatcgtgttc tgtatggtat ggaaggtccg | 1140 |
| aattatacaa ccggtggtgc cgttcagggt gcgagcagca gcggtgcact gaattttacc | 1200 |
| tataatccga gcaatccgga aagcccgaaa tatagcgttg gttttgcccg tgcagatccg | 1260 |
| accaattatg cctattggga aagtatgggc gatccgaatg atagcgcaaa tggtccgatt | 1320 |
| ggtatttata gcgaacatct gggtatctac ccgagcaaaa ttacctggta tgttaccaat | 1380 |
| ctggtgtata atggtagcgg ctataacatt gatggtggtc tgtttaatgg caacgacatt | 1440 |
| aaactgagtc cgcgtgaatt cattatcaaa ggcgtgaatg tgaataatac cagctggaag | 1500 |
| tttatcaact tcatcgagaa aaacttcaac gtgggtaatc gtgcagattt tcgtgatgtt | 1560 |
| ggttgtaacc tgagcaaaga tagcccgagc accggtatta gcggtattgc aacctttggt | 1620 |
| ctgccgacca ccgaaagcaa taatgcaccg agcattaaag tggtaatgt tggtggcctg | 1680 |
| catgcaaatg ttgttagcat ttataacttt ctgccgagcg caagctggta tgtgagcagc | 1740 |

```
aatccgccta aaattggtaa taactatggt gatgtgtggt ccgagaatct gctgccgctg    1800
cgtctgttag gtggtagtgg tagcaccatt ctgagtggta atattgtgtt tcaaggtaat    1860
ggcagcgttc atgttggcac cgttggtctg gatcatcatc atcatcatca c             1911
```

```
<210> SEQ ID NO 23
<211> LENGTH: 738
<212> TYPE: DNA
<213> ORGANISM: Artificial Sequence
<220> FEATURE:
<223> OTHER INFORMATION: LysPA26-Gp41.1N

<400> SEQUENCE: 23
```

```
atgcgcacca ataacattga tgccatcaaa gaacatgaag gtctgcgtct ggttgcatat     60
ctggatagcg ttggtgtttg gaccattggt tatggtgata ccggtccgga tgttgttaaa    120
ggtctgacca ttaccaaaga agaagcagaa aaacgtctgc gtaaacgtct ggtggaattt    180
gaaggttatg tgaacaccta tgttaaagtg ccgctgaaac agcatcagtt tgatgcactg    240
gttagcctgg tttataacat tggtccgacc aactttaaaa caagcaccct gctgaaaaaa    300
ctgaacgcag gcgattatat tggtcagcag atcagtttc tggtgtggaa taaaggtcgt     360
gttgatggta aactggtggt tattaaaggc ctggcaaatc gtcgtgcaaa agaacgtaaa    420
cagttcctgg gtgaaggtgg aggcggtagc ggttattgcc tggatctgaa acccaggtt     480 cagacaccgc agggtatgaa agaaatttca atattcagg tgggtgatct ggttctgagc     540
aataccggtt ataatgaagt gctgaatgtg ttcccgaaaa gcaagaaaaa aagctacaaa    600 atcacccctgg aagatggcaa agaaattatc tgtagcgaag aacacctgtt tccgacacag   660
accggtgaaa tgaatattag cggtggtctg aaagaaggta tgtgcctgta tgttaaagaa    720
catcatcatc atcatcac                                                 738
```

```
<210> SEQ ID NO 24
<211> LENGTH: 963
<212> TYPE: DNA
<213> ORGANISM: Artificial Sequence
<220> FEATURE:
<223> OTHER INFORMATION: PB1_gp48-Gp41.1N

<400> SEQUENCE: 24
```

```
atgaagatca ccaaagatat tctgattacc ggcaccggtt gtaccaccga tcgtgcaatt     60
aaatggctgg atgatattca ggcagccatg gataaatttc agattgaaag tccgcgtgca    120
attgccgcat atctggcaaa tattggtgtt gaaagcggtg gtctggttag cctggttgaa    180
aatctgaatt atagcgcaca aggtctggcc aatacctggc ctcgtcgtta tgcagttgat    240
ccgcgtgttc gtccgtatgt tccgaatgca ctggcaaatc gtctggcacg taatccggtt    300
gccattgcaa ataatgttta tgcagatcgc atgggtaatg ttgtgaaca ggatggtgat     360 ggttggaaat atcgtggtcg tggtctgatt cagctgaccg gtaaaagcaa ttatgcactg    420
tttgccgaag atagcggtat ggatgttctg gaaaaaccgg aactgctgga acaccggca    480 ggcgcaagca tgagcagcgc atggttttt tggcgtaatc gttgtattcc gatggccgaa    540
agcaataact ttagcatggt ggtgaaaacc attaacggtt cagcaccgaa tgatgcaaat    600
catggtcagc tgcgtattaa ccgttatgtt aaaaccgttg cagccattaa tcagggcagc    660
ggtggaggcg gtagcggtta ttgcctggat ctgaaacccc aggttcagac accgcagggt    720
atgaaagaaa tttcaaatat tcaggtgggt gatctggttc tgagcaatac cggttataat    780
```

```
gaagtgctga atgtgttccc gaaaagcaag aaaaaaagct acaaaatcac cctggaagat    840
ggcaaagaaa ttatctgtag cgaagaacac ctgtttccga cacagaccgg tgaaatgaat    900
attagcggtg gtctgaaaga aggtatgtgc ctgtatgtta agaacatca tcatcatcat    960
cac                                                                  963
```

<210> SEQ ID NO 25
<211> LENGTH: 3054
<212> TYPE: DNA
<213> ORGANISM: Artificial Sequence
<220> FEATURE:
<223> OTHER INFORMATION: Gp41.1C-iLCHN-CfaN

<400> SEQUENCE: 25

```
atgatgctga aaaaaatcct gaaaatcgag gaactggatg aacgcgaact gattgatatt     60
gaagttagcg gtaaccacct gttctatgcc aatgatattc tgacccataa tagcagcagc    120
ccgtttgtga caaacagtt caactataaa gatccggtga acgtgttga tatcgcctat     180
atcaaaattc gaatgcagg tcagatgcag ccggttaaag cctttaaaat ccataacaaa    240
atttgggtga ttccggaacg tgataccttt accaatccgg aagaaggtga tctgaatccg    300
cctccggaag caaacaggt tccggttagc tattatgata gcacctatct gagcaccgat    360
aacgagaaag ataactatct gaaaggtgtg accaaactgt ttgaacgcat ttatagtacc    420
gatctgggtc gtatgctgct gaccagcatt gttcgtggta ttccgttttg ggtggtagc    480
accattgata ccgaactgaa agttattgac accaactgca ttaatgtgat tcagccggat    540
ggtagctatc gtagcgaaga actgaatctg gttattattg gtccgagcgc agatatcatt    600
cagtttgaat gtaaaagctt tggccacgat gttctgaatc tgacccgtaa tggttatggt    660
agtacccagt atattcgttt cagtccggat tttaccttg gctttgaaga aagcctggaa    720
gttgatacaa tccgctgtt aggtgcaggt aaatttgcaa ccgatccggc agttaccctg    780
gcacatgaac tgattcatgc cgaacatcgt ctgtatggta ttgccattaa tccgaatcgt    840
gtgttcaaag tgaataccaa cgcctattat gaaatgagcg gtctggaagt gagttttgaa    900
gaactgcgta ccttttggtgg tcatgatgcc aaatttatcg atagcctgca agaaaatgaa    960
tttcgcctgt actactataa caaattcaaa gatgttgcga gcacctgaa taaagccaaa   1020
agcattattg gcaccaccgc aagcctgcag tatatgaaaa atgtgtttaa agaaaaatat   1080
ctgctgagcg aagataccag cggtaaattt agcgttgaca aactgaaatt cgataaactg   1140
tacaagatgc tgaccgagat ttataccgaa gataacttcg tgaacttctt taaggtgatc   1200
aacgcgaaaa cctttctgaa ctttgataaa gccgtgtttc gcattaacat tgtgccggat   1260
gaaaactaca ccatcaaaga tggctttaat ctgaagggtg caaatctgtc caccaatttt   1320
aacggtcaga caccgaaat taacagccgt aattttaccc gtctgaaaaa cttaccggt   1380
ctgttcgaat ttacaaact gctgtgtgtt cgtggcatta tccgtttaa agagaacctg   1440
tatttcagg gtgcactgaa tgatctgtgc atcaaagtga taattggga cctgttttt   1500
agcccgagcg aagataactt taccaacgat ctggataaag tggaagaaat taccgcagat   1560
accaatattg aagcagccga gaaaacatt agcctggatc tgattcagca gtattatctg   1620
accttcgatt ttgataacga gccggaaaat atcagcattg aaatctgag cagcgatatt   1680
attggtcagc tggaaccgat gccgaatatt gaacgttttc gaatggcaa aaaatacgag   1740
ctggacaaat ataccatgtt ccattatctg cgtgcccaag aatttgaaca tggtgatagc   1800
cgcattattc tgaccaattc agcagaagaa gcactgctga aaccgaatgt tgcatatacc   1860
```

-continued

```
tttttcagca gcaaatatgt gaaaaaaatc aacaaagccg tcgaagcctt tatgtttctg     1920
aattgggctg aagaactggt gtatgatttc accgatgaaa ccaatgaagt taccaccatg     1980
gataaaattg ccgacattac cattatcgtg ccgtatattg gtccggctct gaatattggc     2040
aatatgctga gcaaaggtga atttgtggaa gccattatct ttaccggtgt tgttgcaatg     2100
ctggaattta tcccggaata tgcactgccg gttttttggca cctttgcaat tgttagctat     2160
atcgccaata aagttctgac cgttcagacc attaataacg cactgagcaa acgcaatgag     2220
aaatgggatg aagtgtataa ataccaccgtt accaattggc tggccaaagt taatacccag     2280
attgatctga tccgcgagaa aatgaaaaaa gccctggaaa tcaggcaga agcaaccaaa      2340 gcaattatca actatcagta caaccagtac accgaggaag agaaaaacaa catcaacttc     2400
aacatcgatg acctgagcag caaactgaat gaaagcatta tagcgccat gattaacatc      2460 aacaagtttc tggatcagtg cagcgttagc tatctgatga atagcatgat tccgtatgca     2520
gtgaaacgcc tgaaagattt tgatgcaagc gttcgtgatg tcctgctgaa atatatctat     2580
gataatcgtg gcaccctggt tctgcaggtt gatcgtctga agatgaagt taataacacc      2640 ctgagcgcag atattccgtt tcagctgagt aaatatgtgg acaacaaaaa actgctgagc     2700
acctttaccg agtacatcaa aaacgccgaa tattgcctgt cttacgacac agagattctg     2760
accgttgaat atggattcct tcctatcggt aagatcgtgg aggaacggat tgaatgcaca     2820
gtctatacgg tagataaaaa tggctttgtg tatacacaac ctattgctca gtggcataac     2880
cggggagaac aggaagtttt cgaatactgc ttagaagacg gttcgattat ccgtgcaacg     2940
aaagatcaca aatttatgac gaccgacggt cagatgttac cgattgatga gttttcgaa      3000 cgggggttag acctgaaaca agttgatggt tgccgcacc accaccacca ccac            3054
```

<210> SEQ ID NO 26
<211> LENGTH: 1923
<212> TYPE: DNA
<213> ORGANISM: Artificial Sequence
<220> FEATURE:
<223> OTHER INFORMATION: CfaC-PRD1_04

<400> SEQUENCE: 26

```
atgcatcatc atcatcatca cgtcaagatc attagtcgta agagtctggg cactcaaaac     60
gtctacgata ttggagtaga aaagatcat aatttttgc tgaagaatgg gctggtggcc       120
tctaactgct tcaacggtgg aggcggtagc atggccaatt ttaacgttcc gaaactgggt     180 gttttttccgg ttgcagcagt ttttgatatt gataatgttc cggaagatag cagcgcaacc    240
ggtagccgtt ggctgccgag catttatcaa ggtggtaatt attggggtgg tggtccgcag    300
gcactgcatg cacaggttag caattttgat agcagcaatc gtctgccgta taatccgcgt    360
accgaaaata tccggcagg taattgtgca tttgcgttta atccgtttgg tcagtatatt     420
agcaatatca gcagcgcaca gagcgttcat cgtcgtattt atggtattga tctgaatgat   480
gaaccgctgt ttagcccgaa tgcagcaagc attaccaatg gtggcaatcc gaccatgagc    540
caggataccg ttatcataa tattggtccg attaacaccg cctataaagc cgaaattttt    600
cgtccggtta atccgctgcc gatgagcgat accgcaccgg atcctgaaac actggaaccg    660
ggtcagaccg aaccgctgat taaaagtgat ggtgttata gcaatagcgg cattgccagc    720
tttatctttg atcgtccggt gacagaaccg aatccgaatt ggcctccgct gcctccgcct   780
gttattccga ttatctatcc gacaccggca ttaggtattg gtgcagcagc agcatatggt    840
```

```
tttggttatc aggttaccgt ttatcgctgg aagaaattc cggttgaatt tattgcagat    900
ccggaaacct gtccggcaca gccgaccacc gataaagtta ttattcgtac caccgatctg    960
aatccggaag gtagcccgtg tgcatatgaa gcaggtatta ttctggttcg tcagaccagc    1020
aatccgatga atgcagttgc aggtcgtctg gttccgtatg ttgaagatat tgccgttgat    1080 attttttctga ccggcaaatt ctttaccctg aatccgcctc tgcgtattac caataactat    1140
tttgcagatg acgaagtgaa agaaaacacc gttaccattg caattatac caccacactg    1200 agcagcgcat attatgcagt gtataaaacc gatggctatg gtggtgcaac ctgtttttatt    1260 gcaagcggtg gtgccggtat tagcgcactg gttcagctgc aggataatag cgttctggat    1320
gttctgtatt atagcctgcc gctgagctta ggtggtagca agcagcaat tgatgaatgg    1380 gttgcaaata actgtggtct gtttccgatg agtggtggtc tggataaaac cacactgctg    1440
gaaattccgc gtcgtcagct ggaagcaatt aatccgcagg atggtccggg tcagtatgac    1500
ctgtttattc tggatgatag cggtgcctat gcaagcttta gcagctttat tggttatccg    1560
gaagcagcct attatgttgc cggtgcagca acctttatgg atgttgaaaa tccggatgag    1620
atcatcttta ttctgcgtaa tggtgcaggt tggtatgcat gtgaaattgg tgatgcactg    1680
aaaatcgccg atgatgaatt tgatagcgtc gattattttg cctatcgtgg tggtgttatg    1740
tttattggta gcgcacgtta taccgaaggt ggtgatcctc tgccgatcaa atatcgtgca    1800
attattccgg gtctgcctcg tggtcgtctg ccacgtgttg ttctggaata tcaggcagtt    1860
ggtatgagct ttattccgtg tcagacccat tgtttaggta aggtggcat tatcagcaag    1920 gtg                                                                 1923
```

```
<210> SEQ ID NO 27
<211> LENGTH: 714
<212> TYPE: DNA
<213> ORGANISM: Artificial Sequence
<220> FEATURE:
<223> OTHER INFORMATION: T5Lys-Gp41.1N

<400> SEQUENCE: 27
```

```
atgagcttca aattcggcaa aaacagcgaa aacagctgg caaccgttaa accggaactg     60
cagaaagttg cacgtcgtgc actggaactg agcccgtatg attttaccat tgttcagggt    120
attcgtaccg ttgcacagag cgcacagaat attgcaaatg caccagctt tctgaaagat    180 ccgagcaaaa gcaaacatat taccggtgat gcaattgatt tcgcaccgta tattaacggc    240
aaaatcgatt ggaatgatct ggaagcattt gggcagtga aaaagcatt tgaacaggca    300 ggtaaagaac tgggtattaa actgcgtttt ggtgcagatt ggaacgcaag cggtgattat    360
catgatgaaa ttaaacgtgg cacctatgat ggtggtcatg ttgaactggt tggtggaggc    420
ggtagcggtt attgcctgga tctgaaaacc caggttcaga caccgcaggg tatgaaagaa    480
atttcaaata ttcaggtggg tgatctggtt ctgagcaata ccggttataa tgaagtgctg    540
aatgtgttcc cgaaaagcaa gaaaaaaagc tacaaaatca ccctggaaga tggcaaagaa    600
attatctgta gcgaagaaca cctgtttccg acacagaccg tgaaatgaa tattagcggt    660 ggtctgaaag aaggtatgtg cctgtatgtt aaagaacatc atcatcatca tcac         714
```

```
<210> SEQ ID NO 28
<211> LENGTH: 1905
<212> TYPE: DNA
<213> ORGANISM: Artificial Sequence
<220> FEATURE:
<223> OTHER INFORMATION: CfaC-T5likechee24
```

<400> SEQUENCE: 28

```
atgcatcatc atcatcatca cgtcaagatc attagtcgta agagtctggg cactcaaaac      60
gtctacgata ttggagtaga aaaagatcat aattttttgc tgaagaatgg gctggtggcc     120
tctaactgct tcaacggtgg aggcggtagc atgggtttct tgccggtaa atatagtgat      180
ggtaaaaccg ttctgagcct gaataccgaa agcggtggtg atattaatcg tcattatagc     240
ccgaatgcca acagcatttt tcatagcgat atgccgtttg ttctggttga tggcacctat     300
gaagttggtc tgggtgatgc aggtaatggt ttttttgttt gtcagatgcc tccggatatc     360
gtgaacatta aaagcaatga tccgggtcgt gttattctga ccgcaattga attaatggc      420
acccatcgtg catttctgaa tggtacacag agcaaagttg gtcagaccat tgttgcaacc     480
caggcagatc cgtttcgtag ctttgcaagc gttagccaga ccagcggttt tgcatttggt     540
aatagcctgg caagcggcac ctataactat aatccgagcc tgggtcatga agaaagcatt     600
agccgtagcg gcaccggtgg tacaaccctg catagcacct atcatggtat tgttcgtcct     660
ggtgcgggtg caccggttgg tattaccgtt gcagaagcat ttgcacagct gggttttccg     720
accaatagca gcaccgttcc gattgatggt aataatccgt attattggga tcctggttgg     780
atgagtccgc tgggtgcagc acatcgtggt catgattggt tttatgtttg caatagcaac     840
attcgcggtt atggtggtgt tcgtcagggt ctgcctggta atgttaatac catgtatcat     900
gatggtggca atcgttttgt ttgccgtggt agcaccacca atctggcaaa tcagagcggt     960
aatccgaccg ttattcagga ttggtacaat attaccccga ccaaagttat ttggtatgtg    1020
ctgaatctgc gctatagcaa tggtggtatg agcattagtg gtaatccgtt taccggtagc    1080
gatattctga ttagcccgag caactttatt atcaaaggtg ttagcctgcc gaacaccggc    1140
tataaattca ttaatcagaa cgcctttggc aacctgggtt atcgtccgga tatggaatat    1200
attggcaata atgcagcata cacggggtgtt tttggtgata ccaccgcacg ttgtgaactg    1260
gttggtagca gtaatggtgg tctgtggtca ccggttgatt atggtggcgc aaaaagccag    1320
attagcattt atcgttttgg tgtgggtaaa cagtggtatg tgaatagcaa tgataacacc    1380
attggcaatg aacatggtgt tgtttggggt ccgagcgcag ttccgctgcg tctgtttggt    1440
ggtaatgtgg gtagcagcta tatgggtgat gatattacac cgagctatcc tggtacaggt    1500
gatcgttatg ttggtctgag cacaattggc ctgggtattc ctggcggtaa tgcaaccgtg    1560
attctgacca ccgaagttat ttcaggtaat ctgaattgtg cgggtgttcc ggcaaatacc    1620
tggaataatg gtgttttttca ggttcagggt cgtcgtgcat atagctattc aggtggtgat    1680
gcaatctttc atcagattct gacactgccg gttggttatc tggttccgtt tcataccaca    1740
agcgcatttc gttataccc gaataatgca ctgagccgta atagctttat ctataccatt    1800
aagaatcttg gcaacggcaa tgttgaactg ggtgttgtta tgcatgttag tctgggtagc    1860
gcagttttc tgcctcgtct gcgtgttacc gttcagcgtc tgacc                     1905
```

<210> SEQ ID NO 29
<211> LENGTH: 425
<212> TYPE: PRT
<213> ORGANISM: Artificial Sequence
<220> FEATURE:
<223> OTHER INFORMATION: HN

<400> SEQUENCE: 29

```
Met Ala Leu Asn Asp Leu Cys Ile Lys Val Asn Asn Trp Asp Leu Phe
1               5                   10                  15
```

Phe Ser Pro Ser Glu Asp Asn Phe Thr Asn Asp Leu Asp Lys Val Glu
                20                  25                  30

Glu Ile Thr Ala Asp Thr Asn Ile Glu Ala Ala Glu Glu Asn Ile Ser
            35                  40                  45

Leu Asp Leu Ile Gln Gln Tyr Tyr Leu Thr Phe Asp Phe Asp Asn Glu
50                  55                  60

Pro Glu Asn Ile Ser Ile Glu Asn Leu Ser Ser Asp Ile Ile Gly Gln
65                  70                  75                  80

Leu Glu Pro Met Pro Asn Ile Glu Arg Phe Pro Asn Gly Lys Lys Tyr
                85                  90                  95

Glu Leu Asp Lys Tyr Thr Met Phe His Tyr Leu Arg Ala Gln Glu Phe
            100                 105                 110

Glu His Gly Asp Ser Arg Ile Ile Leu Thr Asn Ser Ala Glu Glu Ala
        115                 120                 125

Leu Leu Lys Pro Asn Val Ala Tyr Thr Phe Ser Ser Lys Tyr Val
    130                 135                 140

Lys Lys Ile Asn Lys Ala Val Glu Ala Phe Met Phe Leu Asn Trp Ala
145                 150                 155                 160

Glu Glu Leu Val Tyr Asp Phe Thr Asp Glu Thr Asn Glu Val Thr Thr
                165                 170                 175

Met Asp Lys Ile Ala Asp Ile Thr Ile Val Pro Tyr Ile Gly Pro
            180                 185                 190

Ala Leu Asn Ile Gly Asn Met Leu Ser Lys Gly Glu Phe Val Glu Ala
        195                 200                 205

Ile Ile Phe Thr Gly Val Val Ala Met Leu Glu Phe Ile Pro Glu Tyr
    210                 215                 220

Ala Leu Pro Val Phe Gly Thr Phe Ala Ile Val Ser Tyr Ile Ala Asn
225                 230                 235                 240

Lys Val Leu Thr Val Gln Thr Ile Asn Asn Ala Leu Ser Lys Arg Asn
                245                 250                 255

Glu Lys Trp Asp Glu Val Tyr Lys Tyr Thr Val Thr Asn Trp Leu Ala
            260                 265                 270

Lys Val Asn Thr Gln Ile Asp Leu Ile Arg Glu Lys Met Lys Lys Ala
        275                 280                 285

Leu Glu Asn Gln Ala Glu Ala Thr Lys Ala Ile Ile Asn Tyr Gln Tyr
    290                 295                 300

Asn Gln Tyr Thr Glu Glu Glu Lys Asn Asn Ile Asn Phe Asn Ile Asp
305                 310                 315                 320

Asp Leu Ser Ser Lys Leu Asn Glu Ser Ile Asn Ser Ala Met Ile Asn
                325                 330                 335

Ile Asn Lys Phe Leu Asp Gln Cys Ser Val Ser Tyr Leu Met Asn Ser
            340                 345                 350

Met Ile Pro Tyr Ala Val Lys Arg Leu Lys Asp Phe Asp Ala Ser Val
        355                 360                 365

Arg Asp Val Leu Leu Lys Tyr Ile Tyr Asp Asn Arg Gly Thr Leu Val
    370                 375                 380

Leu Gln Val Asp Arg Leu Lys Asp Glu Val Asn Asn Thr Leu Ser Ala
385                 390                 395                 400

Asp Ile Pro Phe Gln Leu Ser Lys Tyr Val Asp Asn Lys Lys Leu Leu
                405                 410                 415

Ser Thr Phe Thr Glu Tyr Ile Lys Asn
            420                 425

<210> SEQ ID NO 30
<211> LENGTH: 438
<212> TYPE: PRT
<213> ORGANISM: Artificial Sequence
<220> FEATURE:
<223> OTHER INFORMATION: iLC

<400> SEQUENCE: 30

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Val Ala Ser Thr Leu Asn Lys Ala Lys Ser Ile Ile
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Asn Phe Phe Lys Val Ile Asn Ala Lys Thr Phe Leu Asn
        355                 360                 365
```

-continued

```
Phe Asp Lys Ala Val Phe Arg Ile Asn Ile Val Pro Asp Glu Asn Tyr
    370                 375                 380

Thr Ile Lys Asp Gly Phe Asn Leu Lys Gly Ala Asn Leu Ser Thr Asn
385                 390                 395                 400

Phe Asn Gly Gln Asn Thr Glu Ile Asn Ser Arg Asn Phe Thr Arg Leu
                405                 410                 415

Lys Asn Phe Thr Gly Leu Phe Glu Phe Tyr Lys Leu Leu Cys Val Arg
            420                 425                 430

Gly Ile Ile Pro Phe Lys
            435

<210> SEQ ID NO 31
<211> LENGTH: 869
<212> TYPE: PRT
<213> ORGANISM: Artificial Sequence
<220> FEATURE:
<223> OTHER INFORMATION: iLCHN

<400> SEQUENCE: 31

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285
```

```
Lys Phe Lys Asp Val Ala Ser Thr Leu Asn Lys Ala Lys Ser Ile Ile
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Asn Phe Phe Lys Val Ile Asn Ala Lys Thr Phe Leu Asn
            355                 360                 365

Phe Asp Lys Ala Val Phe Arg Ile Asn Ile Val Pro Asp Glu Asn Tyr
370                 375                 380

Thr Ile Lys Asp Gly Phe Asn Leu Lys Gly Ala Asn Leu Ser Thr Asn
385                 390                 395                 400

Phe Asn Gly Gln Asn Thr Glu Ile Asn Ser Arg Asn Phe Thr Arg Leu
                405                 410                 415

Lys Asn Phe Thr Gly Leu Phe Glu Phe Tyr Lys Leu Leu Cys Val Arg
                420                 425                 430

Gly Ile Ile Pro Phe Lys Glu Asn Leu Tyr Phe Gln Gly Ala Leu Asn
                435                 440                 445

Asp Leu Cys Ile Lys Val Asn Asn Trp Asp Leu Phe Phe Ser Pro Ser
450                 455                 460

Glu Asp Asn Phe Thr Asn Asp Leu Asp Lys Val Glu Ile Thr Ala
465                 470                 475                 480

Asp Thr Asn Ile Glu Ala Ala Glu Glu Asn Ile Ser Leu Asp Leu Ile
                485                 490                 495

Gln Gln Tyr Tyr Leu Thr Phe Asp Phe Asp Asn Glu Pro Glu Asn Ile
                500                 505                 510

Ser Ile Glu Asn Leu Ser Ser Asp Ile Ile Gly Gln Leu Glu Pro Met
                515                 520                 525

Pro Asn Ile Glu Arg Phe Pro Asn Gly Lys Lys Tyr Glu Leu Asp Lys
530                 535                 540

Tyr Thr Met Phe His Tyr Leu Arg Ala Gln Glu Phe Glu His Gly Asp
545                 550                 555                 560

Ser Arg Ile Ile Leu Thr Asn Ser Ala Glu Glu Ala Leu Leu Lys Pro
                565                 570                 575

Asn Val Ala Tyr Thr Phe Ser Ser Lys Tyr Val Lys Lys Ile Asn
                580                 585                 590

Lys Ala Val Glu Ala Phe Met Phe Leu Asn Trp Ala Glu Glu Leu Val
                595                 600                 605

Tyr Asp Phe Thr Asp Glu Thr Asn Glu Val Thr Thr Met Asp Lys Ile
610                 615                 620

Ala Asp Ile Thr Ile Ile Val Pro Tyr Ile Gly Pro Ala Leu Asn Ile
625                 630                 635                 640

Gly Asn Met Leu Ser Lys Gly Glu Phe Val Gly Ala Ile Ile Phe Thr
                645                 650                 655

Gly Val Val Ala Met Leu Glu Phe Ile Pro Glu Tyr Ala Leu Pro Val
                660                 665                 670

Phe Gly Thr Phe Ala Ile Val Ser Tyr Ile Ala Asn Lys Val Leu Thr
                675                 680                 685

Val Gln Thr Ile Asn Asn Ala Leu Ser Lys Arg Asn Glu Lys Trp Asp
690                 695                 700

Glu Val Tyr Lys Tyr Thr Val Thr Asn Trp Leu Ala Lys Val Asn Thr
```

```
                705                 710                 715                 720
        Gln Ile Asp Leu Ile Arg Glu Lys Met Lys Lys Ala Leu Glu Asn Gln
                        725                 730                 735

Ala Glu Ala Thr Lys Ala Ile Ile Asn Tyr Gln Tyr Asn Gln Tyr Thr
                        740                 745                 750

Glu Glu Glu Lys Asn Asn Ile Asn Phe Asn Ile Asp Leu Ser Ser
                        755                 760                 765

Lys Leu Asn Glu Ser Ile Asn Ser Ala Met Ile Asn Ile Asn Lys Phe
                        770                 775                 780

Leu Asp Gln Cys Ser Val Ser Tyr Leu Met Asn Ser Met Ile Pro Tyr
        785                 790                 795                 800

Ala Val Lys Arg Leu Lys Asp Phe Asp Ala Ser Val Arg Asp Val Leu
                        805                 810                 815

Leu Lys Tyr Ile Tyr Asp Asn Arg Gly Thr Leu Val Leu Gln Val Asp
                        820                 825                 830

Arg Leu Lys Asp Glu Val Asn Asn Thr Leu Ser Ala Asp Ile Pro Phe
                        835                 840                 845

Gln Leu Ser Lys Tyr Val Asp Asn Lys Lys Leu Leu Ser Thr Phe Thr
                        850                 855                 860

Glu Tyr Ile Lys Asn
        865

<210> SEQ ID NO 32
<211> LENGTH: 116
<212> TYPE: PRT
<213> ORGANISM: Artificial Sequence
<220> FEATURE:
<223> OTHER INFORMATION: Spy001 Catcher

<400> SEQUENCE: 32

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
                20                  25                  30

Ser Lys Arg Asp Glu Asp Gly Lys Glu Leu Ala Gly Ala Thr Met Glu
            35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
                100                 105                 110

Asp Ala His Ile
        115

<210> SEQ ID NO 33
<211> LENGTH: 13
<212> TYPE: PRT
<213> ORGANISM: Artificial Sequence
<220> FEATURE:
<223> OTHER INFORMATION: Spy001 Tag

<400> SEQUENCE: 33

Ala His Ile Val Met Val Asp Ala Tyr Lys Pro Thr Lys
1               5                   10
```

```
<210> SEQ ID NO 34
<211> LENGTH: 120
<212> TYPE: PRT
<213> ORGANISM: Artificial Sequence
<220> FEATURE:
<223> OTHER INFORMATION: Spy002 Catcher

<400> SEQUENCE: 34

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
            20                  25                  30

Lys Arg Asp Glu Asp Gly Arg Glu Leu Ala Gly Ala Thr Met Glu Leu
        35                  40                  45

Arg Asp Ser Ser Gly Lys Thr Ile Ser Thr Trp Ile Ser Asp Gly His
    50                  55                  60

Val Lys Asp Phe Tyr Leu Tyr Pro Gly Lys Tyr Thr Phe Val Glu Thr
65                  70                  75                  80

Ala Ala Pro Asp Gly Tyr Glu Val Ala Thr Ala Ile Thr Phe Thr Val
                85                  90                  95

Asn Glu Gln Gly Gln Val Thr Val Asn Gly Glu Ala Thr Lys Gly Asp
            100                 105                 110

Ala His Thr Gly Ser Ser Gly Ser
        115                 120

<210> SEQ ID NO 35
<211> LENGTH: 14
<212> TYPE: PRT
<213> ORGANISM: Artificial Sequence
<220> FEATURE:
<223> OTHER INFORMATION: Spy002 Tag

<400> SEQUENCE: 35

Val Pro Thr Ile Val Met Val Asp Ala Tyr Lys Arg Tyr Lys
1               5                   10

<210> SEQ ID NO 36
<211> LENGTH: 113
<212> TYPE: PRT
<213> ORGANISM: Artificial Sequence
<220> FEATURE:
<223> OTHER INFORMATION: Spy003 Catcher

<400> SEQUENCE: 36

Val Thr Thr Leu Ser Gly Leu Ser Gly Glu Gln Gly Pro Ser Gly Asp
1               5                   10                  15

Met Thr Thr Glu Glu Asp Ser Ala Thr His Ile Lys Phe Ser Lys Arg
            20                  25                  30

Asp Glu Asp Gly Arg Glu Leu Ala Gly Ala Thr Met Glu Leu Arg Asp
        35                  40                  45

Ser Ser Gly Lys Thr Ile Ser Thr Trp Ile Ser Asp Gly His Val Lys
    50                  55                  60

Asp Phe Tyr Leu Tyr Pro Gly Lys Tyr Thr Phe Val Glu Thr Ala Ala
65                  70                  75                  80

Pro Asp Gly Tyr Glu Val Ala Thr Pro Ile Glu Phe Thr Val Asn Glu
                85                  90                  95

Asp Gly Gln Val Thr Val Asp Gly Glu Ala Thr Glu Gly Asp Ala His
            100                 105                 110

Thr
```

<210> SEQ ID NO 37
<211> LENGTH: 425
<212> TYPE: PRT
<213> ORGANISM: Artificial Sequence
<220> FEATURE:
<223> OTHER INFORMATION: Spy003 Tag

<400> SEQUENCE: 37

```
Met Ala Leu Asn Asp Leu Cys Ile Lys Val Asn Asn Trp Asp Leu Phe
1               5                   10                  15

Phe Ser Pro Ser Glu Asp Asn Phe Thr Asn Asp Leu Asp Lys Val Glu
            20                  25                  30

Glu Ile Thr Ala Asp Thr Asn Ile Glu Ala Ala Glu Glu Asn Ile Ser
        35                  40                  45

Leu Asp Leu Ile Gln Gln Tyr Tyr Leu Thr Phe Asp Phe Asp Asn Glu
    50                  55                  60

Pro Glu Asn Ile Ser Ile Glu Asn Leu Ser Ser Asp Ile Ile Gly Gln
65                  70                  75                  80

Leu Glu Pro Met Pro Asn Ile Glu Arg Phe Pro Asn Gly Lys Lys Tyr
                85                  90                  95

Glu Leu Asp Lys Tyr Thr Met Phe His Tyr Leu Arg Ala Gln Glu Phe
            100                 105                 110

Glu His Gly Asp Ser Arg Ile Ile Leu Thr Asn Ser Ala Glu Glu Ala
        115                 120                 125

Leu Leu Lys Pro Asn Val Ala Tyr Thr Phe Phe Ser Ser Lys Tyr Val
    130                 135                 140

Lys Lys Ile Asn Lys Ala Val Glu Ala Phe Met Phe Leu Asn Trp Ala
145                 150                 155                 160

Glu Glu Leu Val Tyr Asp Phe Thr Asp Glu Thr Asn Glu Val Thr Thr
                165                 170                 175

Met Asp Lys Ile Ala Asp Ile Thr Ile Val Pro Tyr Ile Gly Pro
            180                 185                 190

Ala Leu Asn Ile Gly Asn Met Leu Ser Lys Gly Glu Phe Val Glu Ala
        195                 200                 205

Ile Ile Phe Thr Gly Val Val Ala Met Leu Glu Phe Ile Pro Glu Tyr
    210                 215                 220

Ala Leu Pro Val Phe Gly Thr Phe Ala Ile Val Ser Tyr Ile Ala Asn
225                 230                 235                 240

Lys Val Leu Thr Val Gln Thr Ile Asn Asn Ala Leu Ser Lys Arg Asn
                245                 250                 255

Glu Lys Trp Asp Glu Val Tyr Lys Tyr Thr Val Thr Asn Trp Leu Ala
            260                 265                 270

Lys Val Asn Thr Gln Ile Asp Leu Ile Arg Glu Lys Met Lys Lys Ala
        275                 280                 285

Leu Glu Asn Gln Ala Glu Ala Thr Lys Ala Ile Ile Asn Tyr Gln Tyr
    290                 295                 300

Asn Gln Tyr Thr Glu Glu Glu Lys Asn Asn Ile Asn Phe Asn Ile Asp
305                 310                 315                 320

Asp Leu Ser Ser Lys Leu Asn Glu Ser Ile Asn Ser Ala Met Ile Asn
                325                 330                 335

Ile Asn Lys Phe Leu Asp Gln Cys Ser Val Ser Tyr Leu Met Asn Ser
            340                 345                 350

Met Ile Pro Tyr Ala Val Lys Arg Leu Lys Asp Phe Asp Ala Ser Val
        355                 360                 365
```

```
Arg Asp Val Leu Leu Lys Tyr Ile Tyr Asp Asn Arg Gly Thr Leu Val
    370                 375                 380

Leu Gln Val Asp Arg Leu Lys Asp Glu Val Asn Asn Thr Leu Ser Ala
385                 390                 395                 400

Asp Ile Pro Phe Gln Leu Ser Lys Tyr Val Asp Asn Lys Lys Leu Leu
                405                 410                 415

Ser Thr Phe Thr Glu Tyr Ile Lys Asn
            420                 425

<210> SEQ ID NO 38
<211> LENGTH: 416
<212> TYPE: PRT
<213> ORGANISM: Artificial Sequence
<220> FEATURE:
<223> OTHER INFORMATION: HN

<400> SEQUENCE: 38

Thr Leu Asp Cys Arg Glu Leu Val Lys Asn Thr Asp Leu Pro Phe
1               5                   10                  15

Ile Gly Asp Ile Ser Asp Val Lys Thr Asp Ile Phe Leu Arg Lys Asp
                20                  25                  30

Ile Asn Glu Glu Thr Glu Val Ile Tyr Tyr Pro Asp Asn Val Ser Val
            35                  40                  45

Asp Gln Val Ile Leu Ser Lys Asn Thr Ser Glu His Gly Gln Leu Asp
50                  55                  60

Leu Leu Tyr Pro Ser Ile Asp Ser Glu Ser Glu Ile Leu Pro Gly Glu
65                  70                  75                  80

Asn Gln Val Phe Tyr Asp Asn Arg Thr Gln Asn Val Asp Tyr Leu Asn
                85                  90                  95

Ser Tyr Tyr Tyr Leu Glu Ser Gln Lys Leu Ser Asp Asn Val Glu Asp
            100                 105                 110

Phe Thr Phe Thr Arg Ser Ile Glu Glu Ala Leu Asp Asn Ser Ala Lys
            115                 120                 125

Val Tyr Thr Tyr Phe Pro Thr Leu Ala Asn Lys Val Asn Ala Gly Val
        130                 135                 140

Gln Gly Gly Leu Phe Leu Met Trp Ala Asn Asp Val Val Glu Asp Phe
145                 150                 155                 160

Thr Thr Asn Ile Leu Arg Lys Asp Thr Leu Asp Lys Ile Ser Asp Val
                165                 170                 175

Ser Ala Ile Ile Pro Tyr Ile Gly Pro Ala Leu Asn Ile Ser Asn Ser
            180                 185                 190

Val Arg Arg Gly Asn Phe Thr Glu Ala Phe Ala Val Thr Gly Val Thr
        195                 200                 205

Ile Leu Leu Glu Ala Phe Pro Glu Phe Thr Ile Pro Ala Leu Gly Ala
    210                 215                 220

Phe Val Ile Tyr Ser Lys Val Gln Glu Arg Asn Glu Ile Ile Lys Thr
225                 230                 235                 240

Ile Asp Asn Cys Leu Glu Gln Arg Ile Lys Arg Trp Lys Asp Ser Tyr
                245                 250                 255

Glu Trp Met Met Gly Thr Trp Leu Ser Arg Ile Ile Thr Gln Phe Asn
            260                 265                 270

Asn Ile Ser Tyr Gln Met Tyr Asp Ser Leu Asn Tyr Gln Ala Gly Ala
        275                 280                 285

Ile Lys Ala Lys Ile Asp Leu Glu Tyr Lys Lys Tyr Ser Gly Ser Asp
    290                 295                 300
```

```
Lys Glu Asn Ile Lys Ser Gln Val Glu Asn Leu Lys Asn Ser Leu Asp
305                 310                 315                 320

Val Lys Ile Ser Glu Ala Met Asn Asn Ile Asn Lys Phe Ile Arg Glu
            325                 330                 335

Cys Ser Val Thr Tyr Leu Phe Lys Asn Met Leu Pro Lys Val Ile Asp
            340                 345                 350

Glu Leu Asn Glu Phe Asp Arg Asn Thr Lys Ala Lys Leu Ile Asn Leu
            355                 360                 365

Ile Asp Ser His Asn Ile Ile Leu Val Gly Glu Val Asp Lys Leu Lys
    370                 375                 380

Ala Lys Val Asn Asn Ser Phe Gln Asn Thr Ile Pro Phe Asn Ile Phe
385                 390                 395                 400

Ser Tyr Thr Asn Asn Ser Leu Leu Lys Asp Ile Ile Asn Glu Tyr Phe
                405                 410                 415

<210> SEQ ID NO 39
<211> LENGTH: 421
<212> TYPE: PRT
<213> ORGANISM: Artificial Sequence
<220> FEATURE:
<223> OTHER INFORMATION: HN

<400> SEQUENCE: 39

Lys Ser Ile Cys Ile Glu Ile Asn Asn Gly Glu Leu Phe Phe Val Ala
1               5                   10                  15

Ser Glu Asn Ser Tyr Asn Asp Asp Ile Asn Thr Pro Lys Glu Ile
            20                  25                  30

Asp Asp Thr Val Thr Ser Asn Asn Tyr Glu Asn Asp Leu Asp Gln
            35                  40                  45

Val Ile Leu Asn Phe Asn Ser Glu Ser Ala Pro Gly Leu Ser Asp Glu
50                  55                  60

Lys Leu Asn Leu Thr Ile Gln Asn Asp Ala Tyr Ile Pro Lys Tyr Asp
65                  70                  75                  80

Ser Asn Gly Thr Ser Asp Ile Glu Gln His Asp Val Asn Glu Leu Asn
            85                  90                  95

Val Phe Phe Tyr Leu Asp Ala Gln Lys Val Pro Glu Gly Glu Asn Asn
            100                 105                 110

Val Asn Leu Thr Ser Ser Ile Asp Thr Ala Leu Leu Glu Gln Pro Lys
            115                 120                 125

Ile Tyr Thr Phe Phe Ser Ser Glu Phe Ile Asn Asn Val Asn Lys Pro
    130                 135                 140

Val Gln Ala Ala Leu Phe Val Ser Trp Ile Gln Gln Val Leu Val Asp
145                 150                 155                 160

Phe Thr Thr Glu Ala Asn Gln Lys Ser Thr Val Asp Lys Ile Ala Asp
                165                 170                 175

Ile Ser Ile Val Val Pro Tyr Ile Gly Leu Ala Leu Asn Ile Gly Asn
            180                 185                 190

Glu Ala Gln Lys Gly Asn Phe Lys Asp Ala Leu Glu Leu Leu Gly Ala
            195                 200                 205

Gly Ile Leu Leu Glu Phe Glu Pro Glu Leu Leu Ile Pro Thr Ile Leu
    210                 215                 220

Val Phe Thr Ile Lys Ser Phe Leu Gly Ser Ser Asp Asn Lys Asn Lys
225                 230                 235                 240

Val Ile Lys Ala Ile Asn Asn Ala Leu Lys Glu Arg Asp Glu Lys Trp
                245                 250                 255
```

Lys Glu Val Tyr Ser Phe Ile Val Ser Asn Trp Met Thr Lys Ile Asn
            260                 265                 270

Thr Gln Phe Asn Lys Arg Lys Glu Gln Met Tyr Gln Ala Leu Gln Asn
        275                 280                 285

Gln Val Asn Ala Ile Lys Thr Ile Ile Glu Ser Lys Tyr Asn Ser Tyr
    290                 295                 300

Thr Leu Glu Glu Lys Asn Glu Leu Thr Asn Lys Tyr Asp Ile Lys Gln
305                 310                 315                 320

Ile Glu Asn Glu Leu Asn Gln Lys Val Ser Ile Ala Met Asn Asn Ile
            325                 330                 335

Asp Arg Phe Leu Thr Glu Ser Ser Ile Ser Tyr Leu Met Lys Ile Ile
            340                 345                 350

Asn Glu Val Lys Ile Asn Lys Leu Arg Glu Tyr Asp Glu Asn Val Lys
            355                 360                 365

Thr Tyr Leu Leu Asn Tyr Ile Ile Gln His Gly Ser Ile Leu Gly Glu
        370                 375                 380

Ser Gln Gln Glu Leu Asn Ser Met Val Thr Asp Thr Leu Asn Asn Ser
385                 390                 395                 400

Ile Pro Phe Lys Leu Ser Ser Tyr Thr Asp Asp Lys Ile Leu Ile Ser
            405                 410                 415

Tyr Phe Asn Lys Phe
            420

<210> SEQ ID NO 40
<211> LENGTH: 449
<212> TYPE: PRT
<213> ORGANISM: Artificial Sequence
<220> FEATURE:
<223> OTHER INFORMATION: iLC

<400> SEQUENCE: 40

Pro Ile Thr Ile Asn Asn Phe Asn Tyr Ser Asp Pro Val Asp Asn Lys
1               5                   10                  15

Asn Ile Leu Tyr Leu Asp Thr His Leu Asn Thr Leu Ala Asn Glu Pro
            20                  25                  30

Glu Lys Ala Phe Arg Ile Thr Gly Asn Ile Trp Val Ile Pro Asp Arg
        35                  40                  45

Phe Ser Arg Asn Ser Asn Pro Asn Leu Asn Lys Pro Pro Arg Val Thr
    50                  55                  60

Ser Pro Lys Ser Gly Tyr Tyr Asp Pro Asn Tyr Leu Ser Thr Asp Ser
65                  70                  75                  80

Asp Lys Asp Pro Phe Leu Lys Glu Ile Ile Lys Leu Phe Lys Arg Ile
                85                  90                  95

Asn Ser Arg Glu Ile Gly Glu Glu Leu Ile Tyr Arg Leu Ser Thr Asp
            100                 105                 110

Ile Pro Phe Pro Gly Asn Asn Asn Thr Pro Ile Asn Thr Phe Asp Phe
        115                 120                 125

Asp Val Asp Phe Asn Ser Val Asp Val Lys Thr Arg Gln Gly Asn Asn
130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                165                 170                 175

Asn Thr Phe Ala Ala Gln Glu Gly Phe Gly Ala Leu Ser Ile Ile Ser
            180                 185                 190

Ile Ser Pro Arg Phe Met Leu Thr Tyr Ser Asn Ala Thr Asn Asp Val
        195                 200                 205

Gly Glu Gly Arg Phe Ser Lys Ser Glu Phe Cys Met Asp Pro Ile Leu
210                 215                 220

Ile Leu Met His Glu Leu Asn His Ala Met His Asn Leu Tyr Gly Ile
225                 230                 235                 240

Ala Ile Pro Asn Asp Gln Thr Ile Ser Ser Val Thr Ser Asn Ile Phe
        245                 250                 255

Tyr Ser Gln Tyr Asn Val Lys Leu Glu Tyr Ala Glu Ile Tyr Ala Phe
        260                 265                 270

Gly Gly Pro Thr Ile Asp Leu Ile Pro Lys Ser Ala Arg Lys Tyr Phe
        275                 280                 285

Glu Glu Lys Ala Leu Asp Tyr Tyr Arg Ser Ile Ala Lys Arg Leu Asn
290                 295                 300

Ser Ile Thr Thr Ala Asn Pro Ser Ser Phe Asn Lys Tyr Ile Gly Glu
305                 310                 315                 320

Tyr Lys Gln Lys Leu Ile Arg Lys Tyr Arg Phe Val Val Glu Ser Ser
            325                 330                 335

Gly Glu Val Thr Val Asn Arg Asn Lys Phe Val Glu Leu Tyr Asn Glu
            340                 345                 350

Leu Thr Gln Ile Phe Thr Glu Phe Asn Tyr Ala Lys Ile Tyr Asn Val
        355                 360                 365

Gln Asn Arg Lys Ile Tyr Leu Ser Asn Val Tyr Thr Pro Val Thr Ala
        370                 375                 380

Asn Ile Leu Asp Asp Asn Val Tyr Asp Ile Gln Asn Gly Phe Asn Ile
385                 390                 395                 400

Pro Lys Ser Asn Leu Asn Val Leu Phe Met Gly Gln Asn Leu Ser Arg
            405                 410                 415

Asn Pro Ala Leu Arg Lys Val Asn Pro Glu Asn Met Leu Tyr Leu Phe
            420                 425                 430

Thr Lys Phe Cys His Lys Ala Ile Asp Gly Gln Ser Leu Asp Gln Gly
            435                 440                 445

Gly

<210> SEQ ID NO 41
<211> LENGTH: 412
<212> TYPE: PRT
<213> ORGANISM: Artificial Sequence
<220> FEATURE:
<223> OTHER INFORMATION: iLC

<400> SEQUENCE: 41

Pro Lys Ile Asn Ser Phe Asn Tyr Asn Asp Pro Val Asn Asp Arg Thr
1               5                   10                  15

Ile Leu Tyr Ile Lys Pro Gly Gly Cys Gln Glu Phe Tyr Lys Ser Phe
            20                  25                  30

Asn Ile Met Lys Asn Ile Trp Ile Ile Pro Glu Arg Asn Val Ile Gly
        35                  40                  45

Thr Thr Pro Gln Asp Phe His Pro Thr Ser Leu Lys Asn Gly Asp
    50                  55                  60

Ser Ser Tyr Tyr Asp Pro Asn Tyr Leu Gln Ser Asp Glu Glu Lys Asp
65                  70                  75                  80

Arg Phe Leu Lys Ile Val Thr Lys Ile Phe Asn Arg Ile Asn Asn Asn
                85                  90                  95

Leu Ser Gly Gly Ile Leu Leu Glu Glu Leu Ser Lys Ala Asn Pro Tyr
            100                 105                 110

Leu Gly Asn Asp Asn Thr Pro Asp Asn Gln Phe His Ile Gly Asp Ala
        115                 120                 125

Ser Ala Val Glu Ile Lys Phe Ser Asn Gly Ser Gln Asp Ile Leu Leu
    130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Arg
            165                 170                 175

Phe Gly Ser Ile Ala Ile Val Thr Phe Ser Pro Glu Tyr Ser Phe Arg
        180                 185                 190

Phe Asn Asp Asn Cys Met Asn Glu Phe Ile Gln Asp Pro Ala Leu Thr
    195                 200                 205

Leu Met His Gln Leu Ile His Ser Leu His Gly Leu Tyr Gly Ala Lys
210                 215                 220

Gly Ile Thr Thr Lys Tyr Thr Ile Thr Gln Lys Gln Asn Pro Leu Ile
225                 230                 235                 240

Thr Asn Ile Arg Gly Thr Asn Ile Glu Glu Phe Leu Thr Phe Gly Gly
            245                 250                 255

Thr Asp Leu Asn Ile Ile Thr Ser Ala Gln Ser Asn Asp Ile Tyr Thr
        260                 265                 270

Asn Leu Leu Ala Asp Tyr Lys Lys Ile Ala Ser Lys Leu Ser Lys Val
    275                 280                 285

Gln Val Ser Asn Pro Leu Leu Asn Pro Tyr Lys Asp Val Phe Glu Ala
290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Gln Phe
            325                 330                 335

Asp Leu Arg Thr Lys Phe Gln Val Lys Cys Arg Gln Thr Tyr Ile Gly
        340                 345                 350

Gln Tyr Lys Tyr Phe Lys Leu Ser Asn Leu Leu Asn Asp Ser Ile Tyr
    355                 360                 365

Asn Ile Ser Glu Gly Tyr Asn Ile Asn Asn Leu Lys Val Asn Phe Arg
370                 375                 380

Gly Gln Asn Ala Asn Leu Asn Pro Arg Ile Ile Thr Pro Ile Thr Gly
385                 390                 395                 400

Arg Gly Leu Val Lys Lys Ile Ile Arg Phe Cys Lys
            405                 410

<210> SEQ ID NO 42
<211> LENGTH: 1033
<212> TYPE: PRT
<213> ORGANISM: Artificial Sequence
<220> FEATURE:
<223> OTHER INFORMATION: Gp41.1C-iLCHN-SpyC003

<400> SEQUENCE: 42

Met His His His His His Met Met Leu Lys Lys Ile Leu Lys Ile
1               5                   10                  15

Glu Glu Leu Asp Glu Arg Glu Leu Ile Asp Ile Glu Val Ser Gly Asn
                20                  25                  30

His Leu Phe Tyr Ala Asn Asp Ile Leu Thr His Asn Ser Ser Ser Pro
        35                  40                  45

```
Phe Val Asn Lys Gln Phe Asn Tyr Lys Asp Pro Val Asn Gly Val Asp
    50                  55                  60

Ile Ala Tyr Ile Lys Ile Pro Asn Ala Gly Gln Met Gln Pro Val Lys
65                  70                  75                  80

Ala Phe Lys Ile His Asn Lys Ile Trp Val Ile Pro Glu Arg Asp Thr
                85                  90                  95

Phe Thr Asn Pro Glu Glu Gly Asp Leu Asn Pro Pro Glu Ala Lys
            100                 105                 110

Gln Val Pro Val Ser Tyr Tyr Asp Ser Thr Tyr Leu Ser Thr Asp Asn
                115                 120                 125

Glu Lys Asp Asn Tyr Leu Lys Gly Val Thr Lys Leu Phe Glu Arg Ile
130                 135                 140

Tyr Ser Thr Asp Leu Gly Arg Met Leu Leu Thr Ser Ile Val Arg Gly
145                 150                 155                 160

Ile Pro Phe Trp Gly Gly Ser Thr Ile Asp Thr Glu Leu Lys Val Ile
                165                 170                 175

Asp Thr Asn Cys Ile Asn Val Ile Gln Pro Asp Gly Ser Tyr Arg Ser
                180                 185                 190

Glu Glu Leu Asn Leu Val Ile Ile Gly Pro Ser Ala Asp Ile Ile Gln
            195                 200                 205

Phe Glu Cys Lys Ser Phe Gly His Asp Val Leu Asn Leu Thr Arg Asn
            210                 215                 220

Gly Tyr Gly Ser Thr Gln Tyr Ile Arg Phe Ser Pro Asp Phe Thr Phe
225                 230                 235                 240

Gly Phe Glu Glu Ser Leu Glu Val Asp Thr Asn Pro Leu Leu Gly Ala
                245                 250                 255

Gly Lys Phe Ala Thr Asp Pro Ala Val Thr Leu Ala His Glu Leu Ile
                260                 265                 270

His Ala Glu His Arg Leu Tyr Gly Ile Ala Ile Asn Pro Asn Arg Val
            275                 280                 285

Phe Lys Val Asn Thr Asn Ala Tyr Tyr Glu Met Ser Gly Leu Glu Val
            290                 295                 300

Ser Phe Glu Glu Leu Arg Thr Phe Gly Gly His Asp Ala Lys Phe Ile
305                 310                 315                 320

Asp Ser Leu Gln Glu Asn Glu Phe Arg Leu Tyr Tyr Tyr Asn Lys Phe
                325                 330                 335

Lys Asp Val Ala Ser Thr Leu Asn Lys Ala Lys Ser Ile Ile Gly Thr
                340                 345                 350

Thr Ala Ser Leu Gln Tyr Met Lys Asn Val Phe Lys Glu Lys Tyr Leu
            355                 360                 365

Leu Ser Glu Asp Thr Ser Gly Lys Phe Ser Val Asp Lys Leu Lys Phe
370                 375                 380

Asp Lys Leu Tyr Lys Met Leu Thr Glu Ile Tyr Thr Glu Asp Asn Phe
385                 390                 395                 400

Val Asn Phe Phe Lys Val Ile Asn Ala Lys Thr Phe Leu Asn Phe Asp
                405                 410                 415

Lys Ala Val Phe Arg Ile Asn Ile Val Pro Asp Glu Asn Tyr Thr Ile
                420                 425                 430

Lys Asp Gly Phe Asn Leu Lys Gly Ala Asn Leu Ser Thr Asn Phe Asn
                435                 440                 445

Gly Gln Asn Thr Glu Ile Asn Ser Arg Asn Phe Thr Arg Leu Lys Asn
450                 455                 460

Phe Thr Gly Leu Phe Glu Phe Tyr Lys Leu Leu Cys Val Arg Gly Ile
```

```
              465                 470                 475                 480
        Ile Pro Phe Lys Glu Asn Leu Tyr Phe Gln Gly Ala Leu Asn Asp Leu
                        485                 490                 495

Cys Ile Lys Val Asn Asn Trp Asp Leu Phe Phe Ser Pro Ser Glu Asp
                        500                 505                 510

Asn Phe Thr Asn Asp Leu Asp Lys Val Glu Glu Ile Thr Ala Asp Thr
                        515                 520                 525

Asn Ile Glu Ala Ala Glu Glu Asn Ile Ser Leu Asp Leu Ile Gln Gln
                        530                 535                 540

Tyr Tyr Leu Thr Phe Asp Phe Asp Asn Glu Pro Glu Asn Ile Ser Ile
        545                 550                 555                 560

Glu Asn Leu Ser Ser Asp Ile Ile Gly Gln Leu Glu Pro Met Pro Asn
                        565                 570                 575

Ile Glu Arg Phe Pro Asn Gly Lys Lys Tyr Glu Leu Asp Lys Tyr Thr
                        580                 585                 590

Met Phe His Tyr Leu Arg Ala Gln Glu Phe Glu His Gly Asp Ser Arg
                        595                 600                 605

Ile Ile Leu Thr Asn Ser Ala Glu Glu Ala Leu Leu Lys Pro Asn Val
                        610                 615                 620

Ala Tyr Thr Phe Phe Ser Ser Lys Tyr Val Lys Lys Ile Asn Lys Ala
        625                 630                 635                 640

Val Glu Ala Phe Met Phe Leu Asn Trp Ala Glu Glu Leu Val Tyr Asp
                        645                 650                 655

Phe Thr Asp Glu Thr Asn Glu Val Thr Thr Met Asp Lys Ile Ala Asp
                        660                 665                 670

Ile Thr Ile Ile Val Pro Tyr Ile Gly Pro Ala Leu Asn Ile Gly Asn
                        675                 680                 685

Met Leu Ser Lys Gly Glu Phe Val Glu Ala Ile Ile Phe Thr Gly Val
                        690                 695                 700

Val Ala Met Leu Glu Phe Ile Pro Glu Tyr Ala Leu Pro Val Phe Gly
        705                 710                 715                 720

Thr Phe Ala Ile Val Ser Tyr Ile Ala Asn Lys Val Leu Thr Val Gln
                        725                 730                 735

Thr Ile Asn Asn Ala Leu Ser Lys Arg Asn Glu Lys Trp Asp Glu Val
                        740                 745                 750

Tyr Lys Tyr Thr Val Thr Asn Trp Leu Ala Lys Val Asn Thr Gln Ile
                        755                 760                 765

Asp Leu Ile Arg Glu Lys Met Lys Lys Ala Leu Glu Asn Gln Ala Glu
        770                 775                 780

Ala Thr Lys Ala Ile Ile Asn Tyr Gln Tyr Asn Gln Tyr Thr Glu Glu
        785                 790                 795                 800

Glu Lys Asn Asn Ile Asn Phe Asn Ile Asp Asp Leu Ser Ser Lys Leu
                        805                 810                 815

Asn Glu Ser Ile Asn Ser Ala Met Ile Asn Ile Asn Lys Phe Leu Asp
                        820                 825                 830

Gln Cys Ser Val Ser Tyr Leu Met Asn Ser Met Ile Pro Tyr Ala Val
                        835                 840                 845

Lys Arg Leu Lys Asp Phe Asp Ala Ser Val Arg Asp Val Leu Leu Lys
                        850                 855                 860

Tyr Ile Tyr Asp Asn Arg Gly Thr Leu Val Leu Gln Val Asp Arg Leu
        865                 870                 875                 880

Lys Asp Glu Val Asn Asn Thr Leu Ser Ala Asp Ile Pro Phe Gln Leu
                        885                 890                 895
```

-continued

```
Ser Lys Tyr Val Asp Asn Lys Lys Leu Leu Ser Thr Phe Thr Glu Tyr
            900                 905                 910

Ile Lys Asn Gly Gly Gly Ser Val Thr Thr Leu Ser Gly Leu Ser
        915                 920                 925

Gly Glu Gln Gly Pro Ser Gly Asp Met Thr Thr Glu Glu Asp Ser Ala
    930                 935                 940

Thr His Ile Lys Phe Ser Lys Arg Asp Glu Asp Gly Arg Glu Leu Ala
945                 950                 955                 960

Gly Ala Thr Met Glu Leu Arg Asp Ser Ser Gly Lys Thr Ile Ser Thr
            965                 970                 975

Trp Ile Ser Asp Gly His Val Lys Asp Phe Tyr Leu Tyr Pro Gly Lys
            980                 985                 990

Tyr Thr Phe Val Glu Thr Ala Ala Pro Asp Gly Tyr Glu Val Ala Thr
        995                 1000                1005

Pro Ile Glu Phe Thr Val Asn Glu Asp Gly Gln Val Thr Val Asp
    1010                1015                1020

Gly Glu Ala Thr Glu Gly Asp Ala His Thr
1025                1030
```

PROTEIN COMPLEX INCLUDING BOTULINUM TOXIN TRANSLOCATION DOMAIN AND ENDOLYSIN AND ANTIBACTERIAL COMPOSITION INCLUDING SAME

CROSS REFERENCE TO RELATED APPLICATIONS

This application is a National Stage of International Application No. PCT/KR2022/005511 filed Apr. 18, 2022, claiming priority based on Korean Patent Application No. 10-2021-0050767 filed Apr. 19, 2021, the entire disclosures of which are incorporated herein by reference.

INCORPORATION BY REFERENCE OF SEQUENCE LISTING

The content of the electronically submitted sequence listing, file name: Q292007_sequence listing as filed.TXT; size: 82,672 bytes; and date of creation: Sep. 20, 2023, filed herewith, is incorporated herein by reference in its entirety.

TECHNICAL FIELD

The present invention relates to a protein complex including a botulinum toxin translocation domain and endolysin.

BACKGROUND ART

Infections with multidrug-resistant bacteria that are resistant to various antibiotics are causing serious medical problems in South Korea and other countries around the world. In South Korea, in accordance with the enforcement of the Infectious Disease Prevention and Control Act in December 2010, six types of antibiotic-resistant bacteria (VRSA (vancomycin-resistant *Staphylococcus aureus*), VRE (vancomycin-resistant *Enterococcus*), MRSA (methicillin-resistant *Staphylococcus aureus*), MRPA (multidrug-resistant *Pseudomonas aeruginosa*), MRAB (multidrug-resistant *Acinetobacter baumannii*), CRE (carbapenem-resistant Enterobacteriaceae) are designated and managed as surveillance targets. The U.S. Centers for Disease Control and Prevention has pointed out the seriousness of medical problems caused by hospital-derived six multidrug-resistant bacteria (*Enterococcus faecium, Staphylococcus aureus, Klebsiella pneumoniae, Acinetobacter baumannii, Pseudomonas aeruginosa,* and *Enterobacter* spp. ESKAPE) and ESBL (extended spectrum β-lactamase) strains and various multi-drug resistant bacteria such as carbapenem-resistant bacteria. Hospital-acquired infections caused by multidrug-resistant bacteria are reported to occur more frequently, especially in seriously ill patients, and treatment thereof is becoming increasingly difficult as they acquire more powerful resistance to antibiotics.

Bacteria are classified into Gram-positive and Gram-negative bacteria based on differences in Gram staining patterns depending on the cell wall structure and the cell wall structure thereof is as follows. Gram-positive bacteria consists of an inner membrane and peptidoglycan, and Gram-negative bacteria consists of an inner membrane, peptidoglycan, and an outer membrane. Thereamong, the cell outer membrane of Gram-negative bacteria is known to block various substances, including antibacterial substances, from being delivered into the cells.

Therefore, there is a need to develop antibacterial substances to effectively deliver target proteins into target strains.

DISCLOSURE

Technical Problem

The present inventors made extensive efforts to research and develop antibacterial substances to effectively deliver target proteins into target strains. As a result, the present inventors identified that the target proteins can be effectively delivered into the strains using a botulinum toxin translocation domain. Based thereon, the present invention has been completed.

Accordingly, it is one object of the present invention to provide a protein complex containing a botulinum toxin translocation domain and endolysin.

It is another object of the present invention to provide a recombinant vector containing a polynucleotide encoding the protein complex.

It is another object of the present invention to provide a host cell transformed with the recombinant vector containing the polynucleotide encoding the protein complex.

It is another object of the present invention to provide a method for producing a protein complex including mixing protein fragments and linking the mixed protein fragments.

It is another object of the present invention to provide an antibacterial composition containing the protein complex.

It is another object of the present invention to provide a method for screening a protein complex including reacting the protein complex with a target strain and determining whether or not the target strain exhibits antibacterial activity.

Technical Solution

In accordance with one aspect of the present invention, the above and other objects can be accomplished by the provision of a protein complex containing a botulinum toxin translocation domain and endolysin.

In an embodiment of the present invention, the botulinum toxin translocation domain may include at least one amino acid sequence selected from SEQ ID NOS: 29, 38, and 39.

In one embodiment of the present invention, the endolysin may be selected from the group consisting of lys, LysPA26, PB1_gp48, LysAB2_P3, PlyF307, AcLys, PlyPA03, PlyPA91, Abtn-4, WCHABP1_gp01, WCHABP12_gp19, gh-1p12, B3ORF25, phi-13Sp4, phi-6S_4, KP27_166, KP13_gp066, BI057_gp221, LPSE_00024, STP4a_120, Lys68, SPN1S_0028 and P22gp66.

In one embodiment of the present invention, the protein complex may further contain a receptor-binding protein. The receptor-binding protein may be, for example, selected from the group consisting of PRD1_04, P1301_0153, P24_0149, Pb5, AbTJ_gp52, AbTJ_gp53, phiAB6_gp40, S, A318_gp060, rv5_gp030, rv5_gp033, PaoP5_075, BH773_gp153, AU075_gp145, CPT_Sugarland_191, JIPhKp127_0170, AmPhEK80_0178, P22_gp19, DET7_207, HWD08_gp154, BI021_gp088, HWD21_gp023, HWC41_gp146, HOS12_gp017, HOU44_gp075, I133_gp019, HWC50_gp066, and HOS34_gp106.

In one embodiment of the present invention, the protein complex may contain the endolysin, the botulinum toxin translocation domain, and the receptor-binding protein disposed in this order.

In accordance with another aspect of the present invention, provided is a recombinant vector containing a polynucleotide encoding the protein complex.

In accordance with another aspect of the present invention, provided is a host cell transformed with the recombinant vector containing the polynucleotide encoding the protein complex.

In one embodiment of the present invention, the polynucleotide may include a nucleic acid sequence represented by SEQ ID NO: 21.

In accordance with another aspect of the present invention, provided is a method of preparing a protein complex including (a) mixing a first protein fragment containing a botulinum toxin translocation domain with a second protein fragment containing endolysin, and (b) linking the mixed protein fragments to each other.

In one embodiment of the present invention, the method may further include mixing a third protein fragment containing a receptor-binding protein in the step (a) of mixing the first protein fragment containing the botulinum toxin translocation domain with the second protein fragment containing endolysin.

In one embodiment of the present invention, the protein fragment may contain intein.

In one embodiment of the present invention, the step (b) of linking the protein fragments may be performed by a protein trans-splicing reaction.

In one embodiment of the present invention, the protein fragment may contain SpyTag and Spycatcher.

In accordance with another aspect of the present invention, provided is an antibacterial composition containing the protein complex.

In accordance with another aspect of the present invention, provided is a method for screening an antibacterial protein complex including reacting the protein complex with a target strain, and determining whether or not the protein complex exhibits antibacterial activity against the target strain.

Advantageous Effects

The aspects and advantages of the present invention are summarized as follows:

(a) The present invention provides a protein complex containing a botulinum toxin translocation domain and endolysin. (b) The present invention provides a recombinant vector containing a polynucleotide encoding the protein complex and a host cell transformed with the recombinant vector. (c) The present invention provides a method for producing a protein complex including mixing and linking protein fragments. (d) The present invention provides an antibacterial composition containing the protein complex. (e) The protein complex containing the botulinum toxin translocation domain and endolysin of the present invention provides an antibacterial effect and can thus be used as an antibacterial composition or antibiotic.

Further, the present invention provides a method for screening a protein complex including reacting the protein complex with a target strain and determining whether or not the protein complex exhibits antibacterial activity.

DESCRIPTION OF DRAWINGS

FIG. 1 illustrates a vector for producing full-length translysin.

FIG. 2 illustrates the result of detection of translysin by SDS gel electrophoresis.

FIG. 3 illustrates the result of detection of innolysin by SDS gel electrophoresis.

FIG. 4 shows lytic effects depending on the presence or absence of intracellular expression of translysin and innolysin, as detected from the turbidity of a culture solution.

FIG. 5 is a graph showing growth patterns depending on the presence or absence of intracellular expression of translysin, innolysin, and endolysin, as detected from turbidity of the culture medium.

A of FIG. 6 shows four protein fragments (LysPA26-Gp41.1N, PB1_gp48-Gp41.1N, Gp41.1C-iLCHN-CfaN, CfaC-PRD1_04) used to produce translysin. B of FIG. 6 shows three protein fragments (LysPA26-Gp41.1N, Gp41.1C-iLCHN-SpyC003, SpyT003-PRD1_04) used to produce translysin.

FIG. 7 shows the result of trans-splicing of PB1_gp48 and iLCH$_N$ over time.

FIG. 8 shows the result of trans-splicing of LysPA26 and iLCH$_N$ over time.

FIG. 9 shows the result of trans-splicing of iLCH$_N$ and PRD1 over time.

FIG. 10 shows the result of trans-splicing of PB1_gp48, iLCH$_N$ and PRD1 over time.

FIG. 11 shows the results of trans-splicing and bioconjugation of LysPA26, iLCH$_N$, and PRD1 over time.

FIG. 12 is a schematic diagram illustrating a method of performing a spotting assay.

FIG. 13 shows the lytic activity of the LysPA26-Gp41.1N fragment against dead cells, detected by spotting assay.

FIG. 14 shows the lytic activity of the PB1_gp48-Gp41.1N fragment against dead cells, detected by spotting assay.

FIG. 15 shows the lytic activity of translysin (LysPA26-iLCH$_N$-PRD1) and endolysin fragments against live bacteria, detected by spotting assay.

FIG. 16 shows the lytic activity of translysin (PB1_gp48-iLCH$_N$-PRD1) and endolysin fragments against live bacteria, detected by spotting assay.

FIG. 17 shows the lytic activity of translysin (PB1_gp48-iLCH$_N$-PRD1) and endolysin fragments, and innolysin against live bacteria, detected by spotting assay.

FIG. 18 shows the lytic activity of translysin (LysPA26-iLCH$_N$-PRD1) and endolysin fragments, and innolysin against live bacteria, detected by spotting assay.

FIG. 19 is an electron microscope image showing viable cells depending on the translysin treatment and time.

FIG. 20 shows the lytic activity of translysin and innolysin detected through CFU reduction assay.

FIG. 21 shows a schematic diagram illustrating screening of a translysin library against target strains.

FIG. 22 shows the lysis patterns of viable cells of target strains as a function of concentration of each translysin.

FIG. 23 is a schematic diagram illustrating the translysin structure of the present invention.

FIG. 24 is a schematic diagram illustrating the mechanism of action of translysin of the present invention.

FIG. 25 is a schematic diagram illustrating a method for synthesizing translysin using intein.

FIG. 26 is a schematic diagram illustrating a translysin synthesis method using intein and SpyTag and Spycatcher.

BEST MODE

In one aspect, the present invention is directed to a protein complex containing a botulinum toxin translocation domain and endolysin.

As used herein, the term "protein complex" may be used interchangeably with "translysin."

As used herein, the term "botulinum toxin translocation domain" refers to a protein that has the function of delivering light chains of botulinum toxin into nerve cells, and the delivery process occurs based on the mechanism in which when the botulinum toxin is introduced into the cells through endocytosis, the inside of the endosome becomes acidic, causing the translocation domain to have enzymatic activity, resulting in the process of transferring light chains from the endosome to the cytoplasm. As used herein, the term "botulinum toxin translocation domain" may also be referred to as "botulinum toxin translocation domain $H_N$", "translocation domain", "$H_N$", or the like. In the present invention, the "botulinum toxin translocation domain" serves to allow the protein complex of the present invention to pass through the cell membrane (outer cell membrane). As a result, the protein complex of the present invention can access the peptidoglycan that exists between the outer and inner cell membranes.

In one embodiment of the present invention, the botulinum toxin translocation domain may include at least one amino acid sequence selected from SEQ ID NOS: 29, 38, and 39.

As used herein, the expression that "polynucleotide" (that may be used interchangeably with "gene") or polypeptide (that may be used interchangeably with "protein") "includes a specific nucleic acid sequence or amino acid sequence" or "includes a specific nucleic acid sequence or amino acid sequence." may mean that the polynucleotide or polypeptide essentially includes the specific nucleic acid sequence or amino acid sequence, and may be interpreted as including a "substantially identical sequence" including a mutated (deleted, substituted, modified, and/or added) specific nucleic acid sequence or amino acid sequence (or not excluding the mutation) while maintaining the original function and/or desired function of the polynucleotide or polypeptide. For example, the expression that a polynucleotide or polypeptide "includes a specific nucleic acid sequence or amino acid sequence" or "includes or is represented by a specific nucleic acid sequence or amino acid sequence" means that the polynucleotide or polypeptide (i) essentially includes a sequence or amino acid sequence, or (ii) includes an amino acid sequence having an identity of at least 96%, at least 97%, at least 98%, at least 99%, at least 99.5%, or at least 99.9% to the specific nucleic acid or amino acid sequence and maintains original and/or desired functions thereof.

In one embodiment of the present invention, the protein complex may further contain a botulinum toxin light chain (LC). The addition of the botulinum toxin light chain (LC) may facilitate expression of the botulinum toxin translocation domain in a soluble form. At this time, it is preferable to use the botulinum toxin light chain in an inactivated state. According to an embodiment of the present invention, the botulinum toxin light chain may be obtained in an inactive form by modifying a zinc-binding sequence.

In one embodiment of the present invention, the inactivated botulinum toxin light chain (iLC) may include at least one selected from amino acid sequences represented by SEQ ID NOS: 30, 40, and 41 and the like.

In one embodiment of the present invention, the botulinum toxin translocation domain may be linked to the inactivated botulinum toxin light chain (iLC).

In one embodiment of the present invention, the polypeptide including the botulinum toxin translocation domain and the inactivated botulinum toxin light chain linked to each other may include an amino acid sequence of SEQ ID NO: 31.

As used herein, the term "endolysin" refers to a protein expressed in a virus that causes infection with bacteria as a host, and the endolysin exhibits the activity of lysing the cell wall of the host bacteria. Since endolysin cannot penetrate the outer cell membrane by itself, only the lytic activity of endolysin against Gram-positive bacteria is known. In addition, endolysin is not cytotoxic to eukaryotes including humans because it uses bacterial peptidoglycan as a substrate, and no cases of bacteria resistant to endolysin have been reported.

In the present invention, the protein complex of the present invention, which passes through the outer cell membrane and accesses peptidoglycan through the "botulinum toxin translocation domain" decomposes peptidoglycan through the endolysin contained therein and thus exhibits antibacterial activity.

In one embodiment of the present invention, the endolysin is selected from the group consisting of lys, LysPA26, PB1_gp48, LysAB2_P3, PlyF307, AcLys, PlyPA03, PlyPA91, Abtn-4, WCHABP1_gp01, WCHABP12_gp19, gh-1p12, B3ORF25, phi-13Sp4, phi-6S_4, KP27_166, KP13_gp066, BI057_gp221, LPSE_00024, STP4a_120, Lys68, SPN1S_0028 and P22gp66. However, any endolysin may be used in the present invention so long as it exhibit lytic activity and the endolysin is not necessarily limited to a specific type.

In one embodiment of the present invention, the protein complex may further contain a receptor-binding protein.

As used herein, the term "receptor-binding protein" refers to a structural protein involved in the process of recognizing and attaching to a specific receptor on the cell wall when a bacteriophage infects a host cell. The receptor-binding protein plays a role in maintaining stable binding while the genetic material of the bacteriophage is transferred into the host cell during the infection process and is known to be capable of binding to both gram-negative and gram-positive bacteria. Therefore, the present invention increases the contact of the protein complex with the strains and protein transfer efficiency using the characteristics of the receptor-binding protein. In other words, the present invention includes a "receptor-binding protein" and thus the protein complex of the present invention can be more easily and strongly bound to the target microorganism to be killed.

In one embodiment of the present invention, the receptor-binding protein may be selected from the group consisting of PRD1_04, P1301_0153, P24_0149, Pb5, AbTJ_gp52, AbTJ_gp53, phiAB6_gp40, S, A318_gp060, rv5_gp030, rv5_gp033, PaoP5_075, BH773_gp153, AU075_gp145, CPT_Sugarland_191, JIPhKp127_0170, AmPhEK80_0178, P22_gp19, DET7_207, HWD08_gp154, BI021_gp088, HWD21_gp023, HWC41_gp146, HOS12_gp017, HOU44_gp075, I133_gp019, HWC50_gp066 and HOS34_gp106. Any receptor-binding protein may be used so long as it can interact with the target strain and the receptor-binding protein is not necessarily limited to a specific type.

In one embodiment of the present invention, the protein complex has a configuration in which the endolysin, the botulinum toxin translocation domain, and the receptor-binding protein are disposed in this order.

In one embodiment of the present invention, the protein complex preferably has a configuration in which the endolysin, the botulinum toxin translocation domain, and the receptor-binding protein are disposed in this order from the amino terminus to the carboxyl terminus.

In one embodiment of the present invention, the protein complex has a configuration in which the endolysin, the botulinum toxin light chain, the botulinum toxin translocation domain, and the receptor-binding protein are disposed in this order from the amino terminus to the carboxyl terminus.

However, the order of the configuration of the protein complex described above is provided only as an example and thus the order of configuration is not limited thereto.

In one embodiment of the present invention, preferably, the protein complex has a configuration in which endolysin binds to the amino terminus of the botulinum toxin translocation domain and the receptor-binding protein binds to the carboxyl terminus of the botulinum toxin translocation domain.

In another aspect, the present invention is directed to a recombinant vector containing a polynucleotide encoding the protein complex.

As used herein, the term "vector" means a nucleic acid that includes a competent nucleotide sequence that is inserted into a host cell and recombines with and integrates into the host cell genome, or that replicates spontaneously as an episome. These vectors include linear nucleic acids, plasmids, phagemids, cosmids, RNA vectors, viral vectors and the like.

In another aspect, the present invention is directed to a host cell transformed with the recombinant vector containing the polynucleotide encoding the protein complex. The polynucleotide may include a nucleic acid sequence represented by SEQ ID NO: 21.

Host cells include cells that have been transfected, transformed, or infected with a recombinant vector or polynucleotide of the present invention, either in vivo or in vitro. The host cell containing the recombinant vector of the present invention is a recombinant host cell, a recombinant cell, a recombinant microorganism, or a mutant microorganism.

As used herein, the term "transformation" means a phenomenon in which DNA that is introduced into a host can be replicated with an extrachromosomal factor or by insertion into the chromosome.

As used herein, the term "encoded by" or "encoding" means that a polynucleotide expresses a polypeptide sequence.

In accordance with another aspect of the present invention, provided is a method of preparing a protein complex including mixing a first protein fragment containing a botulinum toxin translocation domain with a second protein fragment containing endolysin (a), and linking the mixed protein fragments to each other (b).

In one embodiment of the present invention, the method may further include mixing a third protein fragment containing a receptor-binding protein in the step (a) of mixing the first protein fragment containing the botulinum toxin translocation domain with the second protein fragment containing endolysin.

In one embodiment of the present invention, in the step of mixing (a), the first protein fragment containing the botulinum toxin translocation domain, the second protein fragment containing endolysin, and the third protein fragment containing the receptor-binding protein are mixed at a molar ratio of 1-5:1-5:1-5. According to an embodiment of the present invention, the mixing is preferably performed by mixing the first protein fragment, the second protein fragment, and the third protein fragment at a molar ratio of 1:1:1.

In the present invention, there is no limitation as to the order of mixing the protein fragments in the method for producing the protein complex. For example, the protein complex may be produced by mixing the first protein fragment containing the botulinum toxin translocation domain with the third protein fragment containing the receptor-binding protein, performing reaction, mixing the resulting product with the second protein fragment containing endolysin, and then performing reaction.

The botulinum toxin translocation domain, endolysin, and receptor-binding protein of the present invention are incorporated in the protein complex of one embodiment of the present invention and thus duplicate description is omitted to avoid excessive redundancy in the present specification.

In one embodiment of the present invention, the protein fragments, that is, the first protein fragment, the second protein fragment, and the third protein fragment, may include an intein. The intein is responsible for the reaction in which the two fragments of the split intein, $Int^N$ and $Int^C$, spontaneously form a peptide bond and bind the extein linked to each fragment. The intein bound in this process is separated and removed from the newly bound extein. The protein binding reaction by inteins is referred to as "protein trans-splicing".

In one embodiment of the present invention, the first protein fragment includes different types of inteins, namely, $IntA^C$ and $IntB^N$, at both ends of the botulinum toxin translocation domain, the second protein fragment includes $IntA^N$ and endolysin, and the third protein fragment includes receptor-binding protein and $IntB^C$. The $Int^A$ and $Int^B$ mean that they are different types of inteins.

In one embodiment of the present invention, the botulinum toxin translocation domain, endolysin, receptor-binding protein, and intein of the protein fragment may be linked by a linker.

As used herein, the term "linker" refers to a peptide inserted between two proteins, which are linked to produce another protein, in order to increase the structural flexibility of the proteins or enhance the activity of each protein. Any linker may be used without limitation as long as it does not inhibit the activity of each protein to be fused and does not cause an unnecessary immune response. The linker may be selected from the group consisting of a flexible amino acid linker, an inflexible linker, a cleavable amino acid linker, and a compound linker.

In one embodiment of the present invention, the intein may be selected from the group consisting of Gp41.1, Cfa, NRDJ-1, IMPDH-1, Npu, Ssp, Rma, Ppu, Gp41.8, and NrdA-2.

In one embodiment of the present invention, the step of linking the protein fragments may be performed by a protein trans-splicing reaction.

In one embodiment of the present invention, the protein fragment may include SpyTag and Spycatcher. SpyTag and SpyCatcher are used for irreversible conjugation of recombinant proteins. SpyTag and SpyCatcher spontaneously react with each other to form an intermolecular isopeptide bond therebetween and thereby enable bioconjugation between two recombinant proteins. According to the present invention, the SpyCatcher is present at the C terminus of the botulinum toxin translocation domain, the SpyTag is present in the receptor-binding protein, and the efficiency of binding between receptor-binding protein and the botulinum toxin translocation domain can be improved through the isopeptide bond of the SpyCatcher and SpyTag.

In one embodiment of the present invention, the step of linking the protein fragments may be performed by bioconjugation. Bioconjugation is a chemical reaction that links two biomolecules to each other, is generally a protein-protein conjugation, and serves as a key strategy for linking biomolecules to other substrates. Examples of bioconjugation include coupling of lysine, cysteine, and tyrosine amino acid residues, modification of tryptophan amino acid residues, and modification of the N- and C-termini. In the present invention, as described above, the binding efficiency between the botulinum toxin translocation domain and the receptor-binding protein is increased through the isopeptide bond between the SpyCatcher and the SpyTag.

In another aspect, the present invention is directed to an antibacterial composition containing the protein complex. At this time, the pH of the antibacterial composition is preferably adjusted to 7.4, and the antibacterial composition is not limited to any conditions known in the art. The antibacterial composition of the present invention exhibits antibacterial activity against Gram-positive and Gram-negative bacteria.

The gram-positive bacteria may be Gram-positive bacteria including *Staphylococcus, Listeria, Streptococcus, Corynebacterium, Lactobacillus, Clostridium, Enterococcus, Erysipelothrix,* and *Bacillus*, and may include all Gram-positive bacteria known in the art.

The gram-negative bacteria may be Gram-negative bacteria including *Escherichia, Pseudomonas, Salmonella, Leptospira, Klebsiella, Helicobacter,* and *Enterobacter*, and may include all Gram-negative bacteria known in the art.

The antibacterial composition of the present invention exhibits antibacterial activity against the following pathogens, but is not limited thereto:

*Acinetobacter baumannii, Actinomyces* sp. (for example, *Actinomyces israelii* and *Actinomyces naeslundii, Aeromonas* sp. (for example, *Aeromonas hydrophila, Aeromonas veronii* biovar *sobria (Aeromonas sobria))* and *Aeromonas caviae, Anaplasma phagocytophilum, Alcaligenes xylosoxidans, Actinobacillus actinomycetemcomitans, Bacillus* sp. (for example, *Bacillus anthracis, Bacillus cereus, Bacillus subtilis, Bacillus thuringiensis,* and *Bacillus stearothermophilus, Bacteroides* sp. (for example, *Bacteroides fragilis, Bartonella* sp. (for example, *Bartonella bacilliformis* and *Bartonella henselae, Bifidobacterium* sp., *Bordetella* sp. (for example *Bordetella pertussis, Bordetella parapertussis* and *Bordetella bronchiseptica, Borrelia* sp. (for example, *Borrelia recurrentis* and *Borrelia burgdorferi, Brucella* sp. (for example, *Brucella abortus, Brucella canis, Brucella melintensis* and *Brucella suis, Burkholderia* sp. (for example, *Burkholderia pseudomallei,* and *Burkholderia cepacia, Campylobacter* sp. (for example, *Campylobacter jejuni, Campylobacter coli, Campylobacter lar,* and *Campylobacter fetus, Capnocytophaga* sp., *Cardiobacterium hominis, Chlamydia trachomatis, Chlamydophila pneumonia, Chlamydophila psittaci, Citrobacter* sp. *Coxiella burnetii, Corynebacterium* sp. (for example, *Corynebacterium diphtheria), Corynebacterium jeikeum,* and *Corynebacterium, Clostridium* sp. (for example, *Clostridium perfringens, Clostridium difficile, Clostridium botulinum,* and *Clostridium tetani, Eikenella corrodens, Enterobacter* sp. (for example, *Enterobacter aerogenes, Enterobacter agglomerans, Enterobacter cloacae,* and enterotoxigenic *E. coli,* enteroinvasive *E. coli,* enteropathogenic *E. coli,* enterohemorrhagic *E. coli,* enteroaggregative *E. coli,* and *Escherichia coli* including opportunistic *E. coli* such as uropathogenic *E. coli, Enterococcus* sp. (for example *Enterococcus faecalis* and *Enterococcus faecium), Ehrlichia* sp. (for example, *Ehrlichia chafeensis* and *Ehrlichia canis, Erysipelothrix rhusiopathiae, Eubacterium* sp., *Francisella tularensis, Fusobacterium nucleatum, Gardnerella vaginalis, Gemella morbillorum, Haemophilus* sp. (for example, *Haemophilus influenzae, Haemophilus ducreyi, Haemophilus aegyptius, Haemophilus parainfluenzae, Haemophilus haemolyticus,* and *Haemophilus parahaemolyticus, Helicobacter* sp. for example, *Helicobacter pylori, Helicobacter cinaedi,* and *Helicobacter fennelliae, Kingella kingii, Klebsiella* sp. (for example, *Klebsiella pneumoniae, Klebsiella granulomatis,* and *Klebsiella oxytoca, Lactobacillus* sp., *Listeria monocytogenes, Leptospira interrogans, Legionella pneumophila, Leptospira interrogans, Peptostreptococcus* sp., *Moraxella catarrhalis, Morganella* sp., *Mobiluncus* sp., *Micrococcus* sp., *Mycobacterium* sp. for example, *Mycobacterium leprae, Mycobacterium intracellulare, Mycobacterium avium, Mycobacterium bovis,* and *Mycobacterium marinum, Mycoplasm* sp. (for example, *Mycoplasma pneumoniae, Mycoplasma hominis,* and *Mycoplasma genitalium, Nocardia* sp. (for example, *Nocardia asteroides, Nocardia cyriacigeorgica,* and *Nocardia brasiliensis, Neisseria* sp. (for example, *Neisseria gonorrhoeae,* and *Neisseria meningitidis, Pasteurella multocida, Plesiomonas shigelloides, Prevotella* sp., *Porphyromonas* sp., *Prevotella melaninogenica, Proteus* sp. (for example, *Proteus vulgaris* and *Proteus mirabilis, Providencia* sp. (for example, *Providencia alcalifaciens, Providencia rettgeri,* and *Providencia stuartii, Pseudomonas aeruginosa, Propionibacterium acnes, Rhodococcus equi, Salmonella* sp. (for example, *Salmonella enterica, Salmonella typhi, Salmonella paratyphi, Salmonella enteritidis, Salmonella cholerasuis,* and *Salmonella typhimurium, Serratia* sp. (for example, *Serratia marcesans,* and *Serratia liquifaciens, Shigella* sp. (for example, *Shigella dysenteriae, Shigella flexneri, Shigella boydii* and *Shigella sonnei, Staphylococcus* sp. (for example, *Staphylococcus aureus, Staphylococcus epidermidis, Staphylococcus hemolyticus, Staphylococcus saprophyticus, Streptococcus* sp. (for example, *Streptococcus pneumoniae,* Spectinomycin-resistant serotype 6B *Streptococcus pneumoniae,* Streptomycin-resistant serotype 9V *Streptococcus pneumoniae,* Erythromycin-resistant serotype 14 *Streptococcus pneumoniae,* Optochin-resistant serotype 14 *Streptococcus pneumoniae,* Rifampicin-resistant serotype 18C *Streptococcus pneumoniae,* Tetracycline-resistant serotype 19F *Streptococcus pneumoniae,* Penicillin-resistant serotype 19F *Streptococcus pneumoniae* and Trimethoprim-resistant serotype 23F *Streptococcus pneumoniae,* Chloramphenicol-resistant serotype 4 *Streptococcus pneumoniae,* Streptomycin-resistant serotype 9V *Streptococcus pneumoniae,* Optochin-resistant serotype 14 *Streptococcus pneumoniae,* Rifampicin-resistant serotype 18C *Streptococcus pneumoniae,* Penicillin-resistant serotype 19F *Streptococcus pneumoniae)* or Trimethoprim-resistant serotype 23F *Streptococcus pneumoniae, Streptococcus agalactiae, Streptococcus mutans, Streptococcus pyogenes,* Group A streptococci, *Streptococcus pyogenes,* Group B streptococci, *Streptococcus agalactiae,* Group C streptococci, *Streptococcus anginosus, Streptococcus equisimilis,* Group D streptococci, *Streptococcus bovis,* Group F streptococci and *Streptococcus anginosus,* Group G streptococci, *Spirillum minus, Streptobacillus moniliformi, Treponema* sp. (for example, *Treponema carateum, Treponema petenue, Treponema pallidum,* and *Treponema endemicum, Tropheryma whippelii, Ureaplasma urealyticum, Veillonella* sp., *Vibrio* sp. (for example, *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii, Yersinia* sp. (for example, *Yersinia enterocolitica* and *Yersinia pestis* and *Xanthomonas maltophilia*).

In one embodiment of the present invention, the antibacterial composition is an antibacterial pharmaceutical composition.

The pharmaceutical composition of the present invention may further contain a pharmaceutically acceptable carrier in addition to the composition as an active ingredient.

The pharmaceutically acceptable additive contained in the pharmaceutical composition of the present invention may be commonly used in the formulation and includes, but is not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate and mineral oil.

In addition to the ingredients, the pharmaceutical composition of the present invention may further contain lubricants, wetting agents, sweeteners, flavoring agents, emulsifiers, suspending agents, preservatives, or the like. Suitable pharmaceutically acceptable carriers and agents are described in detail in Remington's Pharmaceutical Sciences (19th ed., 1995).

The pharmaceutical composition of the present invention may be administered orally or parenterally, for example, intrathecally, intravenously, subcutaneously, intradermally, intramuscularly, intraperitoneally, intrasternally, intratumorally, intranasally, intracerebrally, intracranially, intrapulmonarily, and intrarectally, but is not limited thereto.

That is, the pharmaceutically effective amount of the pharmaceutical composition of the present invention may vary depending on the formulation method, administration method, age, weight, gender, pathological condition, diet, administration time, administration route, excretion rate and reaction sensitivity of the patient. Ordinary skilled physicians can easily determine and prescribe an effective dosage (pharmaceutically effective amount) for desired treatment or prevention. According to a preferred embodiment of the present invention, the daily dose of the pharmaceutical composition of the present invention is about 0.0001 to about 100 mg/kg.

As used herein, the term "pharmaceutically effective amount" means an amount sufficient to prevent or treat the disease.

As used herein, the term "prevention" refers to any action that suppresses or delays the onset of a disease by administration of the pharmaceutical composition according to the present invention. As used herein, the term "treatment" refers to any action that reduces, inhibits, ameliorates or removes disease conditions.

The pharmaceutical composition of the present invention is formulated into a unit dose form or packaged into a multiple dose container using a pharmaceutically acceptable carrier and/or excipient in accordance with a method that can be easily performed by those skilled in the art. The formulation may be prepared in a variety of forms, such as an oral drug or injection, may be in the form of a solution, suspension or emulsion in an oil or aqueous medium, or in the form of an extract, a powder, a suppository, a powder, a granule, a tablet or a capsule, and may further contain a dispersant or stabilizer.

In another aspect, the present invention is directed to a method for preventing or treating bacterial infection, including administering to a subject an antibacterial composition containing the protein complex of the present invention described above.

As used herein, the term "bacterial infection" refers to a disease caused by bacterial infection. Examples of the bacterial infection include tuberculosis, pneumonia, food poisoning, sepsis, toxic shock syndrome, scarlet fever, diphtheria, brucellosis, listeriosis, typhoid fever, paratyphoid fever, cholera, botulism, tetanus, leprosy, leptospirosis, and the like, caused by the pathogens describe above, but are not limited thereto.

As used herein, the term "administration" or "administering" means directly administering a therapeutically or prophylactically effective amount of the composition of the present invention to a subject suffering from, or likely to suffer from, the disease of interest, so that the same amount accumulates in the body of the subject.

As used herein, the term "therapeutically effective amount" refers to the content of the composition sufficient to impart a therapeutic or prophylactic effect to the subject to whom the composition is administered, and is meant to include a "prophylactically effective amount."

In addition, as used herein, the term "subject" refers to mammals including humans, mice, rats, guinea pigs, dogs, cats, horses, cows, pigs, monkeys, chimpanzees, baboons, and rhesus monkeys. Most specifically, the subject of the present invention is a human.

The method for preventing or treating bacterial infection of the present invention includes administering a pharmaceutical composition, which is an aspect of the present invention, and thus duplicate description is omitted to avoid excessive redundancy in the specification.

In another aspect, the present invention is directed to a feed additive containing the protein complex described above.

The feed additive may be in a liquid or dry form, for example, in a dried powder.

In addition, the feed additive may further contain ordinary additives that can increase the preservability of the feed in addition to the antibiotic.

Here, the feed additives include, but are not limited to, commercially available feed, grains, roots, fruits, food processing by-products, algae, fibers, pharmaceutical by-products, oils and fats, starches, cucurbits, grain by-products, proteins, inorganics, oils and fats, minerals, single-cell proteins, zooplankton, leftover food, and the like.

In another aspect, the present invention is directed to a food additive or drinking water additive containing the protein complex as an active ingredient. By mixing and supplying the protein complex with drinking water, the number of strains in drinking water can be reduced.

The protein complex of the present invention functions to deliver endolysin into the target strain using the botulinum toxin translocation domain and thus has lytic activity not only against Gram-positive bacteria but also against Gram-negative bacteria, which endolysin has difficulty acting upon, based on this function. Further, the usability of the protein delivery system can be improved using a receptor-binding protein.

The antibacterial activity of the protein complex of the present invention is based on the protein delivery system of the botulinum toxin translocation domain, and the endolysin and receptor-binding protein may be selected in accordance with the target strain, and exhibits antibacterial activity, regardless of the type of endolysin and receptor-binding protein.

Furthermore, when producing a protein complex by reacting (protein trans-splicing) a protein fragment containing a botulinum toxin translocation domain with a protein fragment containing endolysin, than when producing a full-length protein complex at once, the protein complex is not easily denatured during the preparation process and is not vulnerable to chemical stress, and the preparation efficiency thereof is improved.

In another aspect, the present invention is directed to a method for screening an antibacterial protein complex including reacting the protein complex with a target strain, and determining whether or not the protein complex exhibits antibacterial activity against the target strain.

Through the screening method, by reacting the protein complex containing receptor-binding protein candidates and endolysin candidates with the target strain, and determining whether or not the candidates exhibit antibacterial activity against the target strain can be determined, whether or not the candidates can be used as receptor-binding proteins and endolysin can be determined.

The method for determining whether or not the candidate exhibits the antibacterial activity is not particularly limited and a known method may be used singly or in combination. According to an embodiment of the present invention, the method may be performed through a spotting assay.

Hereinafter, the present invention will be described in more detail with reference to the following examples. It will be obvious to those skilled in the art that these examples are provided only for better understanding of the present invention and thus should not be construed as limiting the scope of the present invention based on the subject matter of the present invention.

Throughout this specification, "percentage (%)" used to indicate a concentration of a specific substance means (weight/weight) % for solid/solid, (weight/volume) % for solid/liquid, and (volume/volume) % for liquid/liquid, unless mentioned otherwise.

<Botulinum Toxin Translocation Domain, Endolysin, Receptor-Binding Protein, Intein, SpyTag/Spycatcher for Production of Translysin (Protein Complex)>

Botulinum toxin translocation domain (Table 1), endolysin (Table 2) for preparation of translysin, receptor-binding protein (Table 3), intein (Table 4), and SpyTag/Spycatcher (Table 5) are listed as follows.

TABLE 1

| Botulinum toxin translocation domain ($H_N$) | | | | |
|---|---|---|---|---|
| Name | Predicted function | Size (a.a) | origin | NCBI Accession # |
| BoNT A2 Translocation domain | Translocation domain | 422 | *Clostridium botulinum* strain Kyoto/Type A2 | Q45894 (449-870 region) |
| BoNT C1 Translocation domain | Translocation domain | 416 | *Clostridium botulinum* C bacteriophage | P18640 (450-865 region) |
| BoNT E1 Translocation domain | Translocation domain | 397 | *Clostridium botulinum* | Q00496 (423-819 region) |

TABLE 2

| Endolysin for production of translysin | | | | |
|---|---|---|---|---|
| Name | Predicted functions | Size (a.a) | Origin | NCBI Accession # |
| lys | L-alanyl-D-glutamate endopeptidase (M15) | 137 | *Escherichia* virus T5 | YP_006868 |
| LysPA26 | Muramidase (GH24) | 145 | *Pseudomonas* phage JD010 | KY615005 |
| PB1_gp48 | Chitinase (GH19) | 220 | *Pseudomonas* phage PB1 | NC_011810 |
| LysAB2_P3 | Chitinase (GH19) | 185 | *Acinetobacter* phage phiAB2 | HM755898 |
| PlyF307 | Muramidase (GH24) | 146 | *Acinetobacter* phage RL-2015 | KJ740396 |
| AcLys | Muramidase (GH24) | 184 | *Acinetobacter baumannii* AB5075 prophage | WP_000208716 |
| PlyPA03 | Muramidase (GH24) | 144 | *Pseudomonas aeruginosa* prophage | WP_070344501 |
| PlyPA91 | Muramidase (GH24) | 154 | *Pseudomonas aeruginosa* prophage | CRR10611 |
| Abtn-4 | Chitinase (GH19) | 185 | *Acinetobacter* phage VB_AbaP_D2 | AVP40474 |
| WCHABP1_gp01 | N-acetylmuramidase (GH108) | 171 | *Acinetobacter* phage WCHABP1 | AST13128 |
| WCHABP12_gp19 | Chitinase (GH19) | 202 | *Acinetobacter* phage WCHABP12 | ARB06760 |
| gh-1p12 | N-acetylmuramoyl-L-alanine amidase | 146 | *Pseudomonas* phage gh-1 | NP_813758 |
| B3ORF25 | Membrane-bound lytic murein transglycosylase F | 264 | *Pseudomonas* phage B3 | YP_164061 |

TABLE 2-continued

Endolysin for production of translysin

| Name | Predicted functions | Size (a.a) | Origin | NCBI Accession # |
|---|---|---|---|---|
| phi-13Sp4 | P5 muramidase | 245 | *Pseudomonas* phage phi13 | NP_690810 |
| phi-6S_4 | Peptidase_U40 | 220 | *Pseudomonas* phage phi6 | NP_620343 |
| KP27_166 | L-alanyl-D-glutamate endopeptidase | 131 | *Klebsiella* phage VB_KpnM_KP27 | AEX26632 |
| KP13_gp066 | Muramidase (GH24) | 160 | *Klebsiella* phage VB_KpnS_Kp13 | AZF89867 |
| BI057_gp221 | T4-like lysozyme | 164 | *Shigella* phage SHFML-26 | YP_009279119 |
| LPSE_00024 | Soluble Lytic Transglycosylases | 162 | *Salmonella* phage LPSE1 | APU02985 |
| STP4a_120 | Soluble Lytic Transglycosylases | 166 | *Salmonella* phage STP4-a | AHJ86974 |
| Lys68 | Soluble Lytic Transglycosylases | 162 | *Salmonella* phage phi68 | AHY18890 |
| SPN1S_0028 | Chitinase (GH19) | 209 | *Salmonella* phage SPN1S | YP_005098003 |
| P22gp66 | Lysozyme | 146 | *Salmonella* virus P22 | NP_059622 |

TABLE 3

Receptor-binding protein (RBP)

| Name | Predicted functions | Size (a.a) | origin | NCBI Accession # |
|---|---|---|---|---|
| PRD1_04 | Adsorption protein | 591 | *Enterobacteria* phage PRD1 | NC_001421 |
| P1301_0153 | Receptor-binding protein | 593 | *Bacteriophage* T5-like chee130_1 | ASU02516 |
| P24_0149 | Receptor-binding protein | 585 | *Bacteriophage* T5-like chee24 | NC_047885 |
| Pb5 | Receptor-binding tail protein | 640 | *Escherichia* virus T5 | NC_005859 |
| AbTJ_gp52 | Tail fiber protein | 202 | *Acinetobacter* phage AbTJ | QAU04145 |
| AbTJ_gp53 | Tail fiber protein | 699 | *Acinetobacter* phage AbTJ | QAU04146 |
| phiAB6_gp40 | Tail fiber | 699 | *Acinetobacter* phage phiAB6 | ALA12264 |
| S | Tail fiber protein | 504 | *Escherichia* phage Mu | NC_000929 |
| A318_gp060 | Receptor-binding tail protein | 585 | *Escherichia* phage vB_EcoS_AKFV33 | NC_017969 |
| rv5_gp030 | Tail fiber protein | 347 | *Escherichia* phage rV5 | YP_002003532 |
| rv5_gp033 | Putative tail fiber protein | 346 | *Escherichia* phage rV5 | YP_002003535 |
| PaoP5_075 | Structural protein | 243 | *Pseudomonas* phage PaoP5 | YP_009224766 |
| BH773_gp153 | Putative tail fiber protein | 670 | *Pseudomonas* phage K5 | YP_009273830 |
| AU075_gp145 | Putative tail fiber protein | 499 | *Pseudomonas* phage C11 | YP_009186965 |
| CPT_Sugarland_191 | Receptor-binding protein | 658 | *Klebsiella* phage Sugarland | ATW62004 |

TABLE 3-continued

| Receptor-binding protein (RBP) | | | | |
|---|---|---|---|---|
| Name | Predicted functions | Size (a.a) | origin | NCBI Accession # |
| JIPhKp127_0170 | Receptor-binding protein | 658 | *Klebsiella* phage JIPh_Kp127 | QFR57578 |
| AmPhEK80_0178 | Receptor-binding protein | 658 | *Klebsiella* phage AmPh_EK80 | QFR57428 |
| P22_gp19 | Tail spike protein | 667 | *Salmonella* phage P22 | NC_002371 |
| DET7_207 | Tail spike protein | 708 | *Salmonella* phage Det7 | YP_009140379 |
| HWD08_gp154 | Receptor-binding tail protein | 585 | *Salmonella* phage L6jm | YP_009856550 |
| BI021_gp088 | Receptor-binding protein | 595 | *Salmonella* phage NR01 | YP_009283429 |
| HWD21_gp023 | Receptor-binding tail protein | 640 | *Salmonella* phage oldekolle | YP_009857757 |
| HWC41_gp146 | Receptor-binding protein | 593 | *Salmonella* phage SE24 | YP_009848613 |
| HOS12_gp017 | Receptor-binding protein | 585 | *Salmonella* phage SP01 | YP_009792475 |
| HOU44_gp075 | Receptor-binding protein | 593 | *Salmonella* phage STG2 | YP_009815133 |
| I133_gp019 | Receptor recognition protein | 249 | *Salmonella* phage vB_SenM-S16 | YP_007501289 |
| HWC50_gp066 | Receptor-binding tail protein | 585 | *Salmonella* virus VSe12 | YP_009849685 |
| HOS34_gp106 | Receptor-binding tail protein | 585 | *Shigella* phage SSP1 | YP_009794581 |

TABLE 4

| Intein | | | | |
|---|---|---|---|---|
| Name | Domain | Sequence | SEQ ID NO: | Remarks |
| Gp41.1 | Int-N | CLDLKTQVQTPQGMKEISNIQVGDLVLSNTGYNEVL NVFPKSKKKSYKITLEDGKEIICSEEHLFPTQTGEM NISGGLKEGMCLYVKE | 1 | |
| | Int-C | MMLKKILKIEELDERELIDIEVSGNHLFYANDILTH N | 2 | |
| Cfa | Int-N | CLSYDTEILTVEYGFLPIGKIVEERIECTVYTVDKN GFVYTQPIAQWHNRGEQEVFEYCLEDGSIIRATKDH KFMTTDGQMLPIDEIFERGLDLKQVDGLP | 3 | |
| | Int-C | MVKIISRKSLGTQNVYDIGVEKDHNFLLKNGLVASN | 4 | |
| NRDJ-1 | Int-N | CLVGSSEIITRNYGKTTIKEVVEIFDNDKNIQVLAF NTHTDNIEWAPIKAAQLTRPNAELVELEIDTLHGVK TIRCTPDHPVYTKNRGYVRADELTDDDELVVA | 5 | |
| | Int-C | MIEAKTYIGKLKSRKIVSNEDTYDIQTSTHNFFAND ILVHN | 6 | |
| IMPDH-1 | Int-N | CFVPGTLVNTENGLKKIEEIKVGDKVFSHTGKLQEV VDTLIFDRDEEIISINGIDCTKNHEFYVIDKENANR VNEDIHLFARWVVHAEELDMKKHLLIELE | 7 | |
| | Int-C | MKFKLKEITSIETKHYKGKVHDLTVNQDHSYNVRGT VVHN | 8 | |

TABLE 4-continued

Intein

| Name | Domain | Sequence | SEQ ID NO: | Remarks |
|---|---|---|---|---|
| Npu | Int-N | CLSYETEILTVEYGLLPIGKIVEKRIECTVYSVDNN GNIYTQPVAQWHDRGEQEVFEYCLEDGSLIRATKDH KMTVDGQMLPIDEIFERELDLMRDNLPN | 9 | DnaE |
| | Int-C | MIKIATRKYLGKQNVYDIGVERDHNFALKNGFIASN | 10 | |
| Ssp | Int-N | CLSFGTEILTVEYGPLPIGKIVSEEINCSVYSVDPE GRVYTQAIAQWHDRGEQEVLEYELEDGSVIRATSDH RFLTTDYQLLAIEEIFARQLDLLTLENIKQTEEALD NHRLPFPLLDAGTIK | 11 | DnaE |
| | Int-C | MVKVIGRRSLGVQRIFDIGLPQDHNFLLANGAIAAN | 12 | |
| Rma | Int-N | CLAGDTLITLADGRRVPIRELVSQQNFSVWALNPQT YRLARVSRARVSRAFCTGIKPVYRLTTRLGRSIRAT ANHRFLTQGWKRVDELQPGDYLALPRRIPTASTPTL TEAELALLGHLIGD | 13 | DnaB |
| | Int-C | MWDPIVSIEPDGVEEVFDLTVPGPHNFVADNIIAGN S | 14 | |
| Ppu | Int-N | CISKFSHIMWSHVSKPLFNFSIKKSHMHNGNKNIYQ LLDQGEAFISRQDKKTTYKIRTNSEKYLELTSNHKI LTLRGWQRCDQLLCNDMITTQIGFELSRKKKYLLNC IPFSLCNFET | 15 | DnaB |
| | Int-C | MLANINISNFQNVEDFAANPIPNFIANNIIVHNS | 16 | |
| Gp41.8 | Int-N | CLSLDTMVVINGKAIEIRDVKVGDWLESECGPVQVT EVLPIIKQPVFEIVLKSGKKIRVSANHKFPTKDGLK TINSGLKVGDFLRSRA | 17 | |
| | Int-C | MCEIFENEIDWDEIASIEYVGVEETIDINVINDRLF FANGILTHN | 18 | |
| NrdA-2 | Int-N | CLTGDAKIDVLIDNIPISQISLEEVVNLFNEGKEYV LSYNIDTKEVEYKEISDAGLISESAEVLEIIDEETG QKIVCTPDHKVYTLNRGYVSAKDLKEDDELVES | 19 | |
| | Int-C | MGLKIIKRESKEPVFDITKVKDNSNFFANNILVHN | 20 | |

TABLE 5

SpyTag & Spycatcher

| Name | Domain | Sequence | SEQ ID NO: | Remarks |
|---|---|---|---|---|
| Spy001 | Catcher | GAMVDTLSGLSSEQGQSGDMTIEEDSATHIKF SKRDEDGKELAGATMELRDSSGKTISTWISDG QVKDFYLYPGKYTFVETAAPDGYEVATAITFT VNEQGQVTVNGKATKGDAHI | 32 | |
| | Tag | AHIVMVDAYKPTK | 33 | |
| Spy002 | Catcher | AMVTTLSGLSGEQGPSGDMTTEEDSATHIKFS KRDEDGRELAGATMELRDSSGKTISTWISDGH VKDFYLYPGKYTFVETAAPDGYEVATAITFTV NEQGQVTVNGEATKGDAHTGSSGS | 34 | |
| | Tag | VPTIVMVDAYKRYK | 35 | |
| Spy003 | Catcher | VTTLSGLSGEQGPSGDMTTEEDSATHIKFSKR DEDGRELAGATMELRDSSGKTISTWISDGHVK DFYLYPGKYTFVETAAPDGYEVATPIEFTVNE DGQVTVDGEATEGDAHT | 36 | |
| | Tag | RGVPHIVMVDAYKRYK | 37 | |

However, the contents described in Tables 1 to 5 are provided for illustrating the present invention in more detail and Tables 1 to 5 should not be construed as limiting the scope of the present invention.

Example 1: Verification of Intracellular Expression and Lytic Effect of Full-Length Translysin To express full-length translysin (endolysin-$H_N$-RBP) in the expression host, *E. coli* shuffle T7, a plasmid encoding the translysin was designed. The protein complex was designed to have endolysin (T5 lys) and RBP (Pb5) bound to the amino and carboxyl ends of the botulinum toxin $H_N$ domain, respectively, and was inserted into a pET vector to produce a plasmid (FIG. 1). The sequence of the full-length translysin inserted into the vector is shown in SEQ ID NO: 21. The plasmid was inserted into an *E. coli* host at 42° C., cultured on LB (Luria-Bertani) agar medium supplemented with kanamycin at a concentration of 50 μg/mL and a transformed *E. coli* strain was selected.

The selected transformed strain was inoculated into LB culture medium and sub-cultured. 1 mM IPTG (isopropyl β-D-1-thiogalactopyranoside) was added to the cultured solution, followed by incubation at 37° C. for 4 hours to induce expression of translysin, which was then identified by SDS gel electrolysis (FIG. 2). As control groups, a transformed strain of a plasmid encoding an endolysin fragment or innolysin (T5 lys-linker-Pb5) and a wild-type strain were used, and the expression of innolysin was identified by SDS gel electrophoresis (FIG. 3). The sequence of innolysin is shown in SEQ ID NO: 22. The activity of translysin was predicted by measuring the growth of the strain based on the turbidity of the culture medium after expression. It was predicted that, when the expressed protein complex passed through the cell membrane and lysed the peptidoglycan of the cell wall, the strain died and turbidity decreased.

The result of expression showed that the strain expressing the endolysin fragment and innolysin did not exhibit a significant difference from the growth pattern of the wild-type strain, but when the translysin of the present invention was expressed, growth was significantly reduced, which indicates that membrane transfer occurred effectively (FIGS. 4 and 5).

Example 2: Protein Trans-Splicing of Protein Fragment by Intein

During the expression process, the full-length translysin expressed in Example 1 has problems in that 1) it has difficulty in reaching a sufficient cell concentration because the expression host is lysed, 2) it is readily denatured and is thus expressed at a low amount in a soluble form because the folding of the expression product of about 180 kDa is not smooth, and 3) it is vulnerable to physical and chemical stress during separation and purification because the size of the expression product reaches about 180 kDa. Therefore, in order to overcome these problems, the present invention adopts a method of expressing and purifying endolysin, $iLCH_N$ (inactivated botulinum toxin light chain+botulinum toxin translocation domain), and RBP as respective fragments linked to intein, and linking the fragments in vitro.

Gp41.1 intein and Cfa intein were selected from Table 4 in consideration of the linking conditions and reaction rates of inteins, and applied to endolysin-$iLCH_N$ and $iLCH_N$-RBP binding, respectively. At this time, LysPA26 and PB1_gp48 in Table 2 were selected as endolysins, and PRD1_04 in Table 3 was selected as RBP.

The method for producing protein fragments is the same as in Example 1 and the sequences used to produce protein fragments are as follows:

```
LysPA26-Gp41.1N: SEQ ID NO: 23;

PB1_gp48-Gp41.1N: SEQ ID NO: 24;

Gp41.1C-iLCH N-CfaN: SEQ ID NO: 25;
and

CfaC-PRD1_04: SEQ ID NO: 26.
```

As a result, four protein fragments (LysPA26-Gp41.1N, 27.5 kDa; PB1_gp48- Gp41.1N, 35.3 kDa; Gp41.1C-iLCHN-CfaN, 117.2 kDa; CfaC-PRD1_04, 69.3 kDa) were expressed and purified. A protein trans-splicing reaction was performed (A of FIG. 6).

First, to determine the trans-splicing effects of Gp41.1 intein and Cfa intein, the fragments were mixed at a molar ratio of 1:1 and the reaction was performed. As a result, 128.7 kDa (LysPA26-$iLCH_N$-CfaN), 136.5 kDa (PB1_gp48-$iLCH_N$-CfaN), and 168.9 kDa (gp41.1C-$LCH_N$-PRD1_04) reaction products were obtained in buffer solution and saturated after 30 minutes (FIGS. 7 to 9). The result of the reaction performed by mixing the fragments at a molar ratio of 1:1:1 showed that the final product of 189.1 kDa, and the intermediate products of 136.5 kDa (PB1_gp48-$iLCH_N$-CfaN) and 168.9 kDa (Gp41.1C-$iLCH_N$-PRD1_04) were obtained in buffer solution regardless of the use of the reducing agent (FIG. 10).

Example 3: Conversion of Protein Fragments to Full-Length Proteins by Intein and SpyTag/SpyCatcher In the full-length translysin produced in Example 2, the intein can be removed, but there was a problem of low trans-splicing efficiency of about 25%. Therefore, in order to overcome this problem, the present invention adopted a method of expressing and purifying endolysin, $iLCH_N$, and RBP as respective fragments linked to intein and SpyTag/Spycatcher, and linking the fragments in vitro.

In consideration of the binding conditions and reaction rate of the intein and the mechanism of action of translysin, Gp41.1 intein was selected from Table 4 and applied to endolysin-$iLCH_N$ binding. In consideration of the reaction speed of the SpyTag/Spycatcher, the $3^{rd}$ generation SpyTag/Spycatcher was selected from Table 5 and applied to $iLCH_N$-RBP binding. At this time, LysPA26 was selected as the endolysin from Table 2 and PRD1_04 was selected as the RBP from Table 3.

The method for producing protein fragments is the same as in Example 1 and the sequences used to produce protein fragments are as follows:

```
LysPA26-Gp41.1N: SEQ ID NO: 23;

Gp41.1C-iLCH N-Spy C003: SEQ ID NO: 42;
and

Spy T003-PRD1_04: SEQ ID NO: 43
```

As a result, three protein fragments (LysPA26-Gp41.1N, 27.5 kDa; Gp41.1C-iLCHN-SpyC003, 117.8 kDa;

SpyT003-PRD1_04, 67.0 kDa) were expressed, purified and reacted into full-length translysin in vitro (B of FIG. 6).

First, to determine the trans-splicing effect of Gp41.1 intein, the fragments were mixed at a molar ratio of 1:1 and the reaction was performed. The result showed that 129.1 kDa (LysPA26-iLCH$_N$-Spy$^C$003) was obtained in the buffer solution and saturated after 30 minutes (FIG. 11). In order to determine protein binding by SpyTag and Spycatcher, the fragments were mixed at a molar ratio of 1:1 and the reaction was performed. As a result, a reaction product of 184.8 kDa (gp41.1C-iLCH$_N$-Spy-PRD1_04) was obtained in the buffer solution (FIG. 11). The result of the reaction performed by mixing respective fragments at a molar ratio of 1:1:1 showed that a final product of 196.1 kDa and an intermediate product of 129.1 kDa (Gp41.1C-iLCH$_N$-Spy-PRD1_04) were produced in the buffer solution (FIG. 11).

Example 4: Verification of Lytic Activity of Full-Length Translysin and Protein Fragments To determine the membrane transport and lytic activity of the full-length translysin produced in Examples 2 and 3, a spotting assay was performed on the target strain. The spotting assay is a method including overlaying a homogeneous mixture of 0.4% soft agar and the target strain on LB agar medium, drying the result, spotting the protein sample, culturing the sample, and determining death or growth inhibition patterns of strains on the lawn (FIG. 12).

Spotting assays were performed in two groups. First, to verify the lytic activity of endolysin, an experiment was conducted using dead cells in which the outer membrane of the *Pseudomonas aeruginosa* KACC 10186 strain was destroyed. For this purpose, the target strain was cultured until the exponential phase ($OD_{600}$<2.0), sterilized at 121° C. using an autoclave, and then washed once with a buffer solution (50 mM Tris, 100 mM NaCl; pH 7, LysPA26/pH 6, PB1_gp48) to prepare a final 100-fold concentrated dead cell solution, diluted such that the turbidity of 0.4% soft agar was adjusted to $OD_{600}$ of 10, and 5 mL of the dilution was placed on the LB agar medium in a 90Ø Petri dish. After the soft agar was dried, 10 μL of each endolysin sample stock solution (10 μg/μL) and the dilution (1 μg/μL, 0.1 μg/μL, 0.01 μg/μL) were spotted, and a buffer solution was used as a negative control. The result of the test showed that both LysPA26 and PB1_gp48 endolysin fragments formed a lysis zone in the lawn, which indicates that the fragments exhibit lytic activity against the peptidoglycan of the target strain (FIGS. 13 and 14).

Then, to determine the membrane transport activity, an experiment was conducted by treating *Pseudomonas putida* KCTC 1643 viable cells with the protein sample under the same conditions. For this purpose, 100 μL of live bacteria cultured overnight at 37° C. in LB culture medium until a stationary phase were homogeneously mixed with 5 mL of 0.4% LB soft agar and overlayed to create an environment that promotes the growth of live bacteria. After the soft agar was dried, 10 μL of each of the stock solution (4 μg/μL) and diluted solutions (0.4 μg/μL, 0.04 μg/μL) of translysin (PB1_gp48-iLCH$_N$-PRD1_04, LysPA26-iLCH$_N$-PRD1_04) and endolysin fragments (PB1_gp48-Gp41.1N, LysPA26-Gp41.1N) were spotted, and a buffer solution was used as a negative control. The result of the experiment showed that no lytic action occurred when treated with each endolysin fragment, whereas a lysis zone was formed when treated with full-length translysin, which indicates that the protein was effectively delivered into the outer membrane of the target strain and lysed the cell. (FIGS. 15 and 16).

The result was treated with translysin (PB1_gp48-iLCH$_N$-PRD1_04, LysPA26-iLCH$_N$-PRD1_04) and endolysin fragments (PB1_gp48-Gp41.1N, LysPA26-Gp41.1N) assembled through SpyTag and Spycatcher, and innolysin (LysPA26-iLCH N-PRD1_04, PB1_gp48-iLCH N-PRD1_04) at 3.6 μM and 360 nM, respectively, under the same conditions. The result of the experiment showed that lytic activity did not occur when treated with each endolysin fragment, whereas when treated with full-length translysin and innolysin, a lytic zone was formed. The full-length translysin exhibited the effect at both 3.6 μM and 360 nM, whereas innolysin exhibited the effect at 3.6 μM (FIGS. 17 and 18).

Example 5: Visualization of Lytic Activity of Translysin

Transmission electron microscopy (TEM) was performed to visually detect the lytic activity of translysin verified in Example 4 (FIG. 19). For this purpose, the target strain *P. putida* KCTC 1643 was inoculated into the LB culture at a turbidity of $OD_{600}$=0.1, cultured at 37° C. for 2 hours until the early exponential phase ($OD_{600}$=1.0), and washed twice with a buffered saline solution to prepare live bacteria. Then, about 1 mL of the live bacteria solution was mixed with 370 nM translysin (PB1_gp48-iLCH$_N$-PRD1_04, LysPA26-iLCH$_N$-PRD1_04), cultured at 25° C., and 10 μL of the mixture was collected at a predetermined time point, fixed on a gold grid, and then stained with uranyl acetate for 10 seconds to prepare a TEM sample. A negative control sample was prepared in the same manner as above by treating a strain with each endolysin fragment (PB1_gp48-Gp41.1N, LysPA26-Gp41.1N) at a concentration of about 370 nM, or was prepared in the same manner as above using a strain without any treatment. As a result of analysis using an energy-filtering transmission electron microscope (Energy-Filtering TEM, 120 kv) (Carl Zeiss, Libra 120), no external damage was observed in the negative control, whereas the cell wall of the experimental group treated with translysin was damaged over time and the strain died (FIG. 19).

Example 6: Quantification of Lytic Activity of Translysin

CFU (Colony Forming Unit) reduction assay was performed to numerically determine the lytic activity of translysin verified in Example 4. For this purpose, the target strain *P. putida* KCTC 1643 was inoculated into LB culture medium at a turbidity of $OD_{600}$=0.1, cultured at 37° C. for 1.5 hours until the early exponential phase ($OD_{600}$=0.6), washed three times with a 20 mM HEPES-NaOH (pH=7.4) solution, diluted 100 times and prepared as live bacteria. Then, 100 uL of translysin (LysPA26-iLCH$_N$-PRD1_04) or innolysin (LysPA26-PRD1) was mixed at a concentration of 30 μM with 100 μL of the live bacteria solution and reacted at 37° C. for 1 hour. As a negative control, a sample was prepared in the same manner as above using 20 mM Hepes-NaOH. Then, the result was diluted with an appropriate dilution factor, spread on LB agar medium, and cultured O/N at 37° C. Antibacterial activity was determined based on the difference in mean logarithmic cell concentration of translysin- or innolysin-treated samples compared to the negative control. The result of the experiment showed that translysin exhibited about twice the lytic activity of innolysin (FIG. 20).

Example 7: Translysin Library-Based Antibacterial Substance Screening

A translysin screening method was designed to discover antibacterial substances against various strains using the protein delivery system of the present invention (FIG. 21). Specifically, the endolysins and RBPs in Tables 2 and 3 were combined to construct a translysin library, and viable cells of the target strain in Table 6 were homogeneously mixed with 0.4% LB soft agar to form a lawn. Then, novel antibacterial materials for each strain could be discovered by determining the lytic activity through spotting assay.

TABLE 6

| Candidate bacteria | Remarks |
| --- | --- |
| *Pseudomonas aeruginosa* PAO1 | |
| *Pseudomonas aeruginosa* KACC 10186 | |
| *Pseudomonas aeruginosa* ATCC 15692 | |
| *Pseudomonas aeruginosa* ATCC 27853 | |
| *Pseudomonas putida* KCTC 1643 | |
| *Escherichia coli* BL21 | |
| *Escherichia coli* MG1655 | |
| *Escherichia coli* ATCC 43889 | O157:H7, Stx2, hemolytic uremic syndrome |
| *Escherichia coli* ATCC 43890 | O157:H7, Stx1 |
| *Escherichia coli* ATCC 43895 | O157:H7, Stx1, Stx2, hemorrhagic colitis |
| *Escherichia coli* ATCC 35150 | O157:H7, hemorrhagic colitis |
| *Escherichia coli* ATCC 25922 | O6, clinical isolate |
| *Salmonella* Typhimurium SL1344 | |
| *Salmonella* Typhimurium UK-1 | |
| *Salmonella* Typhimurium 14028s | |
| *Salmonella* Typhimurium LT2 | |
| *Salmonella* Typhimurium DT104 | zoonotic pathogen, MDR |
| *Klebsiella pneumoniae* subsp. *pneumoniae* ATCC 10031 | |
| *Klebsiella pneumoniae* KCTC 2242 | |
| *Klebsiella pneumoniae* ATCC 13883 | |
| *Klebsiella pneumoniae* Revco 41 | |

In the present invention, *P. putida* KCTC 1643 strain was treated with six types of translysins (PB1_gp48-iLCH$_N$-PRD1, PB1_gp48-iLCH$_N$-chee24, LysPA26-iLCH$_N$-PRD1, LysPA26-iLCH$_N$-chee24, T5Lys-iLCH$_N$-PRD1, T5Lys-iLCH$_N$-chee24), and the combinations exhibiting lytic activity were screened. The result showed that all translysins containing PRD1_04 RBP exhibited lytic activity against the target strain (FIG. 22).

The sequence additionally used to prepare the translysin is as follows:

```
T5Lys-Gp41.1N: SEQ ID NO: 27;
and
     CfaC-T5 like chee24: SEQ ID NO: 28.
```

The translysin of the present invention is a protein complex in which an antibacterial protein endolysin derived from a bacteriophage and a receptor-binding protein (RBP) are linked to the translocation domain H$_N$ of botulinum toxin, and was designed that RBP was disposed at the carboxyl terminus (C-terminal) and endolysin was disposed at the amino terminus (N-terminal) (FIG. 23) such that H$_N$ was disposed between the RBP and the endolysin.

Based on this design, when translysin interacts with the target strain, the RBP at the carboxyl-terminus recognizes and attaches to the receptor located on the outer membrane, then H$_N$ is incorporated into the cell membrane, and the endolysin at the amino terminal is close to peptidoglycan to induce lytic action and to kill cells (FIG. 24).

The translysin of the present invention was predicted to reach about 180 kDa in size. Considering the possibility of problems with yield and purity during the process of expressing and purifying translysin, a method of expressing the full-length protein and a method of separately expressing split protein fragments and then linking the fragments in vitro were performed respectively and compared. The result showed that the method of separately expressing the split protein fragments and then linking the same compensated for the drawbacks of the conventional method and was able to produce an intact full-length protein.

In the present invention, intein and SpyTag/Spycatcher are introduced as a means of binding respective fragments of endolysin, translocation domain, and RBP, and protein fragments are assembled into full-length proteins through protein trans-splicing and bioconjugation (FIGS. 25 and 26). In addition, novel antibacterial substances can be screened by combining various endolysins and RBPs using inteins and SpyTags/Spycatchers to construct a translysin library, and detecting the lytic activity of each translysin.

The invention claimed is:

1. An antibacterial composition comprising a protein complex comprising a botulinum toxin translocation domain and endolysin,
    wherein the botulinum toxin translocation domain comprises at least one amino acid sequence selected from the group consisting of SEQ ID NOS: 29, 38 and 39, and
    wherein the endolysin comprises at least one selected from the group consisting of lys, LysPA26, PB1_gp48, LysAB2_P3, PlyF307, AcLys, PlyPA03, PlyPA91, Abtn-4, WCHABP1_gp01, WCHABP12_gp19, gh-1p12, B3ORF25, phi-13Sp4, phi-6S_4, KP27_166, KP13_gp066, BI057_gp221, LPSE_00024, STP4a_120, Lys68, SPN1S_0028 and P22gp66.

2. The antibacterial composition according to claim 1, wherein the botulinum toxin translocation domain is connected to a C-terminus of the endolysin.

3. The antibacterial composition according to claim 1 further comprising a receptor-binding protein.

4. The antibacterial composition according to claim 3, wherein the botulinum toxin translocation domain is connected to a C-terminus of the endolysin, and the receptor-binding protein is connected to a C-terminus of the botulinum toxin translocation domain.

5. The antibacterial composition according to claim 1, wherein the antibacterial composition has a lytic effect on Gram-negative bacteria.

* * * * *